United States Patent
Buettelmann et al.

(10) Patent No.: US 7,678,815 B2
(45) Date of Patent: Mar. 16, 2010

(54) THIAZOLE-4-CARBOXYAMIDE DERIVATIVES

(75) Inventors: Bernd Buettelmann, Schopfheim (DE); Simona Maria Ceccarelli, Basel (CH); Georg Jaeschke, Basel (CH); Sabine Kolczewski, Rheinfelden (DE); Richard Hugh Philip Porter, Reinach (CH); Eric Vieira, Frenkendorf (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 1007 days.

(21) Appl. No.: 11/328,879

(22) Filed: Jan. 10, 2006

(65) Prior Publication Data

US 2006/0160857 A1 Jul. 20, 2006

(30) Foreign Application Priority Data

Jan. 14, 2005 (EP) .................................. 05100203

(51) Int. Cl.
*A61K 31/445* (2006.01)
*A61K 31/454* (2006.01)
*C07D 417/02* (2006.01)

(52) U.S. Cl. ....................... 514/326; 514/370; 546/208; 548/190

(58) Field of Classification Search ........................ None
See application file for complete search history.

(56) References Cited

U.S. PATENT DOCUMENTS

| 6,660,753 | B2 | 12/2003 | Van Wagenen et al. | |
| 7,105,682 | B2 * | 9/2006 | Chen et al. | 546/277.1 |
| 2008/0167309 | A1 * | 7/2008 | Berdini et al. | 514/236.8 |

FOREIGN PATENT DOCUMENTS

| EP | 1210344 | 6/2002 |
| WO | WO 98/05651 | 2/1998 |
| WO | WO 99/02497 | 1/1999 |
| WO | WO01/12627 | 2/2001 |
| WO | WO 02/066470 | 8/2002 |
| WO | WO 02/068406 | 9/2002 |
| WO | WO 02/068417 | 9/2002 |
| WO | WO 2006/008545 | 1/2006 |

OTHER PUBLICATIONS

Bonnefous et al., Bioorganic & Medicinal Chem. Letters, vol. 15, Issue 4 (Feb. 15, 2005) pp. 1197-1200.
Mutel, V., Expert Opin. Ther. Patents (2002) 12(12) pp. 1845-1852.
Suzuki et al., Synthesis, (1982) pp. 874-875.
Basha et al., Tetrahedron Lett. (1977) vol. 48, pp. 4171-4174.
Golankiewicz et al., Tetrahedron (1985) vol. 41, pp. 5989-5994.
Schlaeger et al., Cytotechnology vol. 30 pp. 71-83 (1999).
Porter et al., Br. J. Pharmacol. vol. 128, pp. 13-20 (1999).

* cited by examiner

*Primary Examiner*—Kamal A Saeed
(74) *Attorney, Agent, or Firm*—George W. Johnston; Patricia S. Rocha-Tramaloni; Kimberly J. Prior

(57) ABSTRACT

The present invention is concerned with novel thiazole 4-carboxyamide derivatives of the general formula (I) and with methods for the preparation thereof, which compounds are useful as metabotropic glutamate receptor antagonists:

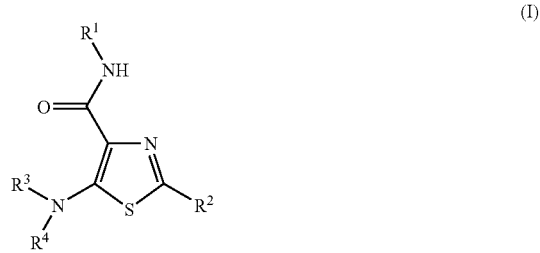

wherein $R^1$ to $R^4$ are as defined in the specification.

25 Claims, No Drawings

THIAZOLE-4-CARBOXAMIDE DERIVATIVES

PRIORITY TO RELATED APPLICATIONS

This application claims the benefit of European Application No. 05100203.8, filed Jan. 14, 2005, which is hereby incorporated by reference in its entirety.

BACKGROUND OF THE INVENTION

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of this mGluR family are known and of these some even have sub-types. According to their sequence homology, signal transduction mechanisms and agonist selectivity, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, obesity, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

Selective mGluR5 antagonists are especially useful for the treatment of anxiety and pain.

WO2002068417 already described a broad family of compounds useful as group I metabotropic glutamate receptor antagonists without disclosing the compounds of the instant invention.

SUMMARY OF THE INVENTION

The present invention provides thiazole 4-carboxamide derivatives of formula (I):

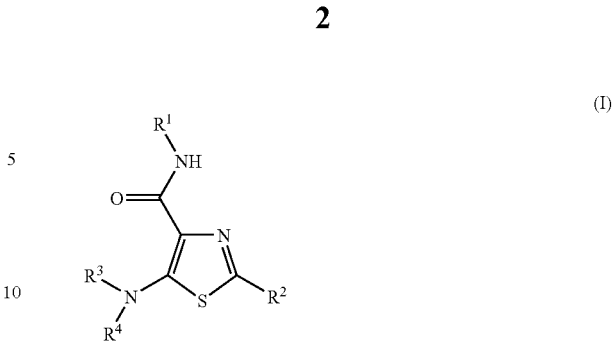

wherein $R^1$ is aryl or heteroaryl, each of which is optionally substituted by one or more substituents selected from the group consisting of —OH, chloro, fluoro, bromo, cyano, $C_1$-$C_7$-alkyl, $C_1$-$C_7$-alkoxy, —O—(CO)—$C_1$-$C_7$-alkyl, $C_3$-$C_6$-cycloalkyl, and —$(CH_2)_m$—$R^a$,
    wherein $R^a$ is —OH, —$CH_2F$, —$CHF_2$, —$CF_3$, $C_1$-$C_7$-alkoxy, $C_3$-$C_6$-cycloalkyl, —NH(CO)—$C_1$-$C_7$-alkyl, or —O—(CO)—$C_1$-$C_7$-alkyl;

$R^2$ is H, $C_1$-$C_7$-alkyl, —$(CH_2)_m$—O—$C_1$-$C_7$-alkyl or $C_3$-$C_6$-cycloalkyl;

$R^3$ is $C_1$-$C_7$-alkyl;
    —$(CH_2)_m$—$R^b$,
        wherein $R^b$ is —O—$C_1$-$C_7$-alkyl, $C_3$-$C_6$-cycloalkyl, 5 or 6 membered heterocycloalkyl, aryl optionally substituted by fluoro, or heteroaryl optionally substituted by $C_1$-$C_7$-alkyl;
    —(CO)—$R^c$,
        wherein $R^c$ is —O—$(CH_2)_m$—$C_3$-$C_6$-cycloalkyl or aryl;
    —$C_3$-$C_6$-cycloalkyl;
    5 or 6 membered heterocycloalkyl;
    aryl or heteroaryl, each of which is optionally substituted by a substituent selected from the group consisting of
        cyano,
        chloro,
        fluoro,
        bromo,
        $CF_3$,
        $CHF_2$,
        $C_3$-$C_6$-cycloalkyl, or
        —O—$C_1$-$C_7$-alkyl;
    —(CO)—$R^d$,
        wherein $R^d$ is $C_1$-$C_7$-alkyl, $NH_2$, or —O—$C_1$-$C_7$-alkyl;
    —$(CH_2)_m$—$R^e$,
        wherein $R^e$ is OH, $C_1$-$C_7$-alkoxy, $CHF_2$, $CF_3$, $NH_2$, —NH—(CO)—$C_1$-$C_7$-alkyl, or —NH—(CO)—O—$C_1$-$C_7$-alkyl;
    —NH—(CO)—$C_1$-$C_7$-alkyl;
    —O—$CH_2F$;
    —O—$CHF_2$;
    —O—$CF_3$;
    —$S(O)_2$—$R^f$,
        wherein $R^f$ is $C_1$-$C_7$-alkyl, —$NH_2$, —NH—$C_1$-$C_7$-alkyl or —N-di($C_1$-$C_7$-alkyl); or heteroaryl optionally substituted by $C_1$-$C_7$-alkyl;

$R^4$ is H, $C_1$-$C_7$-alkyl or $C_1$-$C_7$-alkyl-$C_3$-$C_6$-cycloalkyl; and m is 1 to 4;

and pharmaceutically acceptable salts thereof.

The invention also includes all racemic mixtures, all their corresponding enantiomers and/or optical isomers. The invention also provides pharmaceutical compositions containing compounds of the invention and methods for the manufacture of such compounds and compositions.

Compounds of formula I are metabotropic glutamate receptor antagonists. They can be used for the treatment or prevention of mGLuR5 receptor mediated disorders, such as acute and/or chronic neurological disorders including those described herein, in particular anxiety and chronic or acute pain.

DETAILED DESCRIPTION OF THE INVENTION

The following definitions of general terms used in the present description apply irrespective of whether the terms in question appear alone or in combination. It must be noted that, as used in the specification and the appended claims, the singular forms "a", "an," and "the" include plural forms unless the context dearly dictates otherwise.

"Aryl" means a monovalent cyclic aromatic hydrocarbon moiety consisting of a mono-, bi- or tricyclic aromatic ring system. Preferred aryl groups are $C_6$-$C_{10}$ aryl. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"$C_1$-$C_7$ alkyl" denotes a straight- or branched-carbon chain group containing from 1 to 7 carbon atoms, for example, methyl, ethyl, propyl, isopropyl, isobutyl, sec-butyl, tert-butyl, pentyl, n-hexyl as well as those specifically illustrated by the examples herein below.

"$C_1$-$C_7$ alkoxy" or "—O—$C_1$-$C_7$-alkyl" denotes a group wherein the alkyl group is as defined above and is connected via an oxygen atom.

"Halogen" denotes chlorine, iodine, fluorine and bromine.

"Heteroaryl" means a monocyclic, bicyclic or tricyclic radical of 5 to 12, preferably 5 to 9, ring atoms, still more preferably 5 to 6 ring atoms, having at least one aromatic ring and furthermore containing one, two, or three ring heteroatoms selected from N, O, or S, the remaining ring atoms being C. Heteroaryl can optionally be substituted with one, two, three or four substituents, wherein each substituent is independently hydroxy, cyano, alkyl, alkoxy, thioalkyl, halo, haloalkyl, hydroxyalkyl, alkoxycarbonyl, amino, acetyl, —NHCOOC(CH$_3$)$_3$, or halogen substituted benzyl, or for the non aromatic part of cyclic ring also by oxo, unless otherwise specifically indicated. Examples of heteroaryl moieties include, but are not limited to, optionally substituted imidazolyl, optionally substituted oxazolyl, optionally substituted thiazolyl, optionally substituted pyrazinyl, optionally substituted pyrrolyl, optionally substituted pyridinyl, optionally substituted pyrimdinyl, optionally substituted indonyl, optionally substituted isoquinolinyl, optionally substituted carbazol-9-yl, optionally substituted furanyl, optionally substituted benzofuranyl, optionally substituted benzo[1,2,3] thiadiazolyl, optionally substituted benzo[b]thiophenyl, optionally substituted 9H-thioxanthenyl, optionally substituted thieno[2,3-c]pyridinyl and the like or those which are specifically exemplified herein.

"$C_3$-$C_6$ cycloalkyl" denotes an aliphatic carbon ring having 3 to 6 carbon atoms as ring members and includes but is not limited to cyclopropyl, cyclobutyl, cyclopentyl, cyclohexyl, as well as those groups specifically illustrated by the examples herein below.

"4 to 7 membered heterocycloalkyl" denotes a saturated cyclic ring comprising from 1 to 6 carbon atoms as ring members, the other remaining ring member atoms being selected from one or more O, N and S. Preferred 4 to 7 membered heterocycloalkyl groups are 5 or 6 membered heterocycloalkyl groups. Examples of 4 to 7 and 5 or 6 membered heterocycloalkyl groups include, but are not limited to, optionally substituted piperidinyl, piperazinyl, homopiperazinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, quinuclidinyl, thiadiazolylidinyl, benzothiazolidinyl, benzoazolylidinyl, dihydrofuryl, tetrahydrofuryl, dihydropyranyl, tetrahydropyranyl, thiomorpholinyl, thiomorpholinylsulfoxide, thiomorpholinylsulfone, dihydroquinolinyl, dihydrisoquinolinyl, tetrahydroquinolinyl, tetrahydroisoquinolinyl, 1-oxo-thiomorpholin, 1,1-dioxo-thiomorpholin, 1,4-diazepane, 1,4-oxazepane as well as those groups specifically illustrated by the examples herein below.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid or base.

"Therapeutically effective amount" means an amount that is effective to prevent, alleviate or ameliorate symptoms of disease or prolong the survival of the subject being treated.

The present invention provides thiazole 4-carboxyamide derivatives of formula (I):

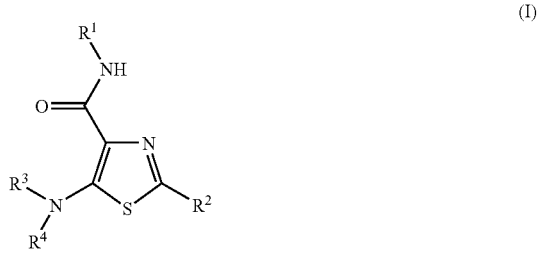

(I)

wherein $R^1$ is aryl or heteroaryl, each of which is optionally substituted by one or more substituents selected from the group consisting of —OH, chloro, fluoro, bromo, cyano, $C_1$-$C_7$-alkyl, $C_1$-$C_7$-alkoxy, —O—(CO)—$C_1$-$C_7$-alkyl, $C_3$-$C_6$-cycloalkyl, and —(CH$_2$)$_m$—R$^a$, wherein R$^a$ is —OH, —CH$_2$F, —CHF$_2$, —CF$_3$, $C_1$-$C_7$-alkoxy, $C_3$-$C_6$-cycloalkyl, —NH(CO)—$C_1$-$C_7$-alkyl, or —O—(CO)—$C_1$-$C_7$-alkyl;

$R^2$ is H, $C_1$-$C_7$-alkyl, —(CH$_2$)$_m$—O—$C_1$-$C_7$-alkyl or $C_3$-$C_6$-cycloalkyl;

$R^3$ is $C_1$-$C_7$-alkyl;

—(CH$_2$)$_m$—R$^b$, wherein $R^b$ is —O—$C_1$-$C_7$-alkyl, $C_3$-$C_6$-cycloalkyl, 5 or 6 membered heterocycloalkyl, aryl optionally substituted by fluoro, or heteroaryl optionally substituted by $C_1$-$C_7$-alkyl;
—(CO)—$R^c$,
wherein $R^c$ is —O—$(CH_2)_m$—$C_3$-$C_6$-cycloalkyl or aryl;
—$C_3$-$C_6$-cycloalkyl;
5 or 6 membered heterocycloalkyl;
aryl or heteroaryl, each of which is optionally substituted by a substituent selected from the group consisting of
cyano,
chloro,
fluoro,
bromo,
$CF_3$,
$CHF_2$,
$C_3$-$C_6$-cycloalkyl, or
—O—$C_1$-$C_7$-alkyl;
—(CO)—$R^d$,
wherein $R^d$ is $C_1$-$C_7$-alkyl, $NH_2$, or —O—$C_1$-$C_7$-alkyl;
—$(CH_2)_m$—$R^e$,
wherein $R^e$ is OH, $C_1$-$C_7$-alkoxy, $CHF_2$, $CF_3$, $NH_2$, —NH—(CO)—$C_1$-$C_7$-alkyl, or —NH—(CO)—O—$C_1$-$C_7$-alkyl;
—NH—(CO)—$C_1$-$C_7$-alkyl;
—O—$CH_2F$;
—O—$CHF_2$;
—O—$CF_3$;
—$S(O)_2$—$R^f$,
wherein $R^f$ is $C_1$-$C_7$-alkyl, —$NH_2$, —NH—$C_1$-$C_7$-alkyl or —N-di($C_1$-$C_7$-alkyl); or heteroaryl optionally substituted by $C_1$-$C_7$-alkyl;

$R^4$ is H, $C_1$-$C_7$-alkyl or $C_1$-$C_7$-alkyl-$C_3$-$C_6$-cycloalkyl; and m is 1 to 4;

and pharmaceutically acceptable salts thereof.

In certain embodiments, the compounds of the invention are those compounds wherein:

$R^1$ is aryl or heteroaryl, each of which is optionally substituted by one or more substituents selected from the group consisting of —OH, chloro, fluoro, bromo, cyano, $C_1$-$C_7$-alkyl, —O—(CO)—$C_1$-$C_7$-alkyl, and —$(CH_2)_m$—$R^a$,
wherein $R^a$ is —OH, —$CH_2F$, —$CHF_2$, —$CF_3$, or —O—(CO)—$C_1$-$C_7$-alkyl;

$R^2$ is H, $C_1$-$C_7$-alkyl, —$(CH_2)_m$—O—$C_1$-$C_7$-alkyl or $C_3$-$C_6$-cycloalkyl;

$R^3$ is $C_1$-$C_7$-alkyl;
—$(CH_2)_m$—$R^b$,
wherein $R^b$ is —O—$C_1$-$C_7$-alkyl, $C_3$-$C_6$-cycloalkyl, or aryl;
—(CO)—$R^c$,
wherein $R^c$ is —O—$(CH_2)_m$—$C_3$-$C_6$-cycloalkyl, or aryl;
$C_3$-$C_6$-cycloalkyl;
aryl or heteroaryl, each of which is optionally substituted by:
cyano,
chloro,
fluoro,
bromo,
$CF_3$,
$CHF_2$, or
—O—$C_1$-$C_7$-alkyl;
—(CO)—$R^d$,
wherein $R^d$ is $C_1$-$C_7$-alkyl, $NH_2$, or —O—$C_1$-$C_7$-alkyl;
—$(CH_2)_m$—$R^e$, wherein $R^e$ is OH, $NH_2$, or —NH—(CO)—O—$C_1$-$C_7$-alkyl;
—NH—(CO)—$C_1$-$C_7$-alkyl;
—O—$CH_2F$, —O—$CHF_2$, —O—$CF_3$; or
—$S(O)_2$—$R^f$,
wherein $R^f$ is $C_1$-$C_7$-alkyl, —$NH_2$, —NH—$C_1$-$C_7$-alkyl or —N-di($C_1$-$C_7$-alkyl), or heteroaryl optionally substituted by $C_1$-$C_7$-alkyl;

$R^4$ is H, $C_1$-$C_7$-alkyl or $C_1$-$C_7$-alkyl-$C_3$-$C_6$-cycloalkyl;

m is 1 to 4;

and pharmaceutically acceptable salts thereof.

In certain embodiments, the compounds of the invention are those compounds wherein:

$R^1$ is aryl or heteroaryl, each of which is optionally substituted by one or more substituents selected from the group consisting of —OH, chloro, fluoro, bromo, cyano, $C_1$-$C_7$-alkyl, $C_1$-$C_7$-alkoxy, —O—(CO)—$C_1$-$C_7$-alkyl, $C_3$-$C_6$-cycloalkyl, and —$(CH_2)_m$—$R^a$,
wherein $R^a$ is —OH, —$CH_2F$, —$CF_3$, $C_1$-$C_7$-alkoxy, $C_3$-$C_6$-cycloalkyl, —NH(CO)—$C_1$-$C_7$-alkyl, or —O—(CO)—$C_1$-$C_7$-alkyl;

$R^2$ is H, $C_1$-$C_7$-alkyl, —$(CH_2)_m$—O—$C_1$-$C_7$-alkyl or $C_3$-$C_6$-cycloalkyl;

$R^3$ is $C_1$-$C_7$-alkyl;
—$(CH_2)_m$—$R^b$,
wherein $R^b$ is —O—$C_1$-$C_7$-alkyl, $C_3$-$C_6$-cycloalkyl, 5 or 6 membered heterocycloalkyl, aryl optionally substituted by fluoro, or heteroaryl optionally substituted by $C_1$-$C_7$-alkyl;
—(CO)—$R^c$,
wherein $R^c$ is —O—$(CH_2)_m$—$C_3$-$C_6$-cycloalkyl, or aryl;
$C_3$-$C_6$-cycloalkyl;
5 or 6 membered heterocycloalkyl;
aryl or heteroaryl, each of which is optionally substituted by:
cyano, chloro, fluoro, bromo, $CF_3$ or —O—$C_1$-$C_7$-alkyl;
—(CO)—$R^d$,
wherein $R^d$ is $C_1$-$C_7$-alkyl, $NH_2$, or —O—$C_1$-$C_7$-alkyl;
—$(CH_2)_m$—$R^e$,
wherein $R^e$ is OH, $C_1$-$C_7$-alkoxy, $CHF_2$, $CF_3$, $NH_2$, —NH—(CO)—$C_1$-$C_7$-alkyl, or —NH—(CO)—O—$C_1$-$C_7$-alkyl;
—NH—(CO)—$C_1$-$C_7$-alkyl;
—O—$CHF_2$;
—$S(O)_2$—$R^f$,
wherein $R^f$ is $C_1$-$C_7$-alkyl, —$NH_2$, —NH—$C_1$-$C_7$-alkyl or —N-di($C_1$-$C_7$-alkyl); or
heteroaryl optionally substituted by $C_1$-$C_7$-alkyl;

$R^4$ is H, $C_1$-$C_7$-alkyl or $C_1$-$C_7$-alkyl-$C_3$-$C_6$-cycloalkyl;

m is 1 to 4;

and pharmaceutically acceptable salts thereof.

In certain embodiments of the compounds of the invention $R^3$ is
heteroaryl optionally substituted by cyano, chloro, fluoro, bromo, $CF_3$, $CHF_2$, or —O—$C_1$-$C_7$-alkyl;
—(CO)—$R^d$,
wherein $R^d$ is $C_1$-$C_7$-alkyl, $NH_2$, or —O—$C_1$-$C_7$-alkyl;
—$(CH_2)_m$—$R^e$,
wherein $R^e$ is OH, $C_1$-$C_7$-alkoxy, $CHF_2$, $CF_3$, $NH_2$, —NH—(CO)—$C_1$-$C_7$-alkyl, or —NH—(CO)—O—$C_1$-$C_7$-alkyl;
—NH—(CO)—$C_1$-$C_7$-alkyl;

—O—CH$_2$F;
—O—CHF$_2$;
—O—CF$_3$;
—S(O)$_2$—R$^f$,
wherein R$^f$ is C$_1$-C$_7$-alkyl, —NH$_2$, —NH—C$_1$-C$_7$-alkyl or —N-di(C$_1$-C$_7$-alkyl); or heteroaryl optionally substituted by C$_1$-C$_7$-alkyl; for example the following compounds:

5-(Pyridin-3-ylamino)-thiazole-4-carboxylic acid (6-methyl-pyridin-2-yl)-amide;
5-(Pyridin-3-ylamino)-thiazole-4-carboxylic acid (3-chloro-phenyl)-amide;
5-(Pyridin-3-ylamino)-thiazole-4-carboxylic acid (6-chloro-pyridin-2-yl)-amide;
5-(Pyridin-3-ylamino)-thiazole-4-carboxylic acid (6-bromo-pyridin-2-yl)-amide;
5-(Pyridin-3-ylamino)-thiazole-4-carboxylic acid (4-methyl-thiazol-2-yl)-amide;
5-(Pyridin-3-ylamino)-thiazole-4-carboxylic acid (2-methyl-thiazol-4-yl)-amide;
5-(Pyridin-3-ylamino)-thiazole-4-carboxylic acid m-tolylamide;
5-(Pyridin-3-ylamino)-thiazole-4-carboxylic acid (6-ethyl-pyridin-2-yl)-amide;
5-(Pyridin-3-ylamino)-thiazole-4-carboxylic acid (6-trifluoromethyl-pyridin-2-yl)-amide;
5-(3,5-Dimethyl-isoxazol-4-ylamino)-thiazole-4-carboxylic acid (3-chloro-phenyl)-amide;
5-(3,5-Dimethyl-isoxazol-4-ylamino)-thiazole-4-carboxylic acid m-tolylamide;
5-(3,5-Dimethyl-isoxazol-4-ylamino)-thiazole-4-carboxylic acid (6-methyl-pyridin-2-yl)-amide;
5-(3,5-Dimethyl-isoxazol-4-ylamino)-thiazole-4-carboxylic acid (6-bromo-pyridin-2-yl)-amide;
5-(3,5-Dimethyl-isoxazol-4-ylamino)-thiazole-4-carboxylic acid (4-methyl-thiazol-2-yl)-amide;
5-(2-Methoxy-pyridin-3-ylamino)-thiazole-4-carboxylic acid (6-methyl-pyridin-2-yl)-amide;
2-Methyl-5-(pyridin-3-ylamino)-thiazole-4-carboxylic acid (3-chloro-phenyl)-amide;
2-Methyl-5-(pyridin-3-ylamino)-thiazole-4-carboxylic acid (6-methyl-pyridin-2-yl)-amide;
2-Methyl-5-(pyridin-3-ylamino)-thiazole-4-carboxylic acid (2-methyl-thiazol-4-yl)-amide;
2-Methyl-5-(pyridin-3-ylamino)-thiazole-4-carboxylic acid (6-chloro-pyridin-2-yl)-amide;
2-Methyl-5-(pyridin-3-ylamino)-thiazole-4-carboxylic acid (6-bromo-pyridin-2-yl)-amide;
2-Methyl-5-(pyridin-3-ylamino)-thiazole-4-carboxylic acid (3-cyano-phenyl)-amide;
2-Methyl-5-(pyridin-3-ylamino)-thiazole-4-carboxylic acid (2-fluoro-5-methyl-phenyl)-amide;
2-Methyl-5-(pyridin-3-ylamino)-thiazole-4-carboxylic acid (5-chloro-2-fluoro-phenyl)-amide;
2-Methyl-5-(pyridin-3-ylamino)-thiazole-4-carboxylic acid (3-chloro-2-fluoro-phenyl)-amide;
2-Methyl-5-(pyridin-3-ylamino)-thiazole-4-carboxylic acid m-tolylamide;
2-Methyl-5-(pyridin-3-ylamino)-thiazole-4-carboxylic acid (6-fluoromethyl-pyridin-2-yl)-amide;
2-Methyl-5-(pyridin-3-ylamino)-thiazole-4-carboxylic acid (2-chloro-pyridin-4-yl)-amide;
2-Methyl-5-(pyridin-3-ylamino)-thiazole-4-carboxylic acid (2-methyl-pyridin-4-yl)-amide;
2-Methyl-5-(pyridin-3-ylamino)-thiazole-4-carboxylic acid (5-fluoro-pyridin-2-yl)-amide;
2-Methyl-5-(pyridin-3-ylamino)-thiazole-4-carboxylic acid (2-methyl-pyrimidin-4-yl)-amide;
2-Methyl-5-(pyrimidin-5-ylamino)-thiazole-4-carboxylic acid (6-chloro-pyridin-2-yl)-amide;
2-Methyl-5-(pyrimidin-5-ylamino)-thiazole-4-carboxylic acid (6-methyl-pyridin-2-yl)-amide;
2-Methyl-5-(pyrimidin-5-ylamino)-thiazole-4-carboxylic acid (2-methyl-thiazol-4-yl)-amide;
2-Methyl-5-(pyrimidin-5-ylamino)-thiazole-4-carboxylic acid (2-methyl-pyridin-4-yl)-amide;
2-Methyl-5-(pyrimidin-5-ylamino)-thiazole-4-carboxylic acid (5-fluoro-pyridin-2-yl)-amide;
2-Methyl-5-(pyrimidin-5-ylamino)-thiazole-4-carboxylic acid (3-chloro-phenyl)-amide;
2-Methyl-5-(4-methyl-pyridin-3-ylamino)-thiazole-4-carboxylic acid (3-chloro-phenyl)-amide;
2-Methyl-5-(4-methyl-pyridin-3-ylamino)-thiazole-4-carboxylic acid (6-methyl-pyridin-2-yl)-amide;
2-Methyl-5-(4-methyl-pyridin-3-ylamino)-thiazole-4-carboxylic acid (2-methyl-pyridin-4-yl)-amide;
5-(5-Cyano-pyridin-3-ylamino)-2-methyl-thiazole-4-carboxylic acid (3-chloro-phenyl)-amide;
5-(5-Cyano-pyridin-3-ylamino)-2-methyl-thiazole-4-carboxylic acid (6-methyl-pyridin-2-yl)-amide;
5-Amino-2-methyl-thiazole-4-carboxylic acid (3-chloro-phenyl)-amide;
2-Methyl-5-(pyridin-4-ylamino)-thiazole-4-carboxylic acid (3-chloro-phenyl)-amide;
2-Methyl-5-(2-methyl-pyridin-3-ylamino)-thiazole-4-carboxylic acid (6-methyl-pyridin-2-yl)-amide;
2-Methyl-5-(pyrazin-2-ylamino)-thiazole-4-carboxylic acid (6-methyl-pyridin-2-yl)-amide;
2-Methyl-5-(pyrimidin-2-ylamino)-thiazole-4-carboxylic acid (6-methyl-pyridin-2-yl)-amide;
2-Methyl-5-(pyridin-2-ylamino)-thiazole-4-carboxylic acid (6-methyl-pyridin-2-yl)-amide;
2-Methyl-5-(pyridazin-3-ylamino)-thiazole-4-carboxylic acid (6-methyl-pyridin-2-yl)-amide;
Acetic acid 6-{[2-methyl-5-(pyridin-3-ylamino)-thiazole-4-carbonyl]-amino}-pyridin-2-ylmethyl ester;
2-Methyl-5-(pyridin-3-ylamino)-thiazole-4-carboxylic acid (6-hydroxymethyl-pyridin-2-yl)-amide;
2-Methyl-5-(pyrimidin-5-ylamino)-thiazole-4-carboxylic acid (6-hydroxymethyl-pyridin-2-yl)-amide;
Acetic acid 2-methyl-6-{[2-methyl-5-(pyridin-3-ylamino)-thiazole-4-carbonyl]-amino}-pyridin-3-yl ester;
2-Methyl-5-(pyridin-3-ylamino)-thiazole-4-carboxylic acid (5-hydroxy-6-methyl-pyridin-2-yl)-amide;
2-Methyl-5-(pyrimidin-5-ylamino)-thiazole-4-carboxylic acid (5-hydroxy-6-methyl-pyridin-2-yl)-amide;
2-(2-Methoxy-ethyl)-5-(pyridin-3-ylamino)-thiazole-4-carboxylic acid (6-methyl-pyridin-2-yl)-amide;
2-Methoxymethyl-5-(pyridin-3-ylamino)-thiazole-4-carboxylic acid (6-methyl-pyridin-2-yl)-amide;
2-Cyclopropyl-5-(pyridin-3-ylamino)-thiazole-4-carboxylic acid (6-methyl-pyridin-2-yl)-amide;
2-Cyclobutyl-5-(pyridin-3-ylamino)-thiazole-4-carboxylic acid (6-methyl-pyridin-2-yl)-amide;
2-Ethyl-5-(pyridin-3-ylamino)-thiazole-4-carboxylic acid (6-methyl-pyridin-2-yl)-amide;
2-Propyl-5-(pyridin-3-ylamino)-thiazole-4-carboxylic acid (6-methyl-pyridin-2-yl)-amide;
2-Isopropyl-5-(pyridin-3-ylamino)-thiazole-4-carboxylic acid (6-methyl-pyridin-2-yl)-amide;
2-Methyl-5-(2-methyl-pyridin-3-ylamino)-thiazole-4-carboxylic acid (5-fluoro-pyridin-2-yl)-amide;

2-Methyl-5-((6-trifluoromethyl-pyridin-3-yl)amino)-thiazole-4-carboxylic acid (2-methyl-pyridin-4-yl)-amide;
2-Methyl-5-(2-methyl-pyridin-3-ylamino)-thiazole-4-carboxylic acid (2-methyl-pyridin-4-yl)-amide;
2-Methyl-5-(pyrazin-2-ylamino)-thiazole-4-carboxylic acid (5-fluoro-pyridin-2-yl)-amide;
5-(5-Chloro-pyridin-3-ylamino)-2-methyl-thiazole-4-carboxylic acid (5-fluoro-pyridin-2-yl)-amide;
2-Methyl-5-(4-methyl-pyridin-2-ylamino)-thiazole-4-carboxylic acid (5-fluoro-pyridin-2-yl)-amide;
2-Methyl-5-(pyrimidin-5-ylamino)-thiazole-4-carboxylic acid (2-chloro-pyridin-4-yl)-amide;
2-Methyl-5-(2-methyl-pyridin-4-ylamino)-thiazole-4-carboxylic acid (5-fluoro-pyridin-2-yl)-amide;
2-Methyl-5-(2-methyl-pyridin-3-ylamino)-thiazole-4-carboxylic acid (2-chloro-pyridin-4-yl)-amide;
2-Methyl-5-(pyrazin-2-ylamino)-thiazole-4-carboxylic acid (2-chloro-pyridin-4-yl)-amide;
5-(5-Chloro-pyridin-3-ylamino)-2-methyl-thiazole-4-carboxylic acid (2-methyl-pyridin-4-yl)-amide;
5-(5-Chloro-pyridin-3-ylamino)-2-methyl-thiazole-4-carboxylic acid (2-chloro-pyridin-4-yl)-amide;
5-(5-Cyano-pyridin-3-ylamino)-2-methyl-thiazole-4-carboxylic acid (5-fluoro-pyridin-2-yl)-amide;
5-(5-Cyano-pyridin-3-ylamino)-2-methyl-thiazole-4-carboxylic acid (2-methyl-pyrimidin-4-yl)-amide;
2-Methyl-5-(4-methyl-pyridin-3-ylamino)-thiazole-4-carboxylic acid (5-fluoro-pyridin-2-yl)-amide;
2-Methyl-5-(pyrimidin-5-ylamino)-thiazole-4-carboxylic acid (2-methyl-pyrimidin-4-yl)-amide;
5-(5-Cyano-pyridin-3-ylamino)-2-methyl-thiazole-4-carboxylic acid (2-methyl-pyridin-4-yl)-amide;
5-(5-Cyano-pyridin-3-ylamino)-2-methyl-thiazole-4-carboxylic acid (4-methyl-pyrimidin-2-yl)-amide;
2-Methyl-5-(4-methyl-pyridin-3-ylamino)-thiazole-4-carboxylic acid (2-chloro-pyridin-4-yl)-amide;
5-(5-Methanesulfonyl-pyridin-3-ylamino)-2-methyl-thiazole-4-carboxylic acid (2-methyl-pyridin-4-yl)-amide;
2-Methyl-5-(6-methyl-pyridazin-4-ylamino)-thiazole-4-carboxylic acid (2-methyl-pyridin-4-yl)-amide;
2-Methyl-5-(6-methyl-pyridazin-4-ylamino)-thiazole-4-carboxylic acid (2-chloro-pyridin-4-yl)-amide;
5-(Isoxazol-3-ylamino)-2-methyl-thiazole-4-carboxylic acid (2-methyl-pyrimidin-4-yl)-amide;
5-(4-Cyano-pyridin-2-ylamino)-2-methyl-thiazole-4-carboxylic acid (2-methyl-pyridin-4-yl)-amide;
5-(2-Chloro-pyridin-4-ylamino)-2-methyl-thiazole-4-carboxylic acid (2-methyl-pyridin-4-yl)-amide;
5-(4-Chloro-pyridin-2-ylamino)-2-methyl-thiazole-4-carboxylic acid (2-methyl-pyrimidin-4-yl)-amide;
2-Methyl-5-(pyrimidin-5-ylamino)-thiazole-4-carboxylic acid (3-chloro-4-fluoro-phenyl)-amide;
5-(5-Methanesulfonyl-pyridin-3-ylamino)-2-methyl-thiazole-4-carboxylic acid (6-fluoro-pyridin-3-yl)-amide;
5-(5-Methanesulfonyl-pyridin-3-ylamino)-2-methyl-thiazole-4-carboxylic acid (2-methyl-pyrimidin-4-yl)-amide;
2-Methyl-5-(pyrimidin-5-ylamino)-thiazole-4-carboxylic acid (4-fluoro-3-methyl-phenyl)-amide;
2-Methyl-5-(pyridin-3-ylamino)-thiazole-4-carboxylic acid (2-ethyl-pyrimidin-4-yl)-amide;
2-Methyl-5-(5-methyl-pyridin-3-ylamino)-thiazole-4-carboxylic acid (5-fluoro-pyridin-2-yl)-amide;
5-(2-Chloro-pyridin-4-ylamino)-2-methyl-thiazole-4-carboxylic acid (2-methyl-pyrimidin-4-yl)-amide;
5-(5-Methoxy-pyridin-3-ylamino)-2-methyl-thiazole-4-carboxylic acid (2-methyl-pyridin-4-yl)-amide;
2-Methyl-5-(5-methyl-pyridin-3-ylamino)-thiazole-4-carboxylic acid (2-methyl-pyridin-4-yl)-amide;
5-(5-Fluoro-pyridin-3-ylamino)-2-methyl-thiazole-4-carboxylic acid (2-methyl-pyridin-4-yl)-amide;
2-Methyl-5-(2-methyl-2H-pyrazol-3-ylamino)-thiazole-4-carboxylic acid (2-methyl-pyridin-4-yl)-amide;
2-Methyl-5-(pyridin-3-ylamino)-thiazole-4-carboxylic acid (4-methyl-pyrimidin-2-yl)-amide;
2-Methyl-5-(pyridin-2-ylamino)-thiazole-4-carboxylic acid (2-chloro-pyridin-4-yl)-amide;
2-Methyl-5-((5-trifluoromethyl-pyridin-3-yl)amino)-thiazole-4-carboxylic acid (2-methyl-pyridin-4-yl)-amide;
5-(4-Fluoro-pyridin-2-ylamino)-2-methyl-thiazole-4-carboxylic acid (2-methyl-pyridin-4-yl)-amide;
5-(2-Chloro-pyridin-4-ylamino)-2-methyl-thiazole-4-carboxylic acid (2-chloro-pyridin-4-yl)-amide;
5-(5-Hydroxymethyl-pyridin-3-ylamino)-2-methyl-thiazole-4-carboxylic acid (2-methyl-pyridin-4-yl)-amide;
5-(2-Cyano-pyridin-4-ylamino)-2-methyl-thiazole-4-carboxylic acid (2-methyl-pyridin-4-yl)-amide;
2-Methyl-5-(2-methyl-2H-pyrazol-3-ylamino)-thiazole-4-carboxylic acid (2-chloro-pyridin-4-yl)-amide;
5-[2-Methyl-4-(2-methyl-pyridin-4-ylcarbamoyl)-thiazol-5-ylamino]-nicotinamide;
2-Methyl-5-(5-sulfamoyl-pyridin-3-ylamino)-thiazole-4-carboxylic acid (2-methyl-pyridin-4-yl)-amide;
5-(5-Fluoro-pyridin-3-ylamino)-2-methyl-thiazole-4-carboxylic acid (2-chloro-pyridin-4-yl)-amide;
5-(5-Fluoro-pyridin-3-ylamino)-2-methyl-thiazole-4-carboxylic acid (4-methyl-thiazol-2-yl)-amide;
5-(5-Fluoro-pyridin-3-ylamino)-2-methyl-thiazole-4-carboxylic acid (2-methyl-pyrimidin-4-yl)-amide;
5-(4-Fluoro-pyridin-2-ylamino)-2-methyl-thiazole-4-carboxylic acid (2-methyl-pyrimidin-4-yl)-amide;
5-(5-Fluoro-pyridin-3-ylamino)-2-methyl-thiazole-4-carboxylic acid (5-fluoro-pyridin-2-yl)-amide;
5-(5-Fluoro-pyridin-3-ylamino)-2-methyl-thiazole-4-carboxylic acid (1-methyl-1H-pyrazol-3-yl)-amide;
2-Methyl-5-[(pyridin-3-ylmethyl)-amino]-thiazole-4-carboxylic acid (2-methyl-pyridin-4-yl)-amide;
2-Methyl-5-(2-methyl-2H-pyrazol-3-ylamino)-thiazole-4-carboxylic acid (2-methyl-pyrimidin-4-yl)-amide;
5-(2-Ethyl-2H-pyrazol-3-ylamino)-2-methyl-thiazole-4-carboxylic acid (2-methyl-pyrimidin-4-yl)-amide;
5-(2,5-Dimethyl-2H-pyrazol-3-ylamino)-2-methyl-thiazole-4-carboxylic acid (2-methyl-pyrimidin-4-yl)-amide;
2-Methyl-5-(1-methyl-1H-pyrazol-4-ylamino)-thiazole-4-carboxylic acid (2-methyl-pyrimidin-4-yl)-amide;
2-Methyl-5-(3-methyl-isoxazol-5-ylamino)-thiazole-4-carboxylic acid (2-methyl-pyrimidin-4-yl)-amide;
2-Methyl-5-(1-methyl-1H-pyrazol-3-ylamino)-thiazole-4-carboxylic acid (2-methyl-pyrimidin-4-yl)-amide;
2-Methyl-5-(1-methyl-1H-pyrazol-4-ylamino)-thiazole-4-carboxylic acid (2-methyl-pyrimidin-4-yl)-amide;
5-(5-Difluoromethyl-pyridin-3-ylamino)-2-methyl-thiazole-4-carboxylic acid (2-methyl-pyridin-4-yl)-amide;
5-(5-Fluoro-pyridin-3-ylamino)-2-methyl-thiazole-4-carboxylic acid (4-trifluoromethyl-thiazol-2-yl)-amide;
2-Methyl-5-(thiazol-2-ylamino)-thiazole-4-carboxylic acid (2-methyl-pyridin-4-yl)-amide;
5-(5-Chloro-pyridin-3-ylamino)-2-methyl-thiazole-4-carboxylic acid (1-methyl-1H-pyrazol-3-yl)-amide;
2-Methyl-5-(pyrimidin-5-ylamino)-thiazole-4-carboxylic acid (1-methyl-1H-pyrazol-3-yl)-amide;
5-(4-Cyano-2-methyl-2H-pyrazol-3-ylamino)-2-methyl-thiazole-4-carboxylic acid (2-methyl-pyridin-4-yl)-amide;

5-(5-Cyclopropyl-2-methyl-2H-pyrazol-3-ylamino)-2-methyl-thiazole-4-carboxylic acid (2-methyl-pyridin-4-yl)-amide;
2-Methyl-5-(2-methyl-2H-pyrazol-3-ylamino)-thiazole-4-carboxylic acid (1-methyl-1H-pyrazol-3-yl)-amide;
5-(2-Chloro-pyridin-4-ylamino)-2-methyl-thiazole-4-carboxylic acid (1-methyl-1H-pyrazol-3-yl)-amide;
2-Methyl-5-[2-(2,2,2-trifluoro-ethyl)-2H-pyrazol-3-ylamino]-thiazole-4-carboxylic acid (2-methyl-pyridin-4-yl)-amide;
5-(5-Cyclopropyl-2-methyl-2H-pyrazol-3-ylamino)-2-methyl-thiazole-4-carboxylic acid (1-methyl-1H-pyrazol-3-yl)-amide;
5-(5-Cyclopropyl-2-methyl-2H-pyrazol-3-ylamino)-2-methyl-thiazole-4-carboxylic acid (4-trifluoromethyl-thiazol-2-yl)-amide;
2-Methyl-5-(2-methyl-5-trifluoromethyl-2H-pyrazol-3-ylamino)-thiazole-4-carboxylic acid (2-methyl-pyridin-4-yl)-amide;
5-(5-Fluoro-pyridin-3-ylamino)-2-methyl-thiazole-4-carboxylic acid (4-cyclopropyl-thiazol-2-yl)-amide;
5-(5-Fluoro-pyridin-3-ylamino)-2-methyl-thiazole-4-carboxylic acid (3-methoxymethyl-phenyl)-amide;
5-(5-Fluoro-pyridin-3-ylamino)-2-methyl-thiazole-4-carboxylic acid [1-(2-methoxy-ethyl)-1H-pyrazol-3-yl]-amide;
2-Methyl-5-(pyridin-3-ylamino)-thiazole-4-carboxylic acid (4-trifluoromethyl-thiazol-2-yl)-amide;
2-Methyl-5-(pyridin-3-ylamino)-thiazole-4-carboxylic acid (1-methyl-1H-pyrazol-3-yl)-amide;
2-Methyl-5-(pyridin-3-ylamino)-thiazole-4-carboxylic acid [1-(2-methoxy-ethyl)-1H-pyrazol-3-yl]-amide;
2-Methyl-5-(pyridin-3-ylamino)-thiazole-4-carboxylic acid (4-cyclopropyl-thiazol-2-yl)-amide;
2-Methyl-5-(pyridin-3-ylamino)-thiazole-4-carboxylic acid (4-methyl-thiazol-2-yl)-amide;
2-Methyl-5-(pyridin-3-ylamino)-thiazole-4-carboxylic acid thiazol-2-ylamide;
5-(5-Cyclopropyl-2-methyl-2H-pyrazol-3-ylamino)-2-methyl-thiazole-4-carboxylic acid (4-methyl-thiazol-2-yl)-amide;
5-(2-Chloro-pyridin-4-ylamino)-2-methyl-thiazole-4-carboxylic acid (4-methyl-thiazol-2-yl)-amide;
2-Methyl-5-(pyridin-3-ylamino)-thiazole-4-carboxylic acid (5-ethyl-thiazol-2-yl)-amide;
2-Methyl-5-(pyrimidin-5-ylamino)-thiazole-4-carboxylic acid (4-methyl-thiazol-2-yl)-amide;
2-Methyl-5-(1-methyl-1H-pyrazol-4-ylamino)-thiazole-4-carboxylic acid (4-methyl-thiazol-2-yl)-amide;
2-Methyl-5-(pyridin-2-ylamino)-thiazole-4-carboxylic acid (4-methyl-thiazol-2-yl)-amide;
5-(2,5-Dimethyl-2H-pyrazol-3-ylamino)-2-methyl-thiazole-4-carboxylic acid (4-methyl-thiazol-2-yl)-amide;
2-Methyl-5-(1-methyl-1H-pyrazol-3-ylamino)-thiazole-4-carboxylic acid (4-methyl-thiazol-2-yl)-amide;
2-Methyl-5-(pyridin-4-ylamino)-thiazole-4-carboxylic acid (4-methyl-thiazol-2-yl)-amide;
5-(5-Difluoromethyl-pyridin-3-ylamino)-2-methyl-thiazole-4-carboxylic acid (4-methyl-thiazol-2-yl)-amide;
2-Methyl-5-(pyrimidin-2-ylamino)-thiazole-4-carboxylic acid (4-methyl-thiazol-2-yl)-amide;
2-Methyl-5-[(pyridin-3-ylmethyl)-amino]-thiazole-4-carboxylic acid (4-methyl-thiazol-2-yl)-amide;
2-Methyl-5-(pyridin-3-ylamino)-thiazole-4-carboxylic acid (5-methyl-4H-[1,2,4]triazol-3-yl)-amide;
2-Methyl-5-(pyridin-3-ylamino)-thiazole-4-carboxylic acid (4-methoxymethyl-thiazol-2-yl)-amide;
5-(5-Cyano-pyridin-3-ylamino)-2-methyl-thiazole-4-carboxylic acid (4-methyl-thiazol-2-yl)-amide;
5-(5-Fluoro-pyridin-3-ylamino)-2-methyl-thiazole-4-carboxylic acid (2-methyl-thiazol-4-yl)-amide;
5-(2-Chloro-pyridin-4-ylamino)-2-methyl-thiazole-4-carboxylic acid (2-methyl-thiazol-4-yl)-amide;
5-(5-Chloro-pyridin-3-ylamino)-2-methyl-thiazole-4-carboxylic acid (4-methyl-thiazol-2-yl)-amide;
2-Methyl-5-(2-methyl-pyridin-4-ylamino)-thiazole-4-carboxylic acid (4-methyl-thiazol-2-yl)-amide; and
5-(4-Fluoro-pyridin-2-ylamino)-2-methyl-thiazole-4-carboxylic acid (4-methyl-thiazol-2-yl)-amide.

In certain embodiments of the compound of the invention $R^3$ is
heteroaryl optionally substituted by
cyano,
chloro,
fluoro,
bromo,
$CF_3$,
$CHF_2$, or
—O—$C_1$-$C_7$-alkyl; or
heteroaryl optionally substituted by $C_1$-$C_7$-alkyl; in particular, compounds where $R^3$ is pyridine, or compounds where $R^3$ is pyridazine, pyrimidine, or pyrazine.

In certain embodiments of the compounds of the invention $R^3$ is
aryl optionally substituted by cyano, chloro, fluoro, bromo, $CF_3$, $CHF_2$, or —O—$C_1$-$C_7$-alkyl;
—(CO)—$R^d$,
wherein $R^d$ is $C_1$-$C_7$-alkyl, $NH_2$, or —O—$C_1$-$C_7$-alkyl;
—$(CH_2)_m$—$R^e$,
wherein $R^e$ is OH, $NH_2$, or —NH—(CO)—O—$C_1$-$C_7$-alkyl;
—NH—(CO)—$C_1$-$C_7$-alkyl;
—O—$CH_2$F;
—O—$CHF_2$;
—O—$CF_3$;
—S(O)$_2$—$R^f$,
wherein $R^f$ is $C_1$-$C_7$-alkyl, —$NH_2$, —NH—$C_1$-$C_7$-alkyl or —N-di($C_1$-$C_7$-alkyl); or heteroaryl optionally substituted by $C_1$-$C_7$-alkyl; for example the following compounds:
5-Phenylamino-thiazole-4-carboxylic acid phenylamide;
5-Phenylamino-thiazole-4-carboxylic acid (3-chloro-phenyl)-amide;
5-Phenylamino-thiazole-4-carboxylic acid (3-fluoro-phenyl)-amide;
5-Phenylamino-thiazole-4-carboxylic acid (6-methyl-pyridin-2-yl)-amide;
5-Phenylamino-thiazole-4-carboxylic acid (6-chloro-pyridin-2-yl)-amide;
5-Phenylamino-thiazole-4-carboxylic acid thiazol-2-ylamide;
5-Phenylamino-thiazole-4-carboxylic acid (4-methyl-2-yl)-amide;
5-(3-Chloro-phenylamino)-thiazole-4-carboxylic acid (3-chloro-phenyl)-amide;
5-(2,6-Dichloro-phenylamino)-thiazole-4-carboxylic acid (3-chloro-phenyl)-amide;
5-(2,6-Dichloro-phenylamino)-thiazole-4-carboxylic acid m-tolylamide;
5-(2,6-Dichloro-phenylamino)-thiazole-4-carboxylic acid (6-methyl-pyridin-2-yl)-amide;
5-(2,6-Dichloro-phenylamino)-thiazole-4-carboxylic acid (6-bromo-pyridin-2-yl)-amide;

5-(2,6-Dichloro-phenylamino)-thiazole-4-carboxylic acid (4-methyl-thiazol-2-yl)-amide;
5-(3-Cyano-phenylamino)-thiazole-4-carboxylic acid (3-chloro-phenyl)-amide;
5-(3-Cyano-phenylamino)-thiazole-4-carboxylic acid m-tolylamide;
5-(3-Cyano-phenylamino)-thiazole-4-carboxylic acid (6-methyl-pyridin-2-yl)-amide;
5-(3-Cyano-phenylamino)-thiazole-4-carboxylic acid (6-bromo-pyridin-2-yl)-amide;
5-(3-Cyano-phenylamino)-thiazole-4-carboxylic acid (4-methyl-thiazol-2-yl)-amide;
5-(3-Cyano-phenylamino)-thiazole-4-carboxylic acid (2-methyl-thiazol-4-yl)-amide;
5-o-Tolylamino-thiazole-4-carboxylic acid (3-chloro-phenyl)-amide;
5-o-Tolylamino-thiazole-4-carboxylic acid m-tolylamide;
5-o-Tolylamino-thiazole-4-carboxylic acid (6-methyl-pyridin-2-yl)-amide;
5-o-Tolylamino-thiazole-4-carboxylic acid (4-methyl-thiazol-2-yl)-amide;
5-(2-Bromo-phenylamino)-thiazole-4-carboxylic acid (6-methyl-pyridin-2-yl)-amide;
5-(3-Acetyl-phenylamino)-thiazole-4-carboxylic acid (6-methyl-pyridin-2-yl)-amide;
5-(3,5-Dimethoxy-phenylamino)-thiazole-4-carboxylic acid (6-methyl-pyridin-2-yl)-amide;
5-(3,5-Dimethoxy-phenylamino)-thiazole-4-carboxylic acid m-tolylamide;
5-(3-Methoxy-phenylamino)-thiazole-4-carboxylic acid (6-methyl-pyridin-2-yl)-amide;
5-(3-Fluoro-phenylamino)-thiazole-4-carboxylic acid (6-methyl-pyridin-2-yl)-amide;
5-(2-Fluoro-phenylamino)-thiazole-4-carboxylic acid (6-methyl-pyridin-2-yl)-amide;
5-(4-Fluoro-phenylamino)-thiazole-4-carboxylic acid (6-methyl-pyridin-2-yl)-amide;
5-(2,5-Difluoro-phenylamino)-thiazole-4-carboxylic acid (6-methyl-pyridin-2-yl)-amide;
5-(2,6-Difluoro-phenylamino)-thiazole-4-carboxylic acid (6-methyl-pyridin-2-yl)-amide;
5-(3,5-Difluoro-phenylamino)-thiazole-4-carboxylic acid (6-methyl-pyridin-2-yl)-amide;
5-(2,3-Difluoro-phenylamino)-thiazole-4-carboxylic acid (6-methyl-pyridin-2-yl)-amide;
5-(2,5-Difluoro-phenylamino)-thiazole-4-carboxylic acid (2-methyl-pyrimidin-4-yl)-amide;
3-[4-(3-Chloro-phenylcarbamoyl)-2-methyl-thiazol-5-ylamino]-benzoic acid methyl ester;
5-(3-Hydroxymethyl-phenylamino)-2-methyl-thiazole-4-carboxylic acid (3-chloro-phenyl)-amide;
5-(3-Acetylamino-phenylamino)-2-methyl-thiazole-4-carboxylic acid (3-chloro-phenyl)-amide;
2-Methyl-5-(3-sulfamoyl-phenylamino)-thiazole-4-carboxylic acid (3-chloro-phenyl)-amide;
{3-[4-(3-Chloro-phenylcarbamoyl)-2-methyl-thiazol-5-ylamino]-benzyl}-carbamic acid tert-butyl ester;
5-(3-Aminomethyl-phenylamino)-2-methyl-thiazole-4-carboxylic acid (3-chloro-phenyl)-amide;
3-[2-Methyl-4-(6-methyl-pyridin-2-ylcarbamoyl)-thiazol-5-ylamino]-benzoic acid methyl ester;
5-(3-Hydroxymethyl-phenylamino)-2-methyl-thiazole-4-carboxylic acid (6-methyl-pyridin-2-yl)-amide;
5-(3-Methanesulfonyl-phenylamino)-2-methyl-thiazole-4-carboxylic acid (6-methyl-pyridin-2-yl)-amide;
2-Methyl-5-(3-sulfamoyl-phenylamino)-thiazole-4-carboxylic acid (6-methyl-pyridin-2-yl)-amide;
5-(2-Fluoro-5-methanesulfonyl-phenylamino)-2-methyl-thiazole-4-carboxylic acid (2-methyl-pyridin-4-yl)-amide;
2-Methyl-5-(3-sulfamoyl-phenylamino)-thiazole-4-carboxylic acid (2-methyl-pyridin-4-yl)-amide;
2-Methyl-5-(3-sulfamoyl-phenylamino)-thiazole-4-carboxylic acid (5-fluoro-pyridin-2-yl)-amide;
5-(3-Methanesulfonyl-phenylamino)-2-methyl-thiazole-4-carboxylic acid (5-fluoro-pyridin-2-yl)-amide;
5-(4-Fluoro-phenylamino)-2-methyl-thiazole-4-carboxylic acid (2-chloro-pyridin-4-yl)-amide;
5-((3-Difluoromethoxy-phenyl)amino)-2-methyl-thiazole-4-carboxylic acid (5-fluoro-pyridin-2-yl)-amide;
5-(3-Diethylsulfamoyl-phenylamino)-2-methyl-thiazole-4-carboxylic acid (5-fluoro-pyridin-2-yl)-amide;
2-Methyl-5-(3-oxazol-5-yl-phenylamino)-thiazole-4-carboxylic acid (2-methyl-pyrimidin-4-yl)-amide;
5-(3-Fluoro-phenylamino)-2-methyl-thiazole-4-carboxylic acid (2-methyl-pyrimidin-4-yl)-amide;
5-(3-Cyano-phenylamino)-2-methyl-thiazole-4-carboxylic acid (2-methyl-pyrimidin-4-yl)-amide;
5-(3-Ethylsulfamoyl-phenylamino)-2-methyl-thiazole-4-carboxylic acid (5-fluoro-pyridin-2-yl)-amide;
5-(3,5-Difluoro-phenylamino)-2-methyl-thiazole-4-carboxylic acid (2-methyl-pyrimidin-4-yl)-amide;
5-(3-Methanesulfonyl-phenylamino)-2-methyl-thiazole-4-carboxylic acid (2-methyl-pyrimidin-4-yl)-amide;
5-(3-Fluoro-phenylamino)-2-methyl-thiazole-4-carboxylic acid (2-methyl-pyridin-4-yl)-amide;
5-(3,5-Difluoro-phenylamino)-2-methyl-thiazole-4-carboxylic acid (2-methyl-pyridin-4-yl)-amide;
5-(3-Carbamoyl-phenylamino)-2-methyl-thiazole-4-carboxylic acid (2-methyl-pyrimidin-4-yl)-amide;
2-Methyl-5-((3-trifluoromethyl-phenyl)amino)-thiazole-4-carboxylic acid (2-methyl-pyridin-4-yl)-amide;
5-(3-Carbamoyl-phenylamino)-2-methyl-thiazole-4-carboxylic acid (2-methyl-pyridin-4-yl)-amide;
5-(3-Cyano-phenylamino)-2-methyl-thiazole-4-carboxylic acid (2-methyl-pyridin-4-yl)-amide;
3-[2-Methyl-4-(2-methyl-pyridin-4-ylcarbamoyl)-thiazol-5-ylamino]-benzoic acid methyl ester;
5-(2,5-Difluoro-phenylamino)-2-methyl-thiazole-4-carboxylic acid (2-methyl-pyridin-4-yl)-amide;
5-(3,5-Difluoro-phenylamino)-2-methyl-thiazole-4-carboxylic acid (2-chloro-pyridin-4-yl)-amide;
5-(3-Hydroxymethyl-phenylamino)-2-methyl-thiazole-4-carboxylic acid (2-methyl-pyridin-4-yl)-amide;
5-(3-Chloro-5-fluoro-phenylamino)-2-methyl-thiazole-4-carboxylic acid (2-methyl-pyridin-4-yl)-amide;
5-(3-Hydroxymethyl-phenylamino)-2-methyl-thiazole-4-carboxylic acid (2-chloro-pyridin-4-yl)-amide;
5-(3-Cyano-5-fluoro-phenylamino)-2-methyl-thiazole-4-carboxylic acid (2-methyl-pyridin-4-yl)-amide;
5-(3,5-Difluoro-phenylamino)-2-methyl-thiazole-4-carboxylic acid (2-hydroxymethyl-pyridin-4-yl)-amide;
5-(3-Imidazol-1-yl-phenylamino)-2-methyl-thiazole-4-carboxylic acid (2-methyl-pyridin-4-yl)-amide;
2-Methyl-5-[3-(1-methyl-1H-pyrazol-3-yl)-phenylamino]-thiazole-4-carboxylic acid (2-methyl-pyridin-4-yl)-amide;
5-(3,5-Difluoro-phenylamino)-2-methyl-thiazole-4-carboxylic acid (4-methyl-thiazol-2-yl)-amide;
5-(3,5-Difluoro-phenylamino)-2-methyl-thiazole-4-carboxylic acid (1-methyl-1H-[1,2,4]triazol-3-yl)-amide;
5-(3,5-Difluoro-phenylamino)-2-methyl-thiazole-4-carboxylic acid (3-methyl-[1,2,4]thiadiazol-5-yl)-amide;
5-(3,5-Difluoro-phenylamino)-2-methyl-thiazole-4-carboxylic acid (1-methyl-1H-pyrazol-3-yl)-amide;

2-Methyl-5-(3-[1,2,3]triazol-1-yl-phenylamino)-thiazole-4-carboxylic acid (2-methyl-pyridin-4-yl)-amide;
2-Methyl-5-[3-(2-methyl-imidazol-1-yl)-phenylamino]-thiazole-4-carboxylic acid (2-methyl-pyridin-4-yl)-amide;
{3-[2-Methyl-4-(2-methyl-pyridin-4-ylcarbamoyl)-thiazol-5-ylamino]-benzyl}-carbamic acid tert-butyl ester;
5-(3,5-Difluoro-phenylamino)-2-methyl-thiazole-4-carboxylic acid (1-cyclopropylmethyl-1H-pyrazol-3-yl)-amide;
5-(3-Methoxymethyl-phenylamino)-2-methyl-thiazole-4-carboxylic acid (2-methyl-pyridin-4-yl)-amide;
5-(3,5-Difluoro-phenylamino)-2-methyl-thiazole-4-carboxylic acid [3-(acetylamino-methyl)-phenyl]-amide;
5-(3-Cyano-5-fluoro-phenylamino)-2-methyl-thiazole-4-carboxylic acid (1-methyl-1H-pyrazol-3-yl)-amide;
5-(3,5-Difluoro-phenylamino)-2-methyl-thiazole-4-carboxylic acid (4-cyclopropyl-thiazol-2-yl)-amide;
5-(3,5-Difluoro-phenylamino)-2-methyl-thiazole-4-carboxylic acid (3-methoxymethyl-phenyl)-amide;
5-(3,5-Difluoro-phenylamino)-2-methyl-thiazole-4-carboxylic acid [1-(2-methoxy-ethyl)-1H-pyrazol-3-yl]-amide;
5-[3-(Acetylamino-methyl)-phenylamino]-2-methyl-thiazole-4-carboxylic acid (2-methyl-pyridin-4-yl)-amide;
5-(3,5-Difluoro-phenylamino)-2-methyl-thiazole-4-carboxylic acid (5-fluoro-6-methyl-pyridin-2-yl)-amide;
5-(3,5-Difluoro-phenylamino)-2-methyl-thiazole-4-carboxylic acid (4-methoxymethyl-thiazol-2-yl)-amide;
5-(3-Methoxymethyl-phenylamino)-2-methyl-thiazole-4-carboxylic acid (1-methyl-1H-pyrazol-3-yl)-amide;
5-(3-Hydroxymethyl-phenylamino)-2-methyl-thiazole-4-carboxylic acid (1-methyl-1H-pyrazol-3-yl)-amide;
5-(3,5-Difluoro-phenylamino)-2-methyl-thiazole-4-carboxylic acid [1,3,4]thiadiazol-2-ylamide;
5-(3,5-Difluoro-phenylamino)-2-methyl-thiazole-4-carboxylic acid (5-methyl-1H-[1,2,4]triazol-3-yl)-amide;
5-(2,5-Difluoro-phenylamino)-2-methyl-thiazole-4-carboxylic acid (1-methyl-1H-pyrazol-3-yl)-amide;
5-(3-Cyano-phenylamino)-2-methyl-thiazole-4-carboxylic acid (1-methyl-1H-pyrazol-3-yl)-amide; and
5-(3,5-Difluoro-phenylamino)-2-methyl-thiazole-4-carboxylic acid (3-cyano-5-fluoro-phenyl)-amide;

In certain embodiments of the compounds of the invention $R^3$ is $C_1$-$C_7$-alkyl, for example the following compounds:
5-Methylamino-thiazole-4-carboxylic acid (3-chloro-phenyl)-amide;
5-Methylamino-thiazole-4-carboxylic acid (3-fluoro-phenyl)-amide;
5-Methylamino-thiazole-4-carboxylic acid phenylamide;
5-Methylamino-thiazole-4-carboxylic acid m-tolylamide;
5-Methylamino-thiazole-4-carboxylic acid (3-bromo-phenyl)-amide;
5-Methylamino-thiazole-4-carboxylic acid (6-chloro-pyridin-2-yl)-amide;
5-Methylamino-thiazole-4-carboxylic acid (6-bromo-pyridin-2-yl)-amide;
5-Methylamino-thiazole-4-carboxylic acid (6-methyl-pyridin-2-yl)-amide;
5-Isobutylamino-thiazole-4-carboxylic acid (3-chloro-phenyl)-amide;
5-Isobutylamino-thiazole-4-carboxylic acid (3-fluoro-phenyl)-amide;
5-Isobutylamino-thiazole-4-carboxylic acid phenylamide;
5-Isobutylamino-thiazole-4-carboxylic acid m-tolylamide;
5-Isobutylamino-thiazole-4-carboxylic acid (3-bromo-phenyl)-amide;
5-Isobutylamino-thiazole-4-carboxylic acid (6-methyl-pyridin-2-yl)-amide;
5-Isobutylamino-thiazole-4-carboxylic acid (6-chloro-pyridin-2-yl)-amide;
5-Isobutylamino-thiazole-4-carboxylic acid (6-bromo-pyridin-2-yl)-amide;
5-tert-Butylamino-thiazole-4-carboxylic acid (3-chloro-phenyl)-amide;
5-tert-Butylamino-thiazole-4-carboxylic acid (3-fluoro-phenyl)-amide;
5-tert-Butylamino-thiazole-4-carboxylic acid m-tolylamide;
5-tert-Butylamino-thiazole-4-carboxylic acid (3-bromo-phenyl)-amide;
5-Isopropylamino-thiazole-4-carboxylic acid m-tolylamide;
5-Isopropylamino-thiazole-4-carboxylic acid (6-bromo-pyridin-2-yl)-amide;
5-Isopropylamino-thiazole-4-carboxylic acid (4-methyl-thiazol-2-yl)-amide;
5-(1,1-Dimethyl-propylamino)-thiazole-4-carboxylic acid (3-chloro-phenyl)-amide;
5-(1,1-Dimethyl-propylamino)-thiazole-4-carboxylic acid m-tolylamide;
5-(1,1-Dimethyl-propylamino)-thiazole-4-carboxylic acid (6-methyl-pyridin-2-yl)-amide;
5-(1,1-Dimethyl-propylamino)-thiazole-4-carboxylic acid (4-methyl-thiazol-2-yl)-amide;
5-Ethylamino-thiazole-4-carboxylic acid m-tolylamide;
5-Ethylamino-thiazole-4-carboxylic acid (6-bromo-pyridin-2-yl)-amide;
5-Ethylamino-thiazole-4-carboxylic acid (4-methyl-thiazol-2-yl)-amide;
5-Dimethylamino-2-methyl-thiazole-4-carboxylic acid (6-methyl-pyridin-2-yl)-amide;
2-Methyl-5-methylamino-thiazole-4-carboxylic acid (4-methyl-thiazol-2-yl)-amide; and
5-Dimethylamino-2-methyl-thiazole-4-carboxylic acid (4-methyl-thiazol-2-yl)-amide.

In certain embodiments of the compounds of the invention, $R^3$ is —$(CH_2)_m$—$R^b$, wherein $R^b$ is —O—$C_1$-$C_7$-alkyl, $C_3$-$C_6$-cycloalkyl, 5 or 6 membered heterocycloalkyl, aryl optionally substituted by fluoro, or heteroaryl optionally substituted by $C_1$-$C_7$-alkyl for example the following compounds:
5-(3-Methoxy-propylamino)-thiazole-4-carboxylic acid (3-chloro-phenyl)-amide;
5-(3-Methoxy-propylamino)-thiazole-4-carboxylic acid m-tolylamide;
5-(3-Methoxy-propylamino)-thiazole-4-carboxylic acid (3-bromo-phenyl)-amide;
5-Benzylamino-thiazole-4-carboxylic acid (6-methyl-pyridin-2-yl)-amide;
5-Benzylamino-thiazole-4-carboxylic acid (3-chloro-phenyl)-amide;
5-((Cyclopropylmethyl)-amino)-2-methyl-thiazole-4-carboxylic acid (2-methyl-pyrimidin-4-yl)-amide;
5-((Cyclopropylmethyl)-amino)-2-methyl-thiazole-4-carboxylic acid (2-chloro-pyridin-4-yl)-amide;
2-Methyl-5-[(tetrahydro-pyran-4-ylmethyl)-amino]-thiazole-4-carboxylic acid (2-methyl-pyridin-4-yl)-amide;
5-(3,5-Difluoro-benzylamino)-2-methyl-thiazole-4-carboxylic acid (2-methyl-pyridin-4-yl)-amide
2-Methyl-5-[(pyridin-2-ylmethyl)-amino]-thiazole-4-carboxylic acid (2-methyl-pyridin-4-yl)-amide;
2-Methyl-5-[(3-methyl-3H-imidazol-4-ylmethyl)-amino]-thiazole-4-carboxylic acid (2-methyl-pyridin-4-yl)-amide;
5-(Cyclopropylmethyl-amino)-2-methyl-thiazole-4-carboxylic acid (1-methyl-1H-pyrazol-3-yl)-amide;

5-(Cyclopropylmethyl-amino)-2-methyl-thiazole-4-carboxylic acid (4-methyl-thiazol-2-yl)-amide;
2-Methyl-5-[(pyridin-3-ylmethyl)-amino]-thiazole-4-carboxylic acid (4-methyl-thiazol-2-yl)-amide;
5-(3,5-Difluoro-benzylamino)-2-methyl-thiazole-4-carboxylic acid (4-methyl-thiazol-2-yl)-amide; and
5-(2-Methoxy-ethylamino)-2-methyl-thiazole-4-carboxylic acid (2-methyl-pyridin-4-yl)-amide.

In certain embodiments of the compounds of the invention $R^3$ is —(CO)—$R^c$, wherein $R^c$ is —O—$(CH_2)_m$—$C_3$-$C_6$-cycloalkyl, or aryl; for example the following compounds:
5-Benzoylamino-2-methyl-thiazole-4-carboxylic acid (3-chloro-phenyl)-amide; and
Cyclopropylmethyl-[2-methyl-4-(2-methyl-pyrimidin-4-yl-carbamoyl)-thiazol-5-yl]-carbamic acid cyclopropylmethyl ester.

In certain embodiments of the compounds of the invention $R^3$ is $C_3$-$C_6$-cycloalkyl; for example the following compounds:
5-Cyclopropylamino-thiazole-4-carboxylic acid (3-chloro-phenyl)-amide;
5-Cyclopropylamino-thiazole-4-carboxylic acid (3-fluoro-phenyl)-amide;
5-Cyclopropylamino-thiazole-4-carboxylic acid phenylamide;
5-Cyclopropylamino-thiazole-4-carboxylic acid m-tolylamide;
5-Cyclopropylamino-thiazole-4-carboxylic acid (3-bromo-phenyl)-amide;
5-Cyclohexylamino-thiazole-4-carboxylic acid (3-chloro-phenyl)-amide;
5-Cyclopentylamino-thiazole-4-carboxylic acid (3-chloro-phenyl)-amide;
5-Cyclopentylamino-thiazole-4-carboxylic acid (3-fluoro-phenyl)-amide;
5-Cyclopentylamino-thiazole-4-carboxylic acid phenylamide;
5-Cyclopentylamino-thiazole-4-carboxylic acid m-tolylamide;
5-Cyclopentylamino-thiazole-4-carboxylic acid (3-bromo-phenyl)-amide;
5-Cyclopentylamino-thiazole-4-carboxylic acid (6-methyl-pyridin-2-yl)-amide;
5-Cyclopentylamino-thiazole-4-carboxylic acid (6-chloro-pyridin-2-yl)-amide;
5-Cyclopentylamino-thiazole-4-carboxylic acid (6-bromo-pyridin-2-yl)-amide; and
5-Cyclopropylamino-2-methyl-thiazole-4-carboxylic acid (2-methyl-pyridin-4-yl)-amide.

In particular, in certain embodiments of the compounds of the invention, $R^3$ is cyclopropyl or cyclohexyl.

In certain embodiments of the compounds of the invention, $R^4$ is hydrogen.

In certain embodiments of the compounds of the invention, $R^1$ is aryl, optionally substituted by one or more substituents selected from the group consisting of —OH, chloro, fluoro, bromo, cyano, $C_1$-$C_7$-alkyl, $C_1$-$C_7$-alkoxy, —O—(CO)—$C_1$-$C_7$-alkyl, $C_3$-$C_6$-cycloalkyl, and —$(CH_2)_m$—$R^a$, wherein $R^a$ is —OH, —$CH_2F$, —$CHF_2$, —$CF_3$, $C_1$-$C_7$-alkoxy, $C_3$-$C_6$-cycloalkyl, —NH(CO)—$C_1$-$C_7$-alkyl, or —O—(CO)—$C_1$-$C_7$-alkyl;

In certain embodiments of the compounds of the invention, $R^1$ is heteroaryl, optionally substituted by one or more substituents selected from the group consisting of —OH, chloro, fluoro, bromo, cyano, $C_1$-$C_7$-alkyl, $C_1$-$C_7$-alkoxy, —O—(CO)—$C_1$-$C_7$-alkyl, $C_3$-$C_6$-cycloalkyl, and —$(CH_2)_m$—$R^a$, wherein $R^a$ is —OH, —$CH_2F$, —$CHF_2$, —$CF_3$, $C_1$-$C_7$-alkoxy, $C_3$-$C_6$-cycloalkyl, —NH(CO)—$C_1$-$C_7$-alkyl, or —O—(CO)—$C_1$-$C_7$-alkyl;

In certain embodiments of the compounds of the invention, $R^2$ is hydrogen. In certain other embodiments of the compounds of the invention, $R^2$ is $C_1$-$C_7$-alkyl, in particular compounds in which $R^2$ is methyl.

In all the above recited embodiments, alone or in combination, heteroaryls can be 5 or 6 membered heteroaryl group.

In certain embodiments of the invention, the compounds of the invention of formula (I) wherein $R^2$ and $R^4$ are H can be prepared according to a method comprising the steps of:

a) either reacting the compound of formula (4):

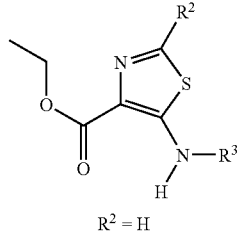

4

b) with a compound of formula (24):

$R^1$—$NH_2$ c) or hydrolyze the compound of formula (4) into a compound of formula (5):

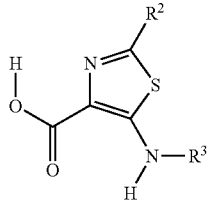

5

and subsequently reacting the compound of formula (5) with a compound of formula (24):

$R^1$—$NH_2$ to obtain the compound of formula (I) wherein $R^2$ and $R^4$ are H and $R^1$ and $R^3$ are as defined hereinabove.

This embodiment is further illustrated in schemes 1 and 2 hereinbelow.

In certain embodiments of the invention, the compounds of the invention of formula (I) wherein $R^2$ is $C_1$-$C_7$-alkyl, —$(CH_2)_m$—O—$C_1$-$C_7$-alkyl or $C_3$-$C_6$-cycloalkyl and $R^4$ is H can be prepared according to a method comprising the steps of:

a) reacting a compound of formula (11)

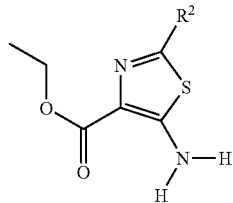

11

with a compound of the formula (25):

X—$R^3$ wherein X is halo, preferably Br or Cl, and R³ is as defined above to obtain a compound of formula (4):

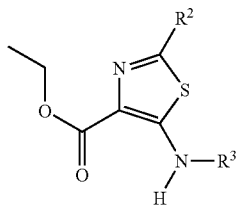

4 b) either reacting the compound of formula (4) with a compound of formula (24):

c) or hydrolyze the compound of formula (4) into a compound of formula (5):

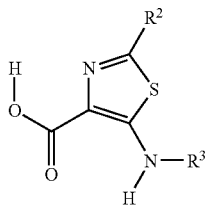

5 and subsequently reacting the compound of formula (5) with a compound of the formula (24):

to obtain the compound of formula (I) wherein R² is $C_1$-$C_7$-alkyl, —(CH$_2$)$_m$—O—$C_1$-$C_7$-alkyl or $C_3$-$C_6$-cycloalkyl, R⁴ is H and R¹ and R³ are as defined hereinabove.

This embodiment is further illustrated in schemes 2, 3 and 8 hereinbelow.

In certain embodiments of the invention, the compounds of the invention of formula (I) wherein R² is methyl and R⁴ is H or is as defined hereinabove, can be prepared according to a method comprising the steps of:

a) reacting a compound of formula (14):

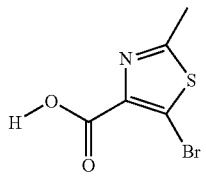

14 with a compound of formula (24):

to obtain a compound of formula (15):

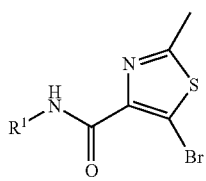

15 and reacting the compound of formula (15)

b) either with a compound of formula (2):

5 to obtain the compound of formula I, wherein R² is methyl, R⁴ is H and R¹ and R³ are as defined hereinabove;

c) or with a compound of formula (26):

10 obtain the compound of formula I, wherein R² is methyl and R¹, R³ and R⁴ are as defined hereinabove.

This embodiment is further illustrated in scheme 4 hereinbelow.

In certain embodiments of the invention, the compounds of the invention of formula (I) wherein R² is methyl and R⁴ is H can be prepared according to a method comprising the steps of:

a) either reacting a compound of formula (18):

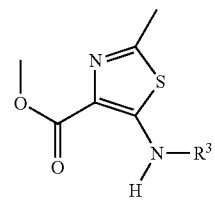

18 with a compound of formula (24):

b) or hydrolyze the compound of formula (18) into a compound of formula (5):

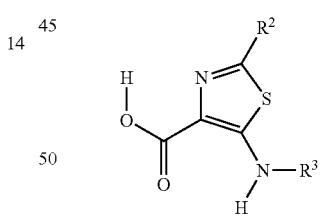

5 and subsequently reacting the compound of formula (5) with a compound of formula (24):

to obtain the compound of formula (I) wherein R² is methyl, R⁴ is H and R¹ and R³ are as defined hereinabove.

This embodiment is further illustrated in scheme 5 hereinbelow.

In certain embodiments of the invention, the compounds of the invention of formula (I) wherein R⁴ is H can be prepared according to a method comprising the steps of:

a) protecting the amino moiety of a compound of formula (11):

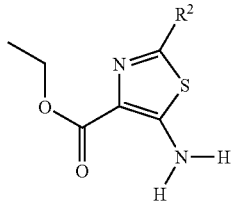

11 with a suitable amino-protective group and subsequently reacting the resulting amino-protected compound with a compound of formula (24):

R¹NH₂ and then deprotecting the amino moiety and reacting the resulting amino-deprotected compound with a compound of the following formula (25):

X—R³ wherein X is halo, preferably Br or Cl, to obtain the compound of formula (I), wherein $R^4$ is H and $R^1$, $R^2$ and $R^3$ are as defined hereinabove.

This embodiment is further illustrated in schemes 6 and 9 hereinbelow.

In certain embodiments of the invention, the compounds of the invention of formula (I) wherein $R^2$ is methyl and $R^4$ is H can be prepared according to a method comprising the steps of:

a) reacting a compound of formula (17):

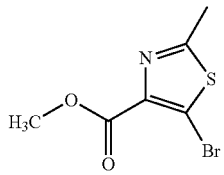

17 with a compound of formula (24):

R¹NH₂ to obtain a compound of formula (15):

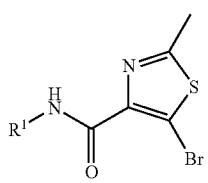

15 b) and reacting the compound of formula (15) with a compound of the following formula (2):

R³NH₂ to obtain the compound of formula (I) wherein $R^2$ is methyl, $R^4$ is H and $R^1$ and $R^3$ are as defined hereinabove.

This embodiment is further illustrated in scheme 7 hereinafter.

In certain embodiments of the invention, the compounds of the invention of formula (I), wherein $R^3$ is $CH_2$—$R^b$ and $R^4$ is H can be prepared according to a method comprising the steps of:

a) reacting a compound of formula (11):

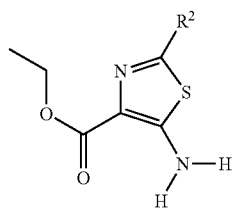

11 with a compound of formula (27):

R^bCHO to obtain a compound of formula (22):

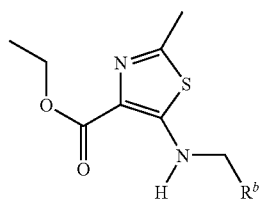

22 b) and reacting the compound of formula (22) with a compound of formula (24):

R¹NH₂ to obtain the compound of formula (I) wherein $R^3$ is $CH_2$—$R^b$, $R^4$ is H and $R^1$ and $R^3$ are as defined in claim 1.

This embodiment is further illustrated in scheme 10 hereinbelow.

The following schemes 1 to 10 further illustrate the various methods of preparation of the compounds of the invention. Unless otherwise specified all starting products and intermediates are commercially available.

Scheme 1:

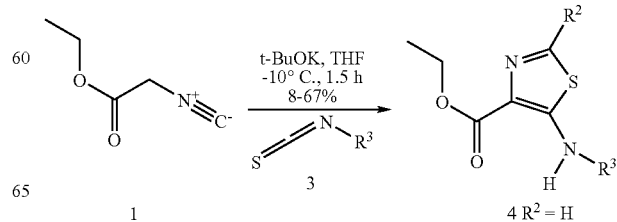

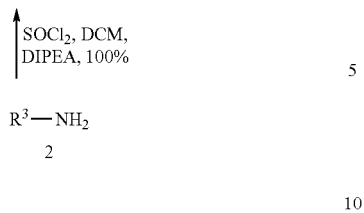

Scheme 1

Compounds of general formula I, where R²=H can be prepared according to schemes 1 and 2 and methods described in the literature (Suzuki, M.; Moriya, T.; Matsumoto, K.; Miyoshi, M. *Synthesis* 1982, 874.) This involves reacting the anion of ethyl isocyanoacetate 1, generated for example by reaction with potassium tert-butylate in tetrahydrofurane at −10° C., with a generic isothiocyanate 3 to afford the corresponding N-substituted-5-amino-1,3-thiazole-4-carboxylic acid ethyl ester 4 (R²=H). Non-commercially available isothiocyanates 3 can be prepared by reaction of a generic amine 2 with thiophosgene and diisopropyl ethyl amine.

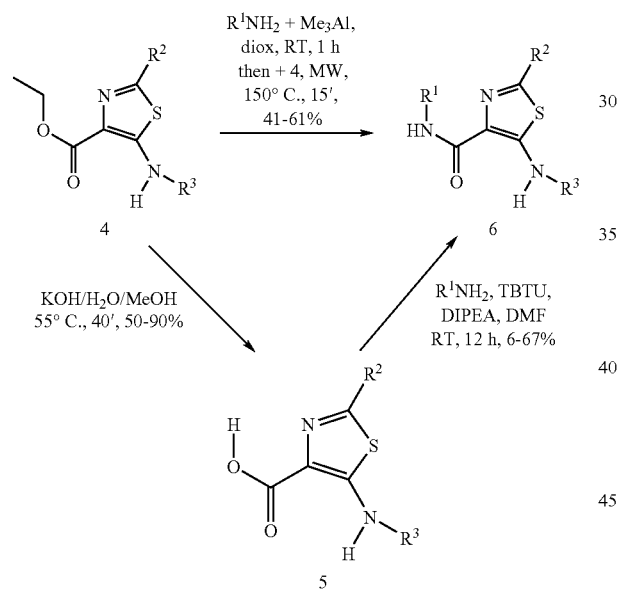

Scheme 2

Conversion of the esters 4 to the desired final products 6 can be accomplished by a variety of known methods. As described in scheme 2, for example, the esters 4 can be hydrolyzed to the corresponding acids 5 by the action of an aqueous base, and these reacted with an amine R¹NH₂ in the presence of a condensing agent such as O-(benzotriazol-1-yl)-N,N,N′,N′-tetramethyluronium tetrafluoborate (TBTU), or converted to the corresponding acyl chlorides by the action of e.g. thionyl chloride or oxalyl chloride and then reacted with the generic amine in the presence of a base. Alternatively, the esters 4 can be heated directly with the aluminium salt of the desired amine (Basha, A.; Lipton, M.; Weinreb, S. M. *Tetrahedron Lett.* 1977, 18, 4171), which can be formed by reaction of the amine with trimethylaluminium. The reaction can be made more efficient by irradiation at 150° C. in a microwave oven.

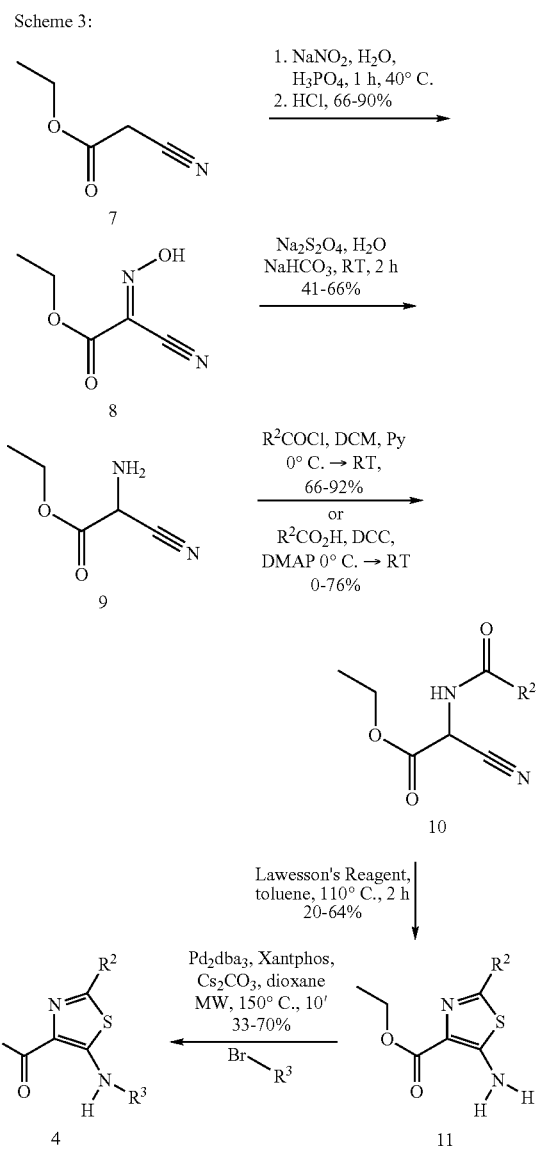

Scheme 3

Compounds of general formula I, where R² is not H can be prepared according to scheme 3 and 2 and methods described in the literature. By treatment of a suitably substituted acylamino-cyanoacetic acid ethyl ester 10 with 2,4-bis(4-methoxyphenyl)-1,3,2,4-dithiadiphosphetane 2,4-disulfide (Lawesson's reagent), cyclization to the corresponding 2-substituted-5-aminothiazole-4-carboxylic acid ethyl ester 11 is obtained (Golankiewicz, B.; Januszczyk, P.; Gdaniec, M.; Kosturkiewicz, Z. *Tetrahedron* 1985, 41, 5989). Acylamino-cyanoacetic acid ethyl ester 10 can be prepared by several known methods, for example by reacting aminocyanacetic acid ethyl ester 9 with an acyl chloride in the presence of a suitable base or with an acid in the presence of a coupling agent, as TBTU. Aminocyanacetic acid ethyl ester 9 is accessed by conversion of cyanacetic acid ethyl ester 7 to cyano-hydroxyimino-acetic acid ethyl ester 8, followed by reduction of the oxime with sodium dithionite. In the particular case where R²=methyl, the commercially available acetylamino-cyanacetic acid ethyl ester (10, R²=Me) can be used.

2-Substituted-5-aminothiazole-4-carboxylic acid ethyl ester 11 can then be converted to compounds of type 4 by coupling with an aryl or alkyl halide, for example by coupling with an aryl bromide under standard palladium catalyzed N—C coupling conditions, such as using palladium dibenzylideneacetone (Pd$_2$dba$_3$) and 4,5-bis(diphenylphosphino)-9,9-dimethylxanthene (Xantphos) with cesium carbonate in dioxane. The efficiency of the reaction can be improved by irradiating in a microwave oven at 150° C. The esters 4 can then be transformed into the target compounds by one of the methods illustrated in scheme 2.

Alternatively, compounds of general formula I, where R$^2$ is methyl can be prepared starting from the commercially available 2-methyl-thiazole-4-carboxylic acid ethyl ester 12 as described in scheme 4. After conversion to the corresponding 2-methyl-thiazole-4-carboxylic acid 13 by aqueous hydrolysis, this is doubly deprotonated by the action of a strong base, as for example butyl lithium. The dianion is then reacted with molecular bromine, to generate 5-bromo-2-methyl-thiazole-4-carboxylic acid 14. Coupling of the latter with a generic amine R$^1$NH$_2$ according to one of the standard methods described above, yields the corresponding 5-bromo-2-methyl thiazole-carboxylic acid amide 15. This can then be converted to the target compounds 6 (R$^2$=Me) by coupling with an aryl or alkyl amine, for example by coupling with an aryl amine under standard palladium catalyzed N—C coupling conditions, as using Pd$_2$dba$_3$ and Xantphos with cesium carbonate in dioxane. The efficiency of the reaction can be improved by irradiating in a microwave oven at 150° C.

Compounds of general formula I, where R$^2$ is methyl and R$^4$ is not H 16 can be obtained analogously by reaction of the bromides 15 with a suitable secondary amine, as illustrated in scheme 4.

Scheme 4:

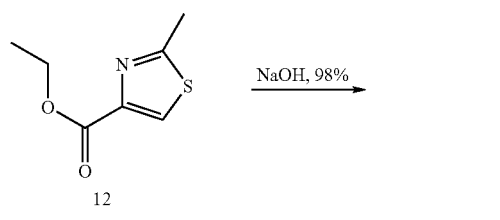

12

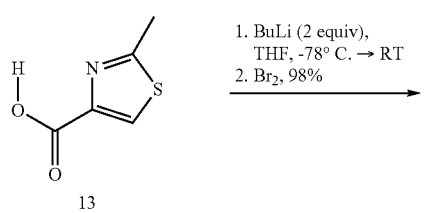

13

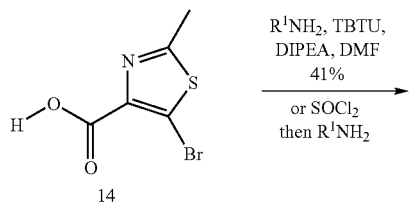

14

-continued

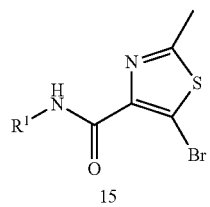

15

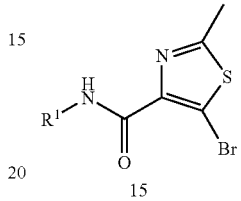

15

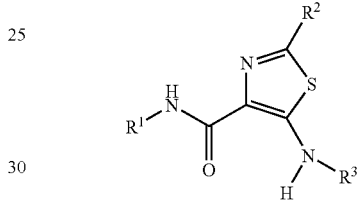

6, R$^2$ = Me

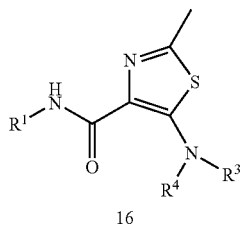

16

Scheme 4

For purposes of efficient application of parallel synthetic methods, 5-bromo-2-methyl-thiazole-4-carboxylic acid 14 can be esterified with an alcohol, for example methanol, to 5-bromo-2-methyl-thiazole-4-carboxylic acid methyl ester 17 (scheme 5), which can be employed as reactant in palladium catalyzed C—N coupling reactions as described above, to yield 5-amino-2-methyl-thiazole-4-carboxylic acid methyl esters 18. These can be processed in analogy to ethyl esters 4, as described in scheme 2.

Scheme 5:

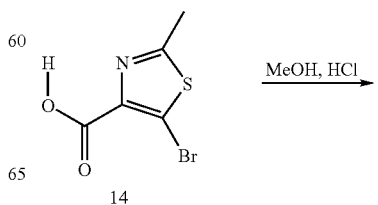

14

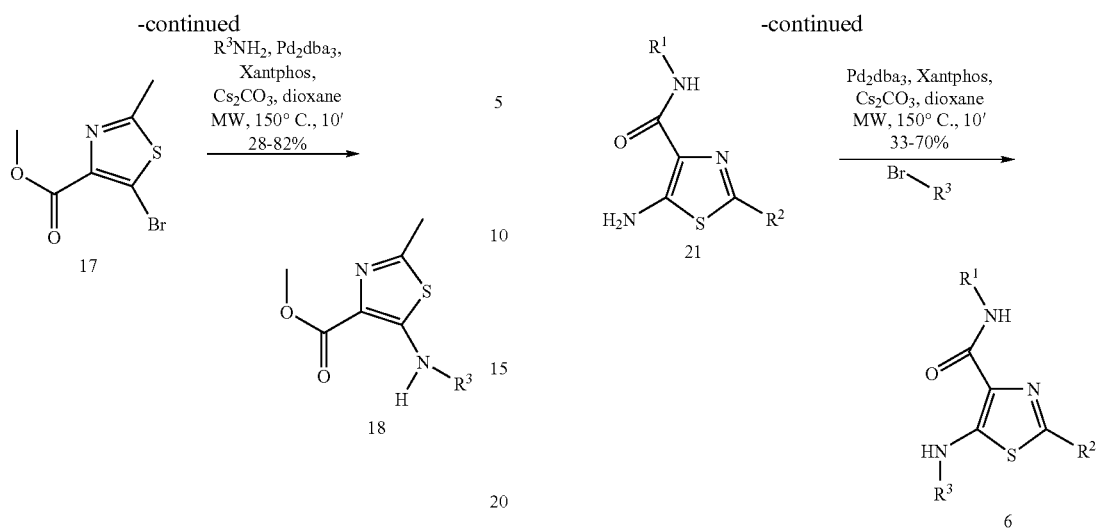

Scheme 5

For purposes of efficient application of parallel synthetic methods, the synthetic protocol illustrated in schemes 2 and 3 can also be inverted, as illustrated in scheme 6.

Scheme 6:

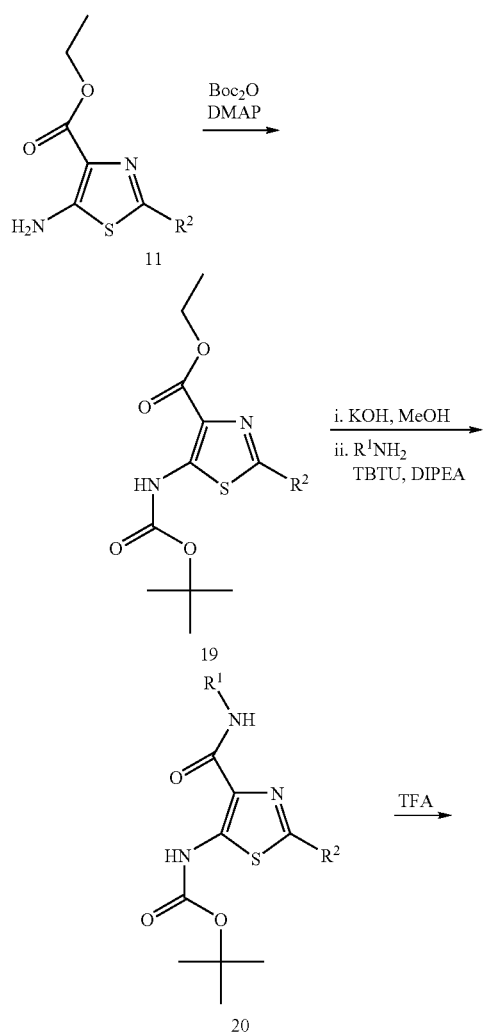

Scheme 6

After protecting the amino group of 2-substituted-5-aminothiazole-4-carboxylic acid ethyl ester 11 with a suitable protective group, for example with tert-butoxycarbonyl, the ester group is hydrolyzed and subjected to coupling with the desired amine according to any of the conditions described above in reference to scheme 2. The corresponding N-protected 2-substituted-5-aminothiazole-4-carboxylic acid amide is then deprotected and employed as reactant in palladium-catalyzed C—N coupling reactions with an aryl halide, as described above, to yield final compounds 6.

Scheme 7:

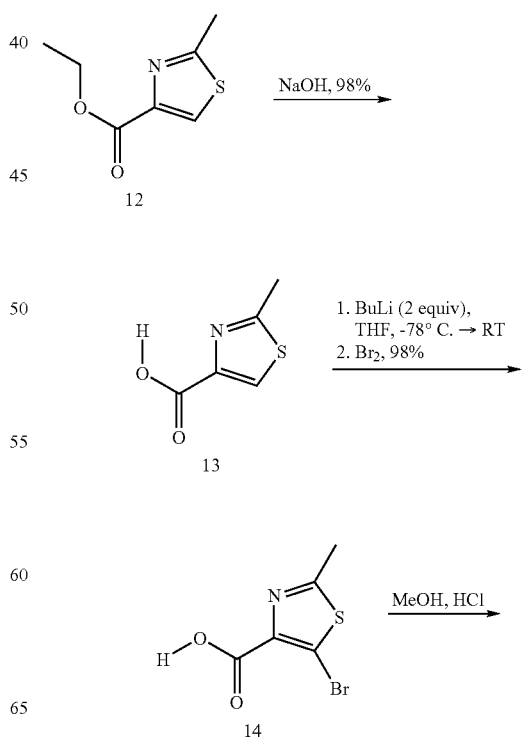

-continued

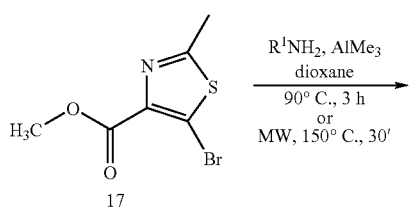

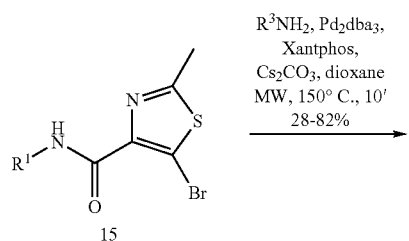

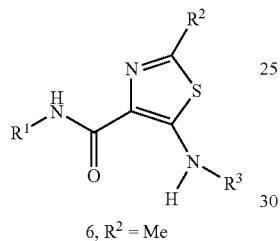

6, R² = Me

-continued

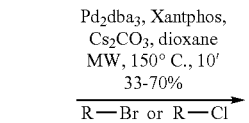

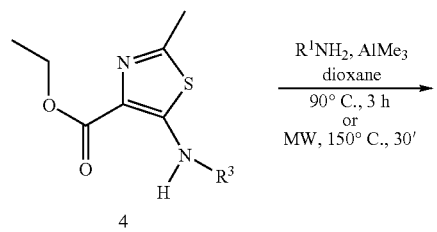

6, R² = Me

Scheme 7

Alternatively, compounds of general formula I, where $R^2$ is methyl can be prepared starting from the commercially available 2-methyl-thiazole-4-carboxylic acid ethyl ester 12 as described in scheme 7. After conversion to the corresponding 2-methyl-thiazole-4-carboxylic acid 13 by aqueous hydrolysis, this is doubly deprotonated by the action of a strong base, as for example butyl lithium. The dianion is then reacted with molecular bromine, to generate 5-bromo-2-methyl-thiazole-4-carboxylic acid 14 which be esterified with an alcohol, for example methanol, to 5-bromo-2-methyl-thiazole-4-carboxylic acid methyl ester 17. The esters 17 can be heated directly with the aluminium salt of the desired amine, (Basha, A.; Lipton, M.; Weinreb, S. M. *Tetrahedron Lett.* 1977, 18, 4171) to yield amide 15. The reaction can be made more efficient by irradiation at 150° C. in a microwave oven. Amide 15 can be employed as reactant in palladium catalyzed C—N coupling reactions as described above.

Scheme 8:

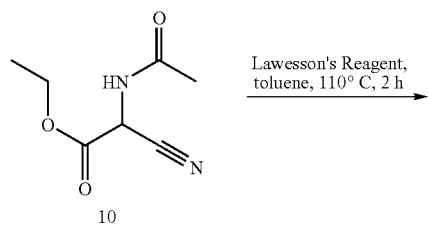

Scheme 8

Alternatively, compounds of general formula I where $R^3$ is methyl can be prepared by the sequence shown in scheme 8. The single steps have been described in detail hereinabove.

Scheme 9:

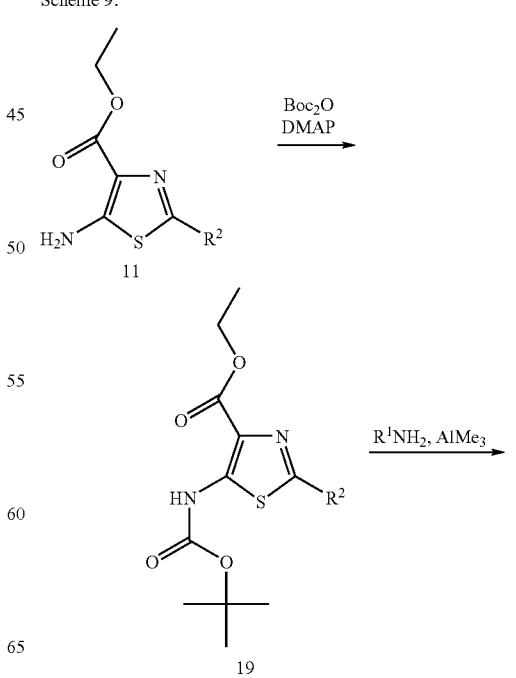

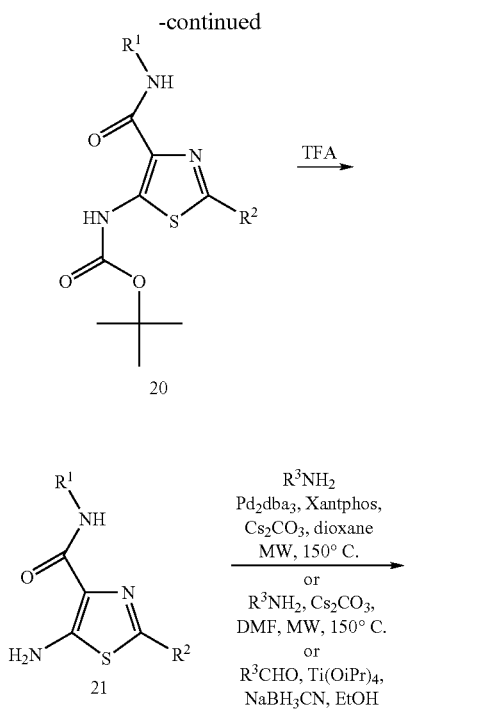

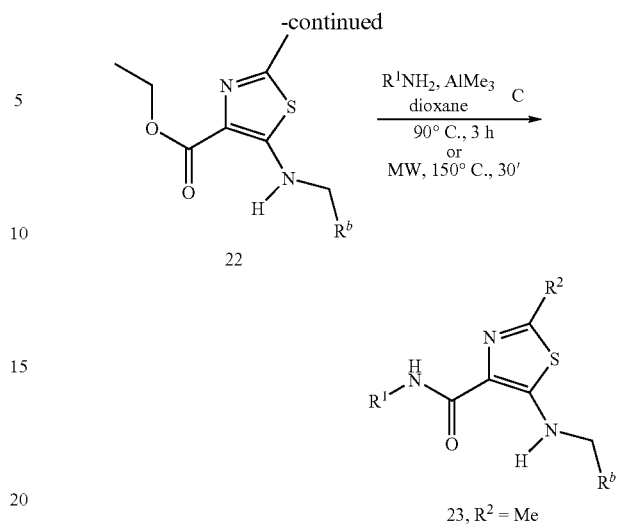

Scheme 10

Compounds of the general formula 23 can be prepared from the already known intermediate 11 as described in scheme 10. Compound 11 is reductively aminated using an aldehyde, tetraisopropyl-orthotitanate and sodium cyanoborohydride to obtain compound 22 which is converted to amide 23 as described hereinabove.

Pharmaceutically acceptable salts of compounds of formula I can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts are, as already mentioned above, metabotropic glutamate receptor antagonists and can be used for the treatment or prevention of mGluR5 receptor mediated disorders, such as acute and/or chronic neurological disorders, cognitive disorders and memory deficits, as well as acute and chronic pain. Treatable neurological disorders are for instance epilepsy, schizophrenia, anxiety, acute, traumatic or chronic degenerative processes of the nervous system, such as Alzheimer's disease, senile dementia, Huntington's chorea, ALS, multiple sclerosis, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, ethanol addiction, nicotine addiction, psychoses, opiate addiction, anxiety, vomiting, dyskinesia and depression. Other treatable indications are restricted brain function caused by bypass operations or transplants, poor blood supply to the brain, spinal cord injuries, head injuries, hypoxia caused by pregnancy, cardiac arrest and hypoglycaemia.

Scheme 9

The synthesis described in scheme 9 is a variation of the synthesis described in scheme 6.

Scheme 10:

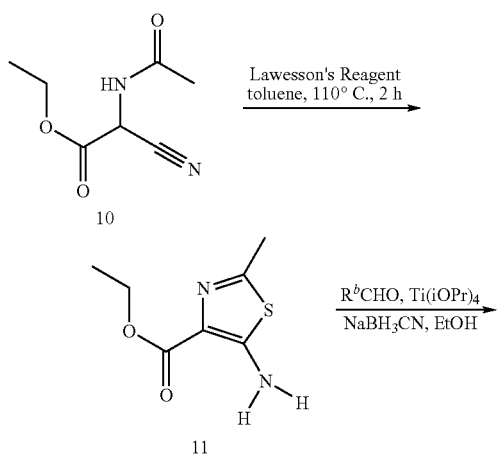

The compounds of formula I and their pharmaceutically acceptable salts are especially useful as analgesics. Treatable kinds of pain include inflammatory pain such as arthritis and rheumatoid disease, vasculitis, neuropathic pain such as trigeminal or herpetic neuralgia, diabetic neuropathy pain, causalgia, hyperalgesia, severe chronic pain, post-operative pain and pain associated with various conditions like cancer, angina, renal or billiay colic, menstruation, migraine and gout.

The pharmacological activity of the compounds was tested using the following method: For binding experiments, cDNA encoding human mGlu 5a receptor was transiently transfected into EBNA cells using a procedure described by Schlaeger and Christensen [Cytotechnology 15:1-13 (1998)]. Cell membrane homogenates were stored at −80° C. until the day of assay where upon they were thawed and resuspended and polytronized in 15 mM Tris-HCl, 120 mM NaCl, 100 mM KCl, 25 mM $CaCl_2$, 25 mM $MgCl_2$ binding buffer at pH 7.4 to a final assay concentration of 20 μg protein/well.

Saturation isotherms were determined by addition of twelve [$^3$H]MPEP concentrations (0.04-100 nM) to these membranes (in a total volume of 200 μl) for 1 h at 4° C. Competition experiments were performed with a fixed concentration of [$^3$H]MPEP (2 nM) and $IC_{50}$ values of test compounds evaluated using 11 concentrations (0.3-10,000 nM). Incubations were performed for 1 h at 4° C.

At the end of the incubation, membranes were filtered onto unifilter (96-well white microplate with bonded GF/C filter preincubated 1 h in 0.1% PEI in wash buffer, Packard BioScience, Meriden, Conn.) with a Filtermate 96 harvester (Packard BioScience) and washed 3 times with cold 50 mM Tris-HCl, pH 7.4 buffer. Nonspecific binding was measured in the presence of 10 μM MPEP. The radioactivity on the filter was counted (3 min) on a Packard Top-count microplate scintillation counter with quenching correction after addition of 45 μl of microscint 40 (Canberra Packard S.A., Zürich, Switzerland) and shaking for 20 min.

For functional assays, [$Ca^{2+}$]i measurements were performed as described previously by Porter et al. [Br. J. Pharmacol. 128:13-20 (1999)] on recombinant human mGlu 5a receptors in HEK-293 cells. The cells were dye loaded using Fluo 4-AM (obtainable by FLUKA, 0.2 μM final concentration). [$Ca^{2+}$]i measurements were performed using a fluorometric imaging plate reader (FLIPR, Molecular Devices Corporation, La Jolla, Calif., USA). Antagonist evaluation was performed following a 5 min preincubation with the test compounds followed by the addition of a submaximal addition of agonist.

The inhibition (antagonists) curves were fitted with a four parameter logistic equation giving $IC_{50}$, and Hill coefficient using iterative non linear curve fitting software (Xcel fit).

For binding experiments the Ki values of the compounds tested are given. The Ki value is defined by the following formula:

$$K_i = IC_{50}/[1+L/K_d]$$

in which the $IC_{50}$ values are those concentrations of the compounds tested which cause 50% inhibition of the competing radioligand ([$^3$H]MPEP). L is the concentration of radioligand used in the binding experiment and the $K_d$ value of the radioligand is empirically determined for each batch of membranes prepared.

The compounds of the present invention are mGluR 5a receptor antagonists. The activities of compounds of formula I as measured in the assay described above are in the range of $K_i$<4 μM and preferably <200 nM.

| Example No. | Ki nM |
| --- | --- |
| 1 | 29 |
| 2 | 124 |
| 13 | 26 |
| 18 | 458 |
| 24 | 127 |
| 74 | 99 |
| 81 | 19 |
| 88 | 18 |
| 145 | 40 |
| 149 | 53 |
| 209 | 40 |

The present invention also provides pharmaceutical compositions containing compounds of the invention, for example compounds of formula I and their pharmaceutically acceptable acid addition salts, and a pharmaceutically acceptable carrier. Such pharmaceutical compositions can be in the form of tablets, coated tablets, dragées, hard and soft gelatine capsules, solutions, emulsions, or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, foe example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Compounds of the formula I are metabotropic glutamate receptor antagonists. The invention provides methods for the treatment of mGluR5 receptor mediated disorders. In particular, the present invention provides a method for treating acute and/or chronic neurological disorders, which comprises administering a therapeutically effective amount of a compound of formula I or a pharmaceutically acceptable salt thereof. The invention also provides a method of treating anxiety, which comprises administering a therapeutically effective amount of a compound of formula I or a pharmaceutically acceptable salt thereof. The invention further provides a method for the treatment of chronic and acute pain, which comprises administering a therapeutically effective amount of a compound of formula I or a pharmaceutically acceptable salt thereof. The invention provides a method for the treatment of urinary incontinence, which comprises administering a therapeutically effective amount of a compound of formula I or a pharmaceutically acceptable salt thereof. The invention also provides a method for the treatment of obesity, which comprises administering a therapeutically effective amount of a compound of formula I or a pharmaceutically acceptable salt thereof.

The invention also provides a method for preparing compositions of the invention which comprises bringing one or more compounds of formula I and/or pharmaceutically acceptable acid addition salts and, if desired, one or more other therapeutically valuable substances into a galenical administration form together with one or more therapeutically inert carriers.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided to further elucidate the invention:

Example 1

5-(Pyridin-3-ylamino)-thiazole-4-carboxylic acid (6-methyl-pyridin-2-yl)-amide

The title compound was prepared as illustrated in schemes 1 and 2.

A) A three-necked flask equipped with a mechanical stirrer, a dropping funnel and an argon inlet was charged with anhydrous tetrahydrofurane (THF) (25.00 ml). Solid potassium tert-butylate (5.46 g, 44.20 mmol) was added and the slurry was stirred until dissolution was complete. The mixture was cooled to −40° C. by means of a dry ice/acetone bath. A solution of isocyano-acetic acid ethyl ester (5.00 g, 44.20 mmol) and 3-isothiocyanato-pyridine (6.02 g, 44.20 mmol) in anhydrous THF (50.00 ml) was added dropwise via the dropping funnel at such a rate that the temperature did not exceed −35° C. and the mixture remained homogeneously stirred (a thick precipitate forms). After addition was complete, the mixture was stirred for further 1 hour letting the temperature free to rise. The reaction was quenched by addition of glacial acetic acid (2.50 ml). The mixture was diluted with THF and ethyl acetate and filtered through celite. The filtrate was evaporated to a dark yellow solid residue, which was purified by flash chromatography (heptane/ethyl acetate) to yield 5-(pyridin-3-ylamino)-thiazole-4-carboxylic acid ethyl ester (4.85 g, 44%) as a light yellow solid, MS (ISP): m/e=250.2 (M+H$^+$).

B) A solution of 5-(pyridin-3-ylamino)-thiazole-4-carboxylic acid ethyl ester (2.90 g, 11.63 mmol) in methanol (24.00 ml) was treated at room temperature with a solution of KOH (1.95 g, 34.90 mmol) in water (18 ml) and stirred at 65° C. for 2 h 45 min. The methanol was evaporated and the residual slurry acidified to pH 5 with 1N HCl. The mixture was sonicated for 15 minutes, then filtered washing with water. The solid was dried under high vacuum overnight, yielding 5-(pyridin-3-ylamino)-thiazole-4-carboxylic acid (2.37 g, 92%) as a white solid.

C) A solution of 5-(pyridin-3-ylamino)-thiazole-4-carboxylic acid (0.50 g, 2.26 mmol) in DMF (5.00 ml) was treated with TBTU (0.94 g, 2.94 mmol) and diisopropyl ethyl amine (DIPEA) (0.58 g, 4.52 mmol). 6-Methyl-pyridin-2-ylamine (0.49 g, 4.52 mmol) was added and the mixture was stirred at room temperature overnight. Precipitation was favored by adding acetonitrile (5.00 ml). The crystalline precipitate was filtered and dried under high vacuum, yielding the title compound in high purity. Evaporation of the mother liquors gave a residue which was purified by flash chromatography (heptane/ethyl acetate) to yield a second batch of title compound as an amorphous solid (total 0.59 g, 84%), MS (ISP): m/e=312.0 (M+H$^+$).

Example 2

5-(Pyridin-3-ylamino)-thiazole-4-carboxylic acid (3-chloro-phenyl)-amide

The title compound, MS (ISP): m/e=331.5 (M+H$^+$), was prepared as for example 1, steps A to C. Step C was performed using 3-chloro aniline.

Example 3

5-(Pyridin-3-ylamino)-thiazole-4-carboxylic acid (6-chloro-pyridin-2-yl)-amide

The title compound, MS (ISP): m/e=332.1 (M+H$^+$), was prepared as for example 1, steps A to C. Step C was performed using 6-chloro-pyridin-2-ylamine Example 4

5-(Pyridin-3-ylamino)-thiazole-4-carboxylic acid (6-bromo-pyridin-2-yl)-amide

The title compound, MS (ISP): m/e=376.0, 378.0 (M+H$^+$), was prepared as for example 1, steps A to C. Step C was performed using 6-bromo-pyridin-2-ylamine Example 5

5-(Pyridin-3-ylamino)-thiazole-4-carboxylic acid (4-methyl-thiazol-2-yl)-amide

The title compound, MS (ISP): m/e=318.1 (M+H$^+$), was prepared as for example 1, steps A to C. Step C was performed using 4-methyl-thiazol-2-ylamine.

Example 6

5-(Pyridin-3-ylamino)-thiazole-4-carboxylic acid (2-methyl-thiazol-4-yl)-amide

The title compound, MS (ISP): m/e=318.1 (M+H$^+$), was prepared as for example 1, steps A to C. Step C was performed using 2-methyl-thiazol-4-ylamine.

Example 7

5-(Pyridin-3-ylamino)-thiazole-4-carboxylic acid m-tolylamide

The title compound, MS (ISP): m/e=310.7 (M+H$^+$), was prepared as for example 1, steps A to C. Step C was performed using m-tolylamine.

Example 8

5-(Pyridin-3-ylamino)-thiazole-4-carboxylic acid (6-ethyl-pyridin-2-yl)-amide

The title compound, MS (ISP): m/e=326.3 (M+H$^+$), was prepared as for example 1, steps A to C. Step C was performed using 6-ethyl-pyridin-2-ylamine.

Example 9

5-(Pyridin-3-ylamino)-thiazole-4-carboxylic acid (6-trifluoromethyl-pyridin-2-yl)-amide The title compound, MS (ISP): m/e=366.3 (M+H$^+$), was prepared as for example 1, steps A to C. Step C was performed using 6-trifluoromethyl-pyridin-2-ylamine.

Example 10

5-Phenylamino-thiazole-4-carboxylic acid phenylamide

The title compound, MS (ISP): m/e=296.1 (M+H$^+$), was prepared as for example 1, steps A to C. Step A was performed using isothiocyanato-benzene and yielded 5-phenylamino-thiazole-4-carboxylic acid ethyl ester. This was hydrolyzed in step B to 5-phenylamino-thiazole-4-carboxylic acid, which was reacted with aniline in step C.

Example 11

5-Phenylamino-thiazole-4-carboxylic acid (3-chloro-phenyl)-amide

The title compound, MS (ISP): m/e=330.1 (M+H$^+$), was prepared as for example 10, steps A to C. Step C was performed using 3-chloro aniline.

Example 12

5-Phenylamino-thiazole-4-carboxylic acid (3-fluoro-phenyl)-amide

The title compound, MS (ISP): m/e=314.1 (M+H$^+$), was prepared as for example 10, steps A to C. Step C was performed using 3-fluoro aniline.

Example 13

5-Phenylamino-thiazole-4-carboxylic acid (6-methyl-pyridin-2-yl)-amide

The title compound, MS (ISP): m/e=311.2 (M+H$^+$), was prepared as for example 10, steps A to C. Step C was performed using 6-methyl-pyridin-2-ylamine.

Example 14

5-Phenylamino-thiazole-4-carboxylic acid (6-chloro-pyridin-2-yl)-amide

The title compound, MS (ISP): m/e=331.1 (M+H$^+$), was prepared as for example 10, steps A to C. Step C was performed using 6-chloro-pyridin-2-ylamine.

Example 15

5-Phenylamino-thiazole-4-carboxylic acid thiazol-2-ylamide

The title compound, MS (ISP): m/e=303.1 (M+H$^+$), was prepared as for example 10, steps A to C. Step C was performed using thiazol-2-ylamine.

Example 16

5-Phenylamino-thiazole-4-carboxylic acid (4-methyl-thiazol-2-yl)-amide

The title compound, MS (ISP): m/e=317.1 (M+H$^+$), was prepared as for example 10, steps A to C. Step C was performed using 4-methyl-thiazol-2-ylamine.

Example 17

5-(3-Chloro-phenylamino)-thiazole-4-carboxylic acid (3-chloro-phenyl)-amide

The title compound, MS (ISP): m/e=364.3 (M+H$^+$), was prepared as for example 1, steps A to C. Step A was performed using 1-chloro-3-isothiocyanato-benzene and yielded 5-(3-chloro-phenylamino)-thiazole-4-carboxylic acid ethyl ester. This was hydrolized in step B to 5-(3-chloro-phenylamino)-thiazole-4-carboxylic acid, which was reacted with 3-chloro aniline in step C.

Example 18

5-Cyclopropylamino-thiazole-4-carboxylic acid (3-chloro-phenyl)-amide

The title compound, MS (ISP): m/e=294.1 (M+H$^+$), was prepared as for example 1, steps A to C. Step A was performed using isothiocyanato-cyclopropane and yielded 5-cyclopropylamino-thiazole-4-carboxylic acid ethyl ester. This was hydrolized in step B to 5-cyclopropylamino-thiazole-4-carboxylic acid, which was reacted with 3-chloro aniline in step C.

Example 19

5-Cyclopropylamino-thiazole-4-carboxylic acid (3-fluoro-phenyl)-amide

The title compound, MS (ISP): m/e=278.1 (M+H$^+$), was prepared as for example 18, steps A to C. Step C was performed using 3-fluoro aniline.

Example 20

5-Cyclopropylamino-thiazole-4-carboxylic acid phenylamide

The title compound, MS (ISP): m/e=260.1 (M+H$^+$), was prepared as for example 18, steps A to C. Step C was performed using aniline.

Example 21

5-Cyclopropylamino-thiazole-4-carboxylic acid m-tolylamide

The title compound, MS (ISP): m/e=274.1 (M+H$^+$), was prepared as for example 18, steps A to C. Step C was performed using m-tolylamine.

Example 22

5-Cyclopropylamino-thiazole-4-carboxylic acid (3-bromo-phenyl)-amide

The title compound, MS (ISP): m/e=317.1 (M+H$^+$), was prepared as for example 18, steps A to C. Step C was performed using 3-bromo aniline.

Example 23

5-Cyclohexylamino-thiazole-4-carboxylic acid (3-chloro-phenyl)-amide

The title compound, MS (ISP): m/e=336.1 (M+H$^+$), was prepared as for example 1, steps A to C. Step A was performed using isothiocyanato-cyclohexane and yielded 5-cyclohexylamino-thiazole-4-carboxylic acid ethyl ester. This was hydrolized in step B to 5-cyclohexylamino-thiazole-4-carboxylic acid, which was reacted with 3-chloro aniline in step C.

Example 24

5-Methylamino-thiazole-4-carboxylic acid (3-chloro-phenyl)-amide

The title compound, MS (ISP): m/e=268.1 (M+H$^+$), was prepared as for example 1, steps A to C. Step A was performed using isothiocyanatomethane and yielded 5-methylamino-thiazole-4-carboxylic acid ethyl ester. This was hydrolized in step B to 5-methylamino-thiazole-4-carboxylic acid, which was reacted with 3-chloro aniline in step C.

Example 25

5-Methylamino-thiazole-4-carboxylic acid (3-fluoro-phenyl)-amide

The title compound, MS (ISP): m/e=252.1 (M+H$^+$), was prepared as for example 24, steps A to C. Step C was performed using 3-fluoro aniline.

Example 26

5-Methylamino-thiazole-4-carboxylic acid phenylamide

The title compound, MS (ISP): m/e=234.2 (M+H$^+$), was prepared as for example 24, steps A to C. Step C was performed using aniline.

Example 27

5-Methylamino-thiazole-4-carboxylic acid m-tolylamide

The title compound, MS (ISP): m/e=248.2 (M+H$^+$), was prepared as for example 24, steps A to C. Step C was performed using m-tolylamine.

Example 28

5-Methylamino-thiazole-4-carboxylic acid (3-bromo-phenyl)-amide

The title compound, MS (ISP): m/e=314.1 (M+H$^+$), was prepared as for example 24, steps A to C. Step C was performed using 3-bromo aniline.

Example 29

5-Methylamino-thiazole-4-carboxylic acid (6-chloro-pyridin-2-yl)-amide

The title compound, MS (ISP): m/e=268.7 (M+H$^+$), was prepared as for example 24, steps A to C. Step C was performed using 6-chloro-pyridin-2-ylamine.

Example 30

5-Methylamino-thiazole-4-carboxylic acid (6-bromo-pyridin-2-yl)-amide

The title compound, MS (ISP): m/e=313.0, 315.0 (M+H$^+$), was prepared as for example 24, steps A to C. Step C was performed using 6-bromo-pyridin-2-ylamine.

Example 31

5-Methylamino-thiazole-4-carboxylic acid (6-methyl-pyridin-2-yl)-amide

The title compound, MS (ISP): m/e=249.1 (M+H$^+$), was prepared as for example 24, steps A to C. Step C was performed using 6-methyl-pyridin-2-ylamine.

Example 32

5-Cyclopentylamino-thiazole-4-carboxylic acid (3-chloro-phenyl)-amide

The title compound, MS (ISP): m/e=322.1 (M+H$^+$), was prepared as for example 1, steps A to C. Step A was performed using isothiocyanato-cyclopentane and yielded 5-cyclopentylamino-thiazole-4-carboxylic acid ethyl ester. This was hydrolized in step B to 5-cyclopentylamino-thiazole-4-carboxylic acid, which was reacted with 3-chloro aniline in step C.

Example 33

5-Cyclopentylamino-thiazole-4-carboxylic acid (3-fluoro-phenyl)-amide

The title compound, MS (ISP): m/e=306.1 (M+H$^+$), was prepared as for example 32, steps A to C. Step C was performed using 3-fluoro aniline.

Example 34

5-Cyclopentylamino-thiazole-4-carboxylic acid phenylamide

The title compound, MS (ISP): m/e=288.1 (M+H$^+$), was prepared as for example 32, steps A to C. Step C was performed using aniline.

Example 35

5-Cyclopentylamino-thiazole-4-carboxylic acid m-tolylamide

The title compound, MS (ISP): m/e=302.2 (M+H$^+$), was prepared as for example 32, steps A to C. Step C was performed using m-tolylamine.

Example 36

5-Cyclopentylamino-thiazole-4-carboxylic acid (3-bromo-phenyl)-amide

The title compound, MS (ISP): m/e=366.0 (M+H$^+$), was prepared as for example 32, steps A to C. Step C was performed using 3-bromo aniline.

Example 37

5-Cyclopentylamino-thiazole-4-carboxylic acid (6-methyl-pyridin-2-yl)-amide

The tide compound, MS (ISP): m/e=303.2 (M+H$^+$), was prepared as for example 32, steps A to C. Step C was performed using 6-methyl-pyridin-2-ylamine.

Example 38

5-Cyclopentylamino-thiazole-4-carboxylic acid (6-chloro-pyridin-2-yl)-amide

The title compound, MS (ISP): m/e=323.1 (M+H$^+$), was prepared as for example 32, steps A to C. Step C was performed using 6-chloro-pyridin-2-ylamine.

Example 39

5-Cyclopentylamino-thiazole-4-carboxylic acid (6-bromo-pyridin-2-yl)-amide

The title compound, MS (ISP): m/e=367.0 (M+H$^+$), was prepared as for example 32, steps A to C. Step C was performed using 6-bromo-pyridin-2-ylamine.

Example 40

5-Isobutylamino-thiazole-4-carboxylic acid (3-chloro-phenyl)-amide

The title compound, MS (ISP): m/e=310.2 (M+H$^+$), was prepared as for example 1, steps A to C. Step A was performed using 1-isothiocyanato-2-methyl-propane and yielded 5-isobutylamino-thiazole-4-carboxylic acid ethyl ester. This was hydrolized in step B to 5-isobutylamino-thiazole-4-carboxylic acid, which was reacted with 3-chloro aniline in step C.

Example 41

5-Isobutylamino-thiazole-4-carboxylic acid (3-fluoro-phenyl)-amide

The title compound, MS (ISP): m/e=294.1 (M+H$^+$), was prepared as for example 40, steps A to C. Step C was performed using 3-fluoro aniline.

Example 42

5-Isobutylamino-thiazole-4-carboxylic acid phenylamide

The title compound, MS (ISP): m/e=276.1 (M+H$^+$), was prepared as for example 40, steps A to C. Step C was performed using aniline.

Example 43

5-Isobutylamino-thiazole-4-carboxylic acid m-tolylamide

The title compound, MS (ISP): m/e=290.1 (M+H$^+$), was prepared as for example 40, steps A to C. Step C was performed using m-tolylamine.

Example 44

5-Isobutylamino-thiazole-4-carboxylic acid (3-bromo-phenyl)-amide

The title compound, MS (ISP): m/e=356.1 (M+H$^+$), was prepared as for example 40, steps A to C. Step C was performed using 3-bromo aniline.

Example 45

5-Isobutylamino-thiazole-4-carboxylic acid (6-methyl-pyridin-2-yl)-amide

The title compound, MS (ISP): m/e=291.1 (M+H$^+$), was prepared as for example 40, steps A to C. Step C was performed using 6-methyl-pyridin-2-ylamine.

Example 46

5-Isobutylamino-thiazole-4-carboxylic acid (6-chloro-pyridin-2-yl)-amide

The title compound, MS (ISP): m/e=311.1 (M+H$^+$), was prepared as for example 40, steps A to C. Step C was performed using 6-chloro-pyridin-2-ylamine.

Example 47

5-Isobutylamino-thiazole-4-carboxylic acid (6-bromo-pyridin-2-yl)-amide

The title compound, MS (ISP): m/e=355.0, 357.0 (M+H$^+$), was prepared as for example 40, steps A to C. Step C was performed using 6-bromo-pyridin-2-ylamine.

Example 48

5-tert-Butylamino-thiazole-4-carboxylic acid (3-chloro-phenyl)-amide

The title compound, MS (ISP): m/e=310.2 (M+H$^+$), was prepared as for example 1, steps A to C. Step A was performed using 2-isothiocyanato-2-methyl-propane and yielded 5-tert-butylamino-thiazole-4-carboxylic acid ethyl ester. This was hydrolized in step B to 5-tert-butylamino-thiazole-4-carboxylic acid, which was reacted with 3-chloro aniline in step C.

Example 49

5-tert-Butylamino-thiazole-4-carboxylic acid (3-fluoro-phenyl)-amide

The title compound, MS (ISP): m/e=294.0 (M+H$^+$), was prepared as for example 48, steps A to C. Step C was performed using 3-fluoro aniline.

Example 50

5-tert-Butylamino-thiazole-4-carboxylic acid
m-tolylamide

The title compound, MS (ISP): m/e=290.1 (M+H$^+$), was prepared as for example 48, steps A to C. Step C was performed using m-tolylamine.

Example 51

5-tert-Butylamino-thiazole-4-carboxylic acid
(3-bromo-phenyl)-amide

The title compound, MS (ISP): m/e=356.1 (M+H$^+$), was prepared as for example 48, steps A to C. Step C was performed using 3-bromo aniline.

Example 52

5-(3-Methoxy-propylamino)-thiazole-4-carboxylic
acid (3-chloro-phenyl)-amide

The title compound, MS (ISP): m/e=326.1 (M+H$^+$), was prepared as for example 1, steps A to C. Step A was performed using 1-isothiocyanato-3-methoxy-propane and yielded 5-(3-methoxy-propylamino)-thiazole-4-carboxylic acid ethyl ester. This was hydrolized in step B to 5-(3-methoxy-propylamino)-thiazole-4-carboxylic acid, which was reacted with 3-chloro aniline in step C.

Example 53

5-(3-Methoxy-propylamino)-thiazole-4-carboxylic
acid m-tolylamide

The title compound, MS (ISP): m/e=306.1 (M+H$^+$), was prepared as for example 52, steps A to C. Step C was performed using m-tolylamine.

Example 54

5-(3-Methoxy-propylamino)-thiazole-4-carboxylic
acid (3-bromo-phenyl)-amide

The title compound, MS (ISP): m/e=372.1 (M+H$^+$), was prepared as for example 52, steps A to C. Step C was performed using 3-bromo-aniline.

Example 55

5-Benzylamino-thiazole-4-carboxylic acid (6-methyl-pyridin-2-yl)-amide

The title compound, MS (ISP): m/e=325.1 (M+H$^+$), was prepared as for example 1, steps A to C. Step A was performed using isothiocyanatomethyl-benzene and yielded 5-benzylamino-thiazole-4-carboxylic acid ethyl ester. This was hydrolized in step B to 5-benzylamino-thiazole-4-carboxylic acid, which was reacted with 6-methyl-pyridin-2-ylamine in step C.

Example 56

5-Benzylamino-thiazole-4-carboxylic acid
(3-chloro-phenyl)-amide

The title compound, MS (ISP): m/e=344.1 (M+H$^+$), was prepared as for example 55, steps A to C. Step C was performed using 3-chloro aniline.

Example 57

5-Isopropylamino-thiazole-4-carboxylic acid
m-tolylamide

The title compound, MS (ISP): m/e=276.0 (M+H$^+$), was prepared as for example 1, steps A to C. Step A was performed using 2-isothiocyanato-propane and yielded 5-isopropylamino-thiazole-4-carboxylic acid ethyl ester. This was hydrolyzed in step B to 5-isopropylamino-thiazole-4-carboxylic acid, which was reacted with m-tolylamine in step C.

Example 58

5-Isopropylamino-thiazole-4-carboxylic acid
(6-bromo-pyridin-2-yl)-amide

The title compound, MS (ISP): m/e=343.1 (M+H$^+$), was prepared as for example 57, steps A to C. Step C was performed using 6-bromo-pyridin-2-ylamine.

Example 59

5-Isopropylamino-thiazole-4-carboxylic acid (4-methyl-thiazol-2-yl)-amide

The title compound, MS (ISP): m/e=282.9 (M+H$^+$), was prepared as for example 57, steps A to C. Step C was performed using 4-methyl-thiazol-2-ylamine.

Example 60

5-(1,1-Dimethyl-propylamino)-thiazole-4-carboxylic
acid (3-chloro-phenyl)-amide

The title compound, MS (ISP): m/e=324.3 (M+H$^+$), was prepared as for example 1, steps A to C. Step A was performed using 2-isothiocyanato-2-methyl-butane and yielded 5-(1,1-dimethyl-propylamino)-thiazole-4-carboxylic acid ethyl ester. This was hydrolyzed in step B to 5-(1,1-dimethyl-propylamino)-thiazole-4-carboxylic acid, which was reacted with 3-chloro aniline in step C.

Example 61

5-(1,1-Dimethyl-propylamino)-thiazole-4-carboxylic
acid m-tolylamide

The title compound, MS (ISP): m/e=304.4 (M+H$^+$), was prepared as for example 60, steps A to C. Step C was performed using m-tolylamine.

Example 62

5-(1,1-Dimethyl-propylamino)-thiazole-4-carboxylic
acid (6-methyl-pyridin-2-yl)-amide The title compound, MS (ISP): m/e=305.3 (M+H$^+$), was prepared as for example 60, steps A to C. Step C was performed using 6-methyl-pyridin-2-ylamine.

Example 63

5-(1,1-Dimethyl-propylamino)-thiazole-4-carboxylic acid (4-methyl-thiazol-2-yl)-amide The title compound, MS (ISP): m/e=311.1 (M+H$^+$), was prepared as for example 60, steps A to C. Step C was performed using 4-methyl-thiazol-2-yl-amine.

Example 64

5-Ethylamino-thiazole-4-carboxylic acid m-tolylamide

The title compound, MS (ISP): m/e=262.0 (M+H$^+$), was prepared as for example 1, steps A to C. Step A was performed using isothiocyanato-ethane and yielded 5-ethylamino-thiazole-4-carboxylic acid ethyl ester. This was hydrolyzed in step B to 5-ethylamino-thiazole-4-carboxylic acid, which was reacted with m-tolylamine in step C.

Example 65

5-Ethylamino-thiazole-4-carboxylic acid (6-bromo-pyridin-2-yl)-amide

The title compound, MS (ISP): m/e=329.0 (M+H$^+$), was prepared as for example 64, steps A to C. Step C was performed using 6-bromo-pyridin-2-yl-amine.

Example 66

5-Ethylamino-thiazole-4-carboxylic acid (4-methyl-thiazol-2-yl)-amide

The title compound, MS (ISP): m/e=269.1 (M+H$^+$), was prepared as for example 64, steps A to C. Step C was performed using 4-methyl-thiazol-2-yl-amine.

Example 67

5-(2,6-Dichloro-phenylamino)-thiazole-4-carboxylic acid (3-chloro-phenyl)-amide

The title compound, MS (ISP): m/e=400.3 (M+H$^+$), was prepared as for example 1, steps A to C. Step A was performed using 1,3-dichloro-2-isothiocyanato-benzene and yielded 5-(2,6-dichloro-phenylamino)-thiazole-4-carboxylic acid ethyl ester. This was hydrolyzed in step B to 5-(2,6-dichloro-phenylamino)-thiazole-4-carboxylic acid, which was reacted with 3-chloro aniline in step C.

Example 68

5-(2,6-Dichloro-phenylamino)-thiazole-4-carboxylic acid m-tolylamide

The title compound, MS (ISP): m/e=378.3 (M+H$^+$), was prepared as for example 67, steps A to C. Step C was performed using m-tolylamine.

Example 69

5-(2,6-Dichloro-phenylamino)-thiazole-4-carboxylic acid (6-methyl-pyridin-2-yl)-amide The title compound, MS (ISP): m/e=379.4 (M+H$^+$), was prepared as for example 67, steps A to C. Step C was performed using 6-methyl-pyridin-2-ylamine.

Example 70

5-(2,6-Dichloro-phenylamino)-thiazole-4-carboxylic acid (6-bromo-pyridin-2-yl)-amide The title compound, MS (ISP): m/e=445.1 (M+H$^+$), was prepared as for example 67, steps A to C. Step C was performed using 6-bromo-pyridin-2-yl-amine.

Example 71

5-(2,6-Dichloro-phenylamino)-thiazole-4-carboxylic acid (4-methyl-thiazol-2-yl)-amide The title compound, MS (ISP): m/e=385.0 (M+H$^+$), was prepared as for example 67, steps A to C. Step C was performed using 4-methyl-thiazol-2-yl-amine.

Example 72

5-(3,5-Dimethyl-isoxazol-4-ylamino)-thiazole-4-carboxylic acid (3-chloro-phenyl)-amide The title compound, MS (ISP): m/e=349.4 (M+H$^+$), was prepared as for example 1, steps A to C. Step A was performed using 4-isothiocyanato-3,5-dimethyl-isoxazole and yielded 5-(3,5-dimethyl-isoxazol-4-ylamino)-thiazole-4-carboxylic acid ethyl ester. This was hydrolyzed in step B to 5-(3,5-dimethyl-isoxazol-4-ylamino)-thiazole-4-carboxylic acid, which was reacted with 3-chloro aniline in step C.

Example 73

5-(3,5-Dimethyl-isoxazol-4-ylamino)-thiazole-4-carboxylic acid m-tolylamide

The title compound, MS (ISP): m/e=329.1 (M+H$^+$), was prepared as for example 72, steps A to C. Step C was performed using m-tolylamine.

Example 74

5-(3,5-Dimethyl-isoxazol-4-ylamino)-thiazole-4-carboxylic acid (6-methyl-pyridin-2-yl)-amide The title compound, MS (ISP): m/e=330.3 (M+H$^+$), was prepared as for example 72, steps A to C. Step C was performed using 6-methyl-pyridin-2-ylamine.

Example 75

5-(3,5-Dimethyl-isoxazol-4-ylamino)-thiazole-4-carboxylic acid (6-bromo-pyridin-2-yl)-amide The title compound, MS (ISP): m/e=396.0 (M+H$^+$), was prepared as for example 72, steps A to C. Step C was performed using 6-bromo-pyridin-2-yl-amine.

Example 76

5-(3,5-Dimethyl-isoxazol-4-ylamino)-thiazole-4-carboxylic acid (4-methyl-thiazol-2-yl)-amide The title compound, MS (ISP): m/e=336.1 (M+H$^+$), was prepared as for example 72, steps A to C. Step C was performed using 4-methyl-thiazol-2-yl-amine.

Example 77

5-(3-Cyano-phenylamino)-thiazole-4-carboxylic acid (3-chloro-phenyl)-amide

The title compound, MS (ISP): m/e=355.1 (M+H$^+$), was prepared as for example 1, steps A to C. Step A was performed using 3-isothiocyanato-benzonitrile and yielded 5-(3-cyano-phenylamino)-thiazole-4-carboxylic acid ethyl ester. This was hydrolyzed in step B to 5-(3-cyano-phenylamino)-thiazole-4-carboxylic acid, which was reacted with 3-chloro aniline in step C.

Example 78

5-(3-Cyano-phenylamino)-thiazole-4-carboxylic acid m-tolylamide

The title compound, MS (ISP): m/e=335.1 (M+H$^+$), was prepared as for example 77, steps A to C. Step C was performed using m-tolylamine.

Example 79

5-(3-Cyano-phenylamino)-thiazole-4-carboxylic acid (6-methyl-pyridin-2-yl)-amide The title compound, MS (ISP): m/e=336.0 (M+H$^+$), was prepared as for example 77, steps A to C. Step C was performed using 6-methyl-pyridin-2-ylamine.

Example 80

5-(3-Cyano-phenylamino)-thiazole-4-carboxylic acid (6-bromo-pyridin-2-yl)-amide

The title compound, MS (ISP): m/e=403.5 (M+H$^+$), was prepared as for example 77, steps A to C. Step C was performed using 6-bromo-pyridin-2-yl-amine.

Example 81

5-(3-Cyano-phenylamino)-thiazole-4-carboxylic acid (4-methyl-thiazol-2-yl)-amide The title compound, MS (ISP): m/e=342.1 (M+H$^+$), was prepared as for example 77, steps A to C. Step C was performed using 4-methyl-thiazol-2-yl-amine.

Example 82

5-(3-Cyano-phenylamino)-thiazole-4-carboxylic acid (2-methyl-thiazol-4-yl)-amide The title compound, MS (ISP): m/e=341.7 (M+H$^+$), was prepared as for example 77, steps A to C. Step C was performed using 2-methyl-thiazol-4-yl-amine.

Example 83

5-o-Tolylamino-thiazole-4-carboxylic acid (3-chloro-phenyl)-amide

The title compound, MS (ISP): m/e=344.0 (M+H$^+$), was prepared as for example 1, steps A to C. Step A was performed using 1-isothiocyanato-2-methyl-benzene and yielded 5-o-tolylamino-thiazole-4-carboxylic acid ethyl ester. This was hydrolyzed in step B to 5-o-tolylamino-thiazole-4-carboxylic acid, which was reacted with 3-chloro aniline in step C.

Example 84

5-o-Tolylamino-thiazole-4-carboxylic acid m-tolylamide

The title compound, MS (ISP): m/e=324.1 (M+H$^+$), was prepared as for example 83, steps A to C. Step C was performed using m-tolylamine.

Example 85

5-o-Tolylamino-thiazole-4-carboxylic acid (6-methyl-pyridin-2-yl)-amide

The title compound, MS (ISP): m/e=325.3 (M+H$^+$), was prepared as for example 83, steps A to C. Step C was performed using 6-methyl-pyridin-2-ylamine.

Example 86

5-o-Tolylamino-thiazole-4-carboxylic acid (4-methyl-thiazol-2-yl)-amide

The title compound, MS (ISP): m/e=331.1 (M+H$^+$), was prepared as for example 83, steps A to C. Step C was performed using 4-methyl-thiazol-2-yl-amine.

Example 87

5-(2-Bromo-phenylamino)-thiazole-4-carboxylic acid (6-methyl-pyridin-2-yl)-amide The title compound, MS (ISP): m/e=391.4 (M+H$^+$), was prepared as for example 1, steps A to C. Step A was performed using 1-bromo-2-isothiocyanato-benzene and yielded 5-(2-bromo-phenylamino)-thiazole-4-carboxylic acid ethyl ester. This was hydrolyzed in step B to 5-(2-bromo-phenylamino)-thiazole-4-carboxylic acid, which was reacted with 6-methyl-pyridin-2-ylamine in step C.

Example 88

5-(3-Acetyl-phenylamino)-thiazole-4-carboxylic acid (6-methyl-pyridin-2-yl)-amide The title compound, MS (ISP): m/e=353.4 (M+H$^+$), was prepared as for example 1, steps A to C. Step A was performed using 1-(3-isothiocyanato-phenyl)-ethanone and yielded 5-(3-acetyl-phenylamino)-thiazole-4-carboxylic acid ethyl ester. This was hydrolyzed in step B to 5-(3-acetyl-phenylamino)-thiazole-4-carboxylic acid, which was reacted with 6-methyl-pyridin-2-ylamine in step C.

Example 89

5-(3,5-Dimethoxy-phenylamino)-thiazole-4-carboxylic acid (6-methyl-pyridin-2-yl)-amide The title compound, MS (ISP): m/e=371.3 (M+H$^+$), was prepared as for example 1, steps A to C. Step A was performed using 1-isothiocyanato-3,5-dimethoxy-benzene and yielded 5-(3,5-dimethoxy-phenylamino)-thiazole-4-carboxylic acid ethyl ester. This was hydrolized in step B to 5-(3,5-dimethoxy-phenylamino)-thiazole-4-carboxylic acid, which was reacted with 6-methyl-pyridin-2-ylamine in step C.

Example 90

5-(3,5-Dimethoxy-phenylamino)-thiazole-4-carboxylic acid m-tolylamide

The title compound, MS (ISP): m/e=370.4 (M+H$^+$), was prepared as for example 89, steps A to C. Step C was performed using m-tolylamine.

Example 91

5-(3-Methoxy-phenylamino)-thiazole-4-carboxylic acid (6-methyl-pyridin-2-yl)-amide The title compound, MS (ISP): m/e=341.1 (M+H$^+$), was prepared as for example 1, steps A to C. Step A was performed using 1-isothiocyanato-3-methoxy-benzene and yielded 5-(3-methoxy-phenylamino)-thiazole-4-carboxylic acid ethyl ester. This was hydrolyzed in step B to 5-(3-methoxy-phenylamino)-thiazole-4-carboxylic acid, which was reacted with 6-methyl-pyridin-2-ylamine in step C.

Example 92

5-(3-Fluoro-phenylamino)-thiazole-4-carboxylic acid (6-methyl-pyridin-2-yl)-amide The title compound, MS (ISP): m/e=329.2 (M+H$^+$), was prepared as for example 1, steps A to C. Step A was performed using 1-fluoro-3-isothiocyanato-benzene and yielded 5-(3-fluoro-phenylamino)-thiazole-4-carboxylic acid ethyl ester. This was hydrolyzed in step B to 5-(3-fluoro-phenylamino)-thiazole-4-carboxylic acid, which was reacted with 6-methyl-pyridin-2-ylamine in step C.

Example 93

5-(2-Fluoro-phenylamino)-thiazole-4-carboxylic acid (6-methyl-pyridin-2-yl)-amide The title compound, MS (ISP): m/e=329.2 (M+H$^+$), was prepared as for example 1, steps A to C. Step A was performed using 1-fluoro-2-isothiocyanato-benzene and yielded 5-(2-fluoro-phenylamino)-thiazole-4-carboxylic acid ethyl ester. This was hydrolyzed in step B to 5-(2-fluoro-phenylamino)-thiazole-4-carboxylic acid, which was reacted with 6-methyl-pyridin-2-ylamine in step C.

Example 94

5-(4-Fluoro-phenylamino)-thiazole-4-carboxylic acid (6-methyl-pyridin-2-yl)-amide The title compound, MS (ISP): m/e=329.2 (M+H$^+$), was prepared as for example 1, steps A to C. Step A was performed using 1-fluoro-4-isothiocyanato-benzene and yielded 5-(4-fluoro-phenylamino)-thiazole-4-carboxylic acid ethyl ester. This was hydrolyzed in step B to 5-(4-fluoro-phenylamino)-thiazole-4-carboxylic acid, which was reacted with 6-methyl-pyridin-2-ylamine in step C.

Example 95

5-(2,5-Difluoro-phenylamino)-thiazole-4-carboxylic acid (6-methyl-pyridin-2-yl)-amide The title compound, MS (ISP): m/e=347.3 (M+H$^+$), was prepared as for example 1, steps A to C. Step A was performed using 1,4-difluoro-2-isothiocyanato-benzene and yielded 5-(2,5-difluoro-phenylamino)-thiazole-4-carboxylic acid ethyl ester. This was hydrolyzed in step B to 5-(2,5-difluoro-phenylamino)-thiazole-4-carboxylic acid, which was reacted with 6-methyl-pyridin-2-ylamine in step C.

Example 96

5-(2,6-Difluoro-phenylamino)-thiazole-4-carboxylic acid (6-methyl-pyridin-2-yl)-amide The title compound, MS (ISP): m/e=347.3 (M+H$^+$), was prepared as for example 1, steps A to C. Step A was performed using 1,3-difluoro-2-isothiocyanato-benzene and yielded 5-(2,6-difluoro-phenylamino)-thiazole-4-carboxylic acid ethyl ester. This was hydrolyzed in step B to 5-(2,6-difluoro-phenylamino)-thiazole-4-carboxylic acid, which was reacted with 6-methyl-pyridin-2-ylamine in step C.

1,3-Difluoro-2-isothiocyanato-benzene was synthesized as follows, according to scheme 1. A solution of 2,6-difluoro aniline (0.13 g, 1.01 mmol) in dichloromethane (10.00 ml) was treated with thiophosgene (0.12 g, 1.06 mmol) and diisopropylethylamine (0.26 g, 2.01 mmol). The mixture was stirred for 1 h at room temperature. The solvent was then evaporated, leaving 1,3-difluoro-2-isothiocyanato-benzene (0.17 g, 99%) as a light brown gum, which was used crude.

Example 97

5-(2-Methoxy-pyridin-3-ylamino)-thiazole-4-carboxylic acid (6-methyl-pyridin-2-yl)-amide The title compound, MS (ISP): m/e=342.1 (M+H$^+$), was prepared as for example 1, steps A to C. Step A was performed using 3-isothiocyanato-2-methoxy-pyridine and yielded 5-(2-methoxy-pyridin-3-ylamino)-thiazole-4-carboxylic acid ethyl ester. This was hydrolyzed in step B to 5-(2-methoxy-pyridin-3-ylamino)-thiazole-4-carboxylic acid, which was reacted with 6-methyl-pyridin-2-ylamine in step C. 3-Isothiocyanato-2-methoxy-pyridine was prepared as in example 96, starting from 2-methoxy-pyridin-3-ylamine.

Example 98

5-(3,5-Difluoro-phenylamino)-thiazole-4-carboxylic acid (6-methyl-pyridin-2-yl)-amide The title compound, MS (ISP): m/e=347.5 (M+H$^+$), was prepared as for example 1, steps A to C. Step A was performed using 1,3-difluoro-5-isothiocyanato-benzene and yielded 5-(3,5-difluoro-phenylamino)-thiazole-4-carboxylic acid ethyl ester. This was hydrolized in step B to 5-(3,5-difluoro-phenylamino)-thiazole-4-carboxylic acid, which was reacted with 6-methyl-pyridin-2-ylamine in step C. 1,3-Difluoro-5-isothiocyanato-benzene was prepared as in example 96, starting from 3,5-difluoro-phenylamine.

Example 99

5-(2,3-Difluoro-phenylamino)-thiazole-4-carboxylic acid (6-methyl-pyridin-2-yl)-amide The title compound, MS (ISP): m/e=347.3 (M+H$^+$), was prepared as for example 1, steps A to C. Step A was performed using 1,2-difluoro-3-isothiocyanato-benzene and yielded 5-(2,3-difluoro-phenylamino)-thiazole-4-carboxylic acid ethyl ester. This was hydrolized in step B to 5-(2,3-difluoro-phenylamino)-thiazole-4-carboxylic acid, which was reacted with 6-methyl-pyridin-2-ylamine in step C. 1,2-Difluoro-3-isothiocyanato-benzene was prepared as in example 96, starting from 2,3-difluoro-phenylamine.

Example 100

5-(2,5-Difluoro-phenylamino)-thiazole-4-carboxylic acid (2-methyl-pyrimidin-4-yl)-amide The title compound, MS (ISP): m/e=348.0 (M+H$^+$), was prepared as described in example 113, reacting 5-(2,5-difluoro-phenylamino)-thiazole-4-carboxylic acid ethyl ester with 2-methyl-pyrimidin-4-ylamine. 5-(2,5-Difluoro-phenylamino)-thiazole-4-carboxylic acid ethyl ester was prepared as described in example 95, step A.

Example 101

2-Methyl-5-(pyridin-3-ylamino)-thiazole-4-carboxylic acid (3-chloro-phenyl)-amide The title compound was prepared as illustrated in schemes 2 and 3.

A) A suspension of 2-acetylamino-cyanoacetic acid ethyl ester (1.70 g, 10.00 mmol) and 2,4-bis(4-methoxyphenyl)-1,3,2,4-dithiadiphosphetane 2,4-disulfide (Lawesson's reagent) (2.02 g, 5.00 mmol) in toluene (25.00 ml) was heated under argon to 110° C. and stirred for 22 h. The solvent was then evaporated, and the residue purified by flash chromatography (heptane/ethyl acetate 1:1) to yield 5-amino-2-methyl-thiazole-4-carboxylic acid ethyl ester (0.94 g, 50.5%) as a yellow solid, MS (ISP): m/e=187.3 (M+H$^+$).

B) A Schlenck flask was charged with 5-amino-2-methyl-thiazole-4-carboxylic acid ethyl ester (0.33 g, 1.80 mmol), 4,5-bis(diphenylphosphino)-9,9-dimethylxanthene (Xantphos) (0.15 g, 0.26 mmol) and palladium dibenzylideneacetone (Pd$_2$dba$_3$)-chloroform complex (0.08 g, 0.08 mmol). Degassed dioxane (6.00 ml) was added, followed by 3-bromopyridine (0.23 g, 1.50 mmol). The flask was subjected to 5 cycles of evacuation and backfiring with argon. The reaction mixture was then transferred under argon to a microwave vial containing cesium carbonate (0.84 g, 2.60 mmol). The vial was then irradiated in a microwave oven at 150° C. for 10 min. The mixture was diluted with THF and the solids filtered, washing with THF. The filtrate was evaporated and the residue purified by flash chromatography (ethyl acetate/methanol) to yield 2-methyl-5-(pyridin-3-ylamino)-thiazole-4-carboxylic acid ethyl ester (0.25 g, 65%) as a light yellow solid, MS (ISP): m/e=264.1 (M+H$^+$).

C) A solution of 2-methyl-5-(pyridin-3-ylamino)-thiazole-4-carboxylic acid ethyl ester (0.24 g, 0.90 mmol) in methanol (1.6 ml) was treated with a 2.55 N solution of KOH in water (1.06 ml). The mixture was stirred at 55° C. for 40 min then cooled to room temperature. The volatiles were evaporated and the residue dissolved in water (2.00 ml) and treated with HCl 1N under vigorous stirring until pH 5 was reached. The mixture was stirred for 1 h, then the solids were filtered, washed with water and dried under high vacuum to yield 2-methyl-5-(pyridin-3-ylamino)-thiazole-4-carboxylic acid (0.15 g, 70%) as a light yellow solid, MS (ISP): m/e=234.1 (M−H).

D) A solution of 2-methyl-5-(pyridin-3-ylamino)-thiazole-4-carboxylic acid (0.05 g, 0.21 mmol) in dry dimethylformamide (1.00 ml) was treated with 3-chloroaniline (0.04 g, 0.31 mmol), diisopropylethylamine (0.08 g, 0.63 mmol) and TBTU (0.10 g, 0.31 mmol) and stirred at room temperature overnight. The solvent was evaporated and the residue triturated with acetonitrile/methanol 1:1. Filtration and drying of the solid under vacuum provided the title compound (0.04 g, 48%) as a white solid, MS (ISP): m/e=344.8 (M+H$^+$). Alternatively, the reaction mixture could be purified directly by preparative HPLC (ZORBAX Eclipse XDB-C18, 21.2×50 mm, 5 μm, gradient acetonitrile/water+0.1% formic acid).

Example 102

2-Methyl-5-(pyridin-3-ylamino)-thiazole-4-carboxylic acid (6-methyl-pyridin-2-yl)-amide The title compound, MS (ISP): m/e=325.8 (M+H$^+$), was prepared as for example 101, steps A to D. Step D was performed using 6-methyl-pyridin-2-ylamine.

Example 103

2-Methyl-5-(pyridin-3-ylamino)-thiazole-4-carboxylic acid (2-methyl-thiazol-4-yl)-amide The title compound, MS (ISP): m/e=332.0 (M+H$^+$), was prepared as for example 101, steps A to D. Step D was performed using 2-methyl-thiazol-4-yl-amine.

Example 104

2-Methyl-5-(pyridin-3-ylamino)-thiazole-4-carboxylic acid (6-chloro-pyridin-2-yl)-amide The title compound, MS (ISP): m/e=346.1 (M+H$^+$), was prepared as for example 101, steps A to D. Step D was performed using 6-chloro-pyridin-2-ylamine.

Example 105

2-Methyl-5-(pyridin-3-ylamino)-thiazole-4-carboxylic acid (6-bromo-pyridin-2-yl)-amide The title compound, MS (ISP): m/e=389.7, 391.7 (M+H$^+$), was prepared as for example 101, steps A to D. Step D was performed using 6-bromo-pyridin-2-ylamine.

Example 106

2-Methyl-5-(pyridin-3-ylamino)-thiazole-4-carboxylic acid (3-cyano-phenyl)-amide The title compound, MS (ISP): m/e=335.9 (M+H$^+$), was prepared as for example 101, steps A to D. Step D was performed using 3-amino-benzonitrile.

Example 107

2-Methyl-5-(pyridin-3-ylamino)-thiazole-4-carboxylic acid (2-fluoro-5-methyl-phenyl)-amide The title compound, MS (ISP): m/e=343.0 (M+H$^+$), was prepared as for example 101, steps A to D. Step D was performed using 2-fluoro-5-methyl-phenylamine.

Example 108

2-Methyl-5-(pyridin-3-ylamino)-thiazole-4-carboxylic acid (5-chloro-2-fluoro-phenyl)-amide The title compound, MS (ISP): m/e=363.0 (M+H$^+$), was prepared as for example 101, steps A to D. Step D was performed using 5-chloro-2-fluoro-phenylamine.

Example 109

2-Methyl-5-(pyridin-3-ylamino)-thiazole-4-carboxylic acid (3-chloro-2-fluoro-phenyl)-amide The title compound, MS (ISP): m/e=363.0 (M+H$^+$), was prepared as for example 101, steps A to D. Step D was performed using 3-chloro-2-fluoro-phenylamine.

Example 110

2-Methyl-5-(pyridin-3-ylamino)-thiazole-4-carboxylic acid m-tolylamide

The title compound, MS (ISP): m/e=325.1 (M+H$^+$), was prepared as for example 101, steps A to D. Step D was performed using m-tolylamine.

Example 111

2-Methyl-5-(pyridin-3-ylamino)-thiazole-4-carboxylic acid (6-fluoromethyl-pyridin-2-yl)-amide The title compound, MS (ISP): m/e=344.1 (M+H$^+$), was prepared as for example 101, steps A to D. Step D was performed using 6-fluoromethyl-pyridin-2-ylamine. 6-Fluoromethyl-pyridin-2-ylamine was prepared according to the following scheme.

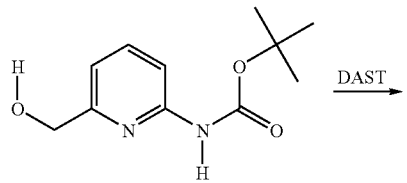

-continued

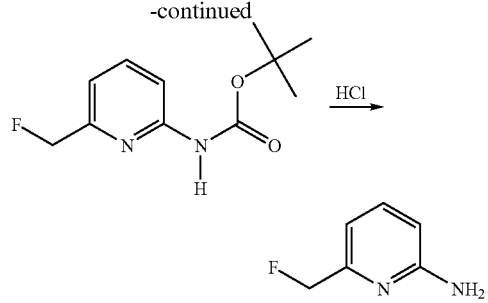

A) A solution of (6-hydroxymethyl-pyridin-2-yl)-carbamic acid tert-butyl ester (prepared as illustrated in example 135) (0.20 g, 0.90 mmol) in dichloromethane (20.00 ml) was cooled under argon to 0° C. and (diethylamino)sulfur trifluoride (DAST) (0.20 g, 1.25 mmol) was added dropwise. The resulting solution was stirred at room temperature for 30 min, then quenched by pouring the reaction mixture onto saturated sodium bicarbonate. The organic phase was separated, dried over sodium sulphate and evaporated to a orange oil, which was purified by flash chromatography (dichloromethane/ether) to yield (6-fluoromethyl-pyridin-2-yl)-carbamic acid tert-butyl ester (0.10 g, 51%) as a colorless oil, MS (ISP): m/e=211.3 (M+H$^+$).

B) A suspension of (6-fluoromethyl-pyridin-2-yl)-carbamic acid tert-butyl ester (0.10 g, 0.43 mmol) in 6N HCl (2.00 ml) was warmed to 100° C. and stirred for 6 h. The clear solution was then cooled to room temperature and neutralized with 5N NaOH. The aqueousaqueous phase was extracted several times with dichloromethane. The combined organic phases were dried over sodium sulfate and evaporated to yield 6-fluoromethyl-pyridin-2-ylamine (0.04 g, 78%) as colorless oil, which was used crude.

Example 112

2-Methyl-5-(pyridin-3-ylamino)-thiazole-4-carboxylic acid (2-chloro-pyridin-4-yl)-amide The title compound, MS (ISP): m/e=346.1 (M+H$^+$), was prepared as for example 101, steps A to D. Step D was performed using 2-chloro-pyridin-4-ylamine.

Example 113

2-Methyl-5-(pyridin-3-ylamino)-thiazole-4-carboxylic acid (2-methyl-pyridin-4-yl)-amide The title compound was prepared as follows, according to scheme 2.

A solution of 2-methyl-pyridin-4-ylamine (0.10 g, 0.91 mmol) in dry dioxane (2.00 ml) was added to a 2N solution of trimethylaluminium in heptane (0.46 ml, 0.91 mmol). The mixture was stirred at room temperature for 1 h, then 2-methyl-5-(pyridin-3-ylamino)-thiazole-4-carboxylic acid ethyl ester (0.08 g, 0.30 mmol) was added and the reaction mixture was irradiated in a microwave oven at 150° C. for 15 min. The mixture was quenched with water (1.00 ml) and diluted with dichloromethane. After drying with sodium sulphate, the solvent was evaporated. The residue was purified by flash chromatography (dichloromethane/methanol) yielding the title compound (0.04 g, 41%) as a yellow solid, MS (ISP): m/e=326.1 (M+H$^+$).

2-Methyl-5-(pyridin-3-ylamino)-thiazole-4-carboxylic acid ethyl ester was prepared as described in example 101, steps A to B.

Example 114

2-Methyl-5-(pyridin-3-ylamino)-thiazole-4-carboxylic acid (5-fluoro-pyridin-2-yl)-amide The title compound, MS (ISP): m/e=328.1 (M–H), was prepared as for example 113, using 5-fluoro-pyridin-2-ylamine.

Example 115

2-Methyl-5-(pyridin-3-ylamino)-thiazole-4-carboxylic acid (2-methyl-pyrimidin-4-yl)-amide The title compound was prepared as illustrated in schemes 4 and 5.

A) A solution of 2-methyl-thiazole-4-carboxylic acid ethyl ester (3.14 g, 20.00 mmol) in methanol (50.00 ml) was treated with 2N NaOH (30.00 ml) and stirred at room temperature for 45 min. Methanol was removed in vacuo and the resulting slurry was neutralized with HCl 2N (30.00 ml). The aqueous phase was then extracted three times with ethyl acetate. The combined organic layers were dried with sodium sulphate and evaporated. 2-Methyl-thiazole-4-carboxylic acid (2.48 g, 87%) was obtained as a yellow solid, MS (ISP): m/e=142.1 (M–H), which was used crude.

B) A solution of 2-methyl-thiazole-4-carboxylic acid (2.48 g, 17.32 mmol) in tetrahydrofurane (200.00 ml) was cooled to −78° C. under argon and treated with a 1.6N solution of buthyllithium in hexanes (22.74 ml, 36.38 mmol). The reaction mixture was left to warm to room temperature over 15 min, then cooled again to −78° C. A solution of elemental bromine (3.04 g, 19.05 mmol) in hexane (2.00 ml) was added. The reaction mixture was left to warm to room temperature, then quenched by addition of 1N HCl. The mixture was extracted three times with methylene chloride, and the combined organic layers were dried over sodium sulphate and evaporated. 5-Bromo-2-methyl-thiazole-4-carboxylic acid (3.79 g, 99%) was obtained as a yellow solid, MS (ISP): m/e=220.0, 222.1 (M–H), which was used crude.

C) A solution of 5-bromo-2-methyl-thiazole-4-carboxylic acid (1.50 g, 6.75 mmol) in methanol (80.00 ml) was treated with a saturated solution of HCl in ether (3.00 ml). The reaction mixture was heated at reflux for 3 h then the volatiles were removed. The residue was purified by flash chromatography (methylene chloride/methanol) yielding 5-bromo-2-methyl-thiazole-4-carboxylic acid methyl ester (1.30 g, 82%) as a white solid, MS (ISP): m/e=235.9, 237.9 (M+H$^+$).

D) Dry dioxane (10.00 ml) was degassed by bubbling with argon in an ultrasonic bath, then added to a sealed microwave vial containing a mixture of 4,5-bis(diphenylphosphino)-9,9-dimethylxanthene (Xantphos) (0.38 g, 0.66 mmol), palladium dibenzylideneacetone chloroform complex (0.21 g, 0.20 mmol), pyridin-3-ylamine (0.19 g, 2.00 mmol), 5-bromo-2-methyl-thiazole-4-carboxylic acid methyl ester (0.47 g, 2.00 mmol) and cesium carbonate (1.16 g, 6.00 mmol). The mixture was stirred for 10 min, then a few drops of 1-butyl-3-methylimidazolium hexafluorophosphate were added and the vial was irradiated in a microwave oven at 150° C. for 15 min. The volatiles were then removed under vacuum, and the residue was purified by flash chromatography (heptane/ethyl acetate), yielding 2-methyl-5-(pyridin-3-ylamino)-thiazole-4-carboxylic acid methyl ester (0.47 g, 94%), as a yellow solid, MS (ISP): m/e=250.1 (M+H$^+$).

E) A solution of 2-methyl-pyrimidin-4-ylamine (0.18 g, 1.66 mmol) in dry dioxane (5.00 ml) was added to a 2N solution of trimethylaluminium in heptane (0.83 ml, 1.66 mmol). The mixture was stirred at room temperature for 1 h, then 2-methyl-5-(pyridin-3-ylamino)-thiazole-4-carboxylic acid methyl ester (0.14 g, 0.55 mmol) was added and the reaction mixture was irradiated in a microwave oven at 140° C. for 15 min. The mixture was quenched with water (1.00 ml) and diluted with dichloromethane and methanol. After drying with sodium sulphate, the solvents were evaporated. The residue was purified by flash chromatography (dichloromethane/methanol), followed by trituration in diethyl ether. The title compound (0.04 g, 20%) was obtained as a white solid, MS (ISP): m/e=327.3 (M+H$^+$).

Example 116

2-Methyl-5-(pyrimidin-5-ylamino)-thiazole-4-carboxylic acid (6-chloro-pyridin-2-yl)-amide The title compound, MS (ISP): m/e=347.0 (M+H$^+$), was prepared as for example 101, steps A to D. Step B was performed using 5-bromo-pyrimidine and yielded 2-methyl-5-(pyrimidin-5-ylamino)-thiazole-4-carboxylic acid ethyl ester, which was hydrolized to 2-methyl-5-(pyrimidin-5-ylamino)-thiazole-4-carboxylic acid in step C. This was coupled with 6-chloro-pyridin-2-yl-amine in step D.

Example 117

2-Methyl-5-(pyrimidin-5-ylamino)-thiazole-4-carboxylic acid (6-methyl-pyridin-2-yl)-amide The title compound, MS (ISP): m/e=327.1 (M+H$^+$), was prepared as for example 116, steps A to D. Step D was performed using 6-methyl-pyridin-2-yl-amine.

Example 118

2-Methyl-5-(pyrimidin-5-ylamino)-thiazole-4-carboxylic acid (2-methyl-thiazol-4-yl)-amide The title compound, MS (ISP): m/e=333.3 (M+H$^+$), was prepared as for example 116, steps A to D. Step D was performed using 2-methyl-thiazol-4-yl-amine.

Example 119

2-Methyl-5-(pyrimidin-5-ylamino)-thiazole-4-carboxylic acid (2-methyl-pyridin-4-yl)-amide The title compound, MS (ISP): m/e=327.1 (M+H$^+$), was prepared as described in example 113, reacting 2-methyl-5-(pyrimidin-5-ylamino)-thiazole-4-carboxylic acid ethyl ester with 2-methyl-pyridin-4-ylamine. 2-Methyl-5-(pyrimidin-5-ylamino)-thiazole-4-carboxylic acid ethyl ester was prepared as described in example 116, steps A to B.

Example 120

2-Methyl-5-(pyrimidin-5-ylamino)-thiazole-4-carboxylic acid (5-fluoro-pyridin-2-yl)-amide The title compound, MS (ISP): m/e=331.1 (M+H$^+$), was prepared as described in example 113, reacting 2-methyl-5-

(pyrimidin-5-ylamino)-thiazole-4-carboxylic acid ethyl ester with 5-fluoro-pyridin-2-ylamine. 2-Methyl-5-(pyrimidin-5-ylamino)-thiazole-4-carboxylic acid ethyl ester was prepared as described in example 116, steps A to B.

Example 121

2-Methyl-5-(pyrimidin-5-ylamino)-thiazole-4-carboxylic acid (3-chloro-phenyl)-amide The title compound, MS (ISP): m/e=346.5 (M+H$^+$), was prepared as for example 116, steps A to D. Step D was performed using 3-chloro aniline.

Example 122

2-Methyl-5-(4-methyl-pyridin-3-ylamino)-thiazole-4-carboxylic acid (3-chloro-phenyl)-amide The title compound, MS (ISP): m/e=359.5 (M+H$^+$), was prepared as for example 101, steps A to D. Step B was performed using 3-bromo-4-methyl-pyridine and yielded 2-methyl-5-(4-methyl-pyridin-3-ylamino)-thiazole-4-carboxylic acid ethyl ester, which was hydrolized to 2-methyl-5-(4-methyl-pyridin-3-ylamino)-thiazole-4-carboxylic acid in step C. This was coupled with 3-chloro aniline in step D.

Example 123

2-Methyl-5-(4-methyl-pyridin-3-ylamino)-thiazole-4-carboxylic acid (6-methyl-pyridin-2-yl)-amide The title compound, MS (ISP): m/e=340.2 (M+H$^+$), was prepared as for example 122, steps A to D. Step D was performed using 6-methyl-pyridin-2-ylamine.

Example 124

2-Methyl-5-(4-methyl-pyridin-3-ylamino)-thiazole-4-carboxylic acid (2-methyl-pyridin-4-yl)-amide The title compound, MS (ISP): m/e=340.3 (M−H), was prepared as for example 113, using 2-methyl-5-(4-methyl-pyridin-3-ylamino)-thiazole-4-carboxylic acid ethyl ester and 2-methyl-pyridin-4-ylamine. 2-Methyl-5-(4-methyl-pyridin-3-ylamino)-thiazole-4-carboxylic acid ethyl ester was prepared as described in example 101, steps A to B, using 3-bromo-4-methyl-pyridine.

Example 125

5-(5-Cyano-pyridin-3-ylamino)-2-methyl-thiazole-4-carboxylic acid (3-chloro-phenyl)-amide The title compound, MS (ISP): m/e=370.6 (M+H$^+$), was prepared as for example 101, steps A to D. Step B was performed using 5-bromo-nicotinonitrile and yielded 5-(5-cyano-pyridin-3-ylamino)-2-methyl-thiazole-4-carboxylic acid ethyl ester, which was hydrolized to 5-(5-cyano-pyridin-3-ylamino)-2-methyl-thiazole-4-carboxylic acid in step C. This was coupled with 3-chloro aniline in step D.

Example 126

5-(5-Cyano-pyridin-3-ylamino)-2-methyl-thiazole-4-carboxylic acid (6-methyl-pyridin-2-yl)-amide The title compound, MS (ISP): m/e=351.2 (M+H$^+$), was prepared as for example 125, steps A to D. Step D was performed using 6-methyl-pyridin-2-ylamine.

Example 127

5-Amino-2-methyl-thiazole-4-carboxylic acid (3-chloro-phenyl)-amide

The title compound was prepared as described in scheme 6.
A) A solution of 5-amino-2-methyl-thiazole-4-carboxylic acid ethyl ester (prepared as described in example 105, step A) (0.10 g, 0.54 mmol) in THF (2.5 ml) was treated with dimethylaminopyridine (DMAP) and di-tert-butyl dicarbonate (Boc$_2$O). The mixture was irradiated in a microwave oven at 100° C. for 10 min, then the solvent was evaporated. The residue was purified by flash chromatography (heptane/ethyl acetate) yielding 2-tert-butoxycarbonylamino-5-methyl-thiophene-3-carboxylic acid ethyl ester (0.11 g, 70%) as a yellow oil, MS (ISP): m/e=287.2 (M+H$^+$).
B) A solution of 2-tert-butoxycarbonylamino-5-methyl-thiophene-3-carboxylic acid ethyl ester (0.69 g, 2.41 mmol) in MeOH (7.00 ml) was treated with a 2.55 N solution of KOH in water (2.83 ml, 7.22 mmol). The mixture was warmed to 55° C. for 1 h, then acidified to pH 5 with HCl 1N. The precipitated solid was filtered and dried under vacuum to yield 2-tert-btoxycarbonylamino-5-methyl-thiophene-3-carboxylic acid (0.52 g, 83%) as a white solid, MS (ISP): m/e=257.1 (M−H$^+$).
C) A solution of 2-tert-butoxycarbonylamino-5-methyl-thiophene-3-carboxylic acid (1.16 g, 4.49 mmol) in dimethylformamide (50.00 ml) was treated with 3-chloro aniline (0.86 g, 6.73 mmol), DIPEA (1.74 g, 13.47 mmol) and TBTU (2.16 g, 6.73 mmol) and stirred at room temperature for 48 h. The volatiles were evaporated and the residue purified by flash chromatography (heptane/ethyl acetate), to yield [3-(3-chloro-phenylcarbamoyl)-5-methyl-thiophen-2-yl]-carbamic acid tert-butyl ester (0.45 g, 27%) as a yellow solid, MS (ISP): m/e=368.6 (M+H$^+$)
D) [3-(3-Chloro-phenylcarbamoyl)-5-methyl-thiophen-2-yl]-carbamic acid tert-butyl ester (0.45 g, 1.20 mmol) was dissolved in trifluoroacetic acid (TFA) (16.00 ml) and stirred at room temperature for 15 min. The acid was then evaporated and the residue purified by flash chromatography (dichloromethane/methanol) to yield the title compound (0.28 g, 88%) as a light brown solid, MS (ISP): m/e=268.3 (M+H$^+$).

Example 128

5-Benzoylamino-2-methyl-thiazole-4-carboxylic acid (3-chloro-phenyl)-amide

The title compound was prepared by benzoylation of 5-amino-2-methyl-thiazole-4-carboxylic acid (3-chloro-phenyl)-amide (prepared as illustrated in example 127), as follows.
A solution of 5-amino-2-methyl-thiazole-4-carboxylic acid (3-chloro-phenyl)-amide (0.04 g, 0.17 mmol) in dry dioxane (0.50 ml) and pyridine (0.02 ml) was cooled to 0° C. and treated with benzoyl chloride (0.02 g, 0.17 mmol). The mixture was then left to warm to room temperature and stirred overnight. After evaporation of the solvent, the residue was triturated in acetonitrile to yield the title compound (0.003 g, 4%) as a white solid, MS (ISP): m/e=372.3 (M+H$^+$)

Example 129

2-Methyl-5-(pyridin-4-ylamino)-thiazole-4-carboxylic acid (3-chloro-phenyl)-amide The title compound was prepared by reaction of 5-amino-2-methyl-thiazole-4-carboxylic acid (3-chloro-phenyl)-amide (prepared as illustrated in example 127) with 4-bromopyridine, as follows.

Dry dioxane (1.00 ml) was added to a sealed microwave vial containing a mixture of 4,5-bis(diphenylphosphino)-9,9-dimethylxanthene (Xantphos) (0.015 g, 0.026 mmol), palladium dibenzylideneacetone chloroform complex (0.008 g, 0.008 mmol), 4-bromopyridine hydrochloride (0.03 g, 0.15 mmol), 5-amino-2-methyl-thiazole-4-carboxylic acid (3-chlorophenyl)-amide (0.05 g, 0.19 mmol) and cesium carbonate (0.18 g, 0.54 mmol). The mixture was stirred for 10 min, then irradiated in a microwave oven at 150° C. for 10 min. The volatiles were then removed under vacuum, and the residue was purified by flash chromatography (dichloromethane/methanol), yielding the title compound (0.005 g, 9%), as a yellow solid, MS (ISP): m/e=345.5 (M+H$^+$).

Example 130

2-Methyl-5-(2-methyl-pyridin-3-ylamino)-thiazole-4-carboxylic acid (6-methyl-pyridin-2-yl)-amide The title compound was prepared as illustrated in scheme 4.

A) A solution of 5-bromo-2-methyl-thiazole-4-carboxylic acid (prepared as described in example 119, steps A to B) (0.31 g, 1.39 mmol) in dimethylformamide (20.00 ml) was treated with DIPEA (0.27 g, 2.08 mmol), TBTU (0.47 g, 1.46 mmol) and 6-methyl-pyridin-2-ylamine (0.18 g, 1.66 mmol) and stirred at room temperature overnight. The volatiles were removed under vacuum and the residue purified by flash chromatography (heptane/ethyl acetate) to yield 2-bromo-5-methyl-thiophene-3-carboxylic acid (6-methyl-pyridin-2-yl)-amide (0.16 g, 38%) as a light yellow solid, MS (ISP): m/e=314.0, 312.0 (M+H$^+$)

B) A solution of 2-bromo-5-methyl-thiophene-3-carboxylic acid (6-methyl-pyridin-2-yl)-amide (0.05 g, 0.16 mmol) and 2-methyl-pyridin-3-ylamine in dry dioxane (1.50 ml) was degassed by sonication and argon bubbling. 4,5-Bis(diphenylphosphino)-9,9-dimethylxanthene (Xantphos) (0.016 g, 0.03 mmol) and palladium dibenzylideneacetone chloroform complex (0.008 g, 0.01 mmol) were added and the mixture was stirred until dissolution was complete. Finally, the mixture was treated with cesium carbonate (0.05 g, 0.28 mmol) and irradiated in a microwave oven at 150° C. for 13 min. The solvent was removed under vacuum and the residue purified by flash chromatography (dichloromethane/methanol/ammonia) to yield the title compound (0.015 g, 28%) as a light yellow solid, MS (ISP): m/e=340.1 (M+H$^+$).

Example 131

2-Methyl-5-(pyrazin-2-ylamino)-thiazole-4-carboxylic acid (6-methyl-pyridin-2-yl)-amide The title compound, MS (ISP): m/e=327.3 (M+H$^+$), was prepared as for example 130, steps A to B. Step B was performed using pyrazin-2-ylamine.

Example 132

2-Methyl-5-(pyrimidin-2-ylamino)-thiazole-4-carboxylic acid (6-methyl-pyridin-2-yl)-amide The title compound, MS (ISP): m/e=327.3 (M+H$^+$), was prepared as for example 130, steps A to B. Step B was performed using pyrimidin-2-ylamine.

Example 133

2-Methyl-5-(pyridin-2-ylamino)-thiazole-4-carboxylic acid (6-methyl-pyridin-2-yl)-amide The title compound, MS (ISP): m/e=326.1 (M+H$^+$), was prepared as for example 130, steps A to B. Step B was performed using pyridin-2-ylamine.

Example 134

2-Methyl-5-(pyridazin-3-ylamino)-thiazole-4-carboxylic acid (6-methyl-pyridin-2-yl)-amide The title compound, MS (ISP): m/e=327.3 (M+H$^+$), was prepared as for example 130, steps A to B. Step B was performed using pyridazin-3-ylamine.

Example 135

Acetic acid 6-{[2-methyl-5-(pyridin-3-ylamino)-thiazole-4-carbonyl]-amino}-pyridin-2-ylmethyl ester The title compound, MS (ISP): m/e=384.1 (M+H$^+$), was prepared as for example 130, steps A to B. Step A was performed using acetic acid 6-amino-pyridin-2-ylmethyl ester and using a different condensation protocol as follows:

A solution of 5-bromo-2-methyl-thiazole-4-carboxylic (prepared as described in example 119, steps A to B) (0.13 g, 0.60 mmol) in dichloromethane (5.00 ml) and DMF (0.10 ml) was treated with thionyl chloride (0.08 g, 0.66 mmol) and stirred at room temperature for 4.5 h. After this time, 6-amino-pyridin-2-ylmethyl ester (0.10 g, 0.60 mmol) and DIPEA (0.16 g, 1.20 mmol) were added, and the mixture stirred for 30 min. The solvents were then evaporated and the residue purified by flash chromatography (heptane/ethyl acetate) to yield acetic acid 6-[(5-bromo-2-methyl-thiazole-4-carbonyl)-amino]-pyridin-2-ylmethyl ester (0.17 g, 76%) as a white solid, MS (ISP): m/e=372.0, 370.0 (M+H$^+$). Acetic acid 6-[(5-bromo-2-methyl-thiazole-4-carbonyl)-amino]-pyridin-2-ylmethyl ester was then coupled with pyridin-3-ylamine in step B to yield the title compound.

Acetic acid 6-amino-pyridin-2-ylmethyl ester was prepared as illustrated in the following scheme:

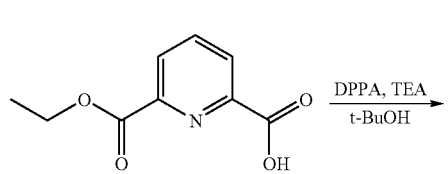

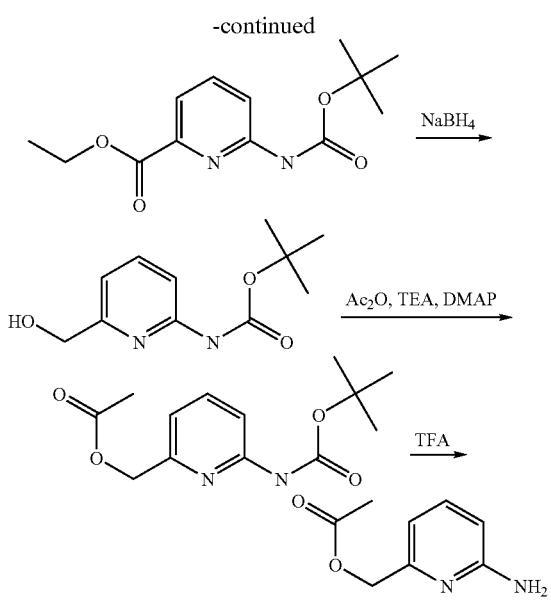

A) A solution of pyridine-2,6-dicarboxylic acid monoethyl ester (1.00 g, 5.12 mmol), triethylamine (1.04 g, 10.24 mmol), diphenylphosphoryl azide (DPPA) (1.93 g, 7.02 mmol) and tert-butanol (3.00 ml) in toluene (30.00 ml) was warmed at 100° C. for 20 h. The mixture was then cooled at room temperature, diluted with ethyl acetate and washed with saturated sodium bicarbonate and brine. The organic layer was then dried over sodium sulphate and evaporated. The residue was purified by flash chromatography to yield 6-tert-butoxycarbonylamino-pyridine-2-carboxylic acid ethyl ester (1.06 g, 78%) as a viscous orange oil, MS (ISP): m/e=267.3 (M+H$^+$).

B) A solution of 6-tert-butoxycarbonylamino-pyridine-2-carboxylic acid ethyl ester (1.06 g, 3.98 mmol) in ethanol (30.00 ml) was flushed with argon and treated with finely powdered CaCl$_2$ (0.89 g, 7.98 mmol) and stirred at room temperature for 5 min. The mixture was then cooled to 0° C. and sodium boron hydride was added portionwise. The mixture was stirred at 0° C. for 2 h, then poured into water and extracted with chloroform. The combined extracts were dried over sodium sulphate and evaporated to a thick colorless oil (0.85 g, 95%) consisting of almost pure (6-hydroxymethyl-pyridin-2-yl)-carbamic acid tert-butyl ester, MS (ISP): m/e=225.1 (M+H$^+$), which was used crude.

C) (6-Hydroxymethyl-pyridin-2-yl)-carbamic acid tert-butyl ester (0.85 g, 3.79 mmol) was dissolved in dichloromethane (30.00 ml) and triethylamine (1.32 ml) and treated with dimethylaminopyridine (0.09 g, 0.76 mmol) and acetic anhydride (0.43 g, 4.17 mmol). The mixture was stirred at room temperature for 10 min, then partitioned between water and dichloromethane. The organic layer was dried over sodium sulphate and evaporated. The residue was purified by flash chromatography (heptane/ethyl acetate) to yield acetic acid 6-tert-butoxycarbonylamino-pyridin-2-ylmethyl ester (0.85 g, 84%) as a white solid, MS (ISP): m/e=267.1 (M+H$^+$).

D) A solution of acetic acid 6-tert-butoxycarbonylamino-pyridin-2-ylmethyl ester (0.85 g, 3.18 mmol) in dichloromethane (30.00 ml) was cooled to 0° C. and trifluoroacetic acid (2.40 ml) was added dropwise. After stirring at room temperature for 3 h, further trifluoroacetic acid (1.50 ml) was added and stirring was maintained for further 2 h. The reaction mixture was basified with 1 N sodium bicarbonate (54.00 ml) to a pH 8. The organic phase was separated and the aqueous phase extracted twice with dichloromethane. The combined organic layers were dried over sodium sulphate and evaporated to yield pure acetic acid 6-amino-pyridin-2-ylmethyl ester (0.54 g, 100%) as a white solid, MS (ISP): m/e=167.4 (M+H$^+$).

Example 136

2-Methyl-5-(pyridin-3-ylamino)-thiazole-4-carboxylic acid (6-hydroxymethyl-pyridin-2-yl)-amide The title compound was prepared by hydrolysis of acetic acid 6-{[2-methyl-5-(pyridin-3-ylamino)-thiazole-4-carbonyl]-amino}-pyridin-2-ylmethyl ester (prepared as described in example 135) as follows.

A solution of acetic acid 6-{[2-methyl-5-(pyridin-3-ylamino)-thiazole-4-carbonyl]-amino}-pyridin-2-ylmethyl ester (0.046 g, 0.12 mmol) in methanol (20.00 ml) was treated with a 2N solution of NaOH in water (1.00 ml, 2.00 mmol). After 15 min stirring at room temperature, the mixture was acidified with HCl 2N, and the solvents removed. The residue was purified by flash chromatography (dichloromethane/methanol) to yield the title compound (0.035 g, 85%) as a light yellow solid, MS (ISP): m/e=342.1 (M+H$^+$).

Example 137

2-Methyl-5-(pyrimidin-5-ylamino)-thiazole-4-carboxylic acid (6-hydroxymethyl-pyridin-2-yl)-amide The title compound, MS (ISP): m/e=343.0 (M+H$^+$), was prepared as for example 136, by hydrolysis of acetic acid 6-{[2-methyl-5-(pyrimidin-5-ylamino)-thiazole-4-carbonyl]-amino}-pyridin-2-ylmethyl ester.

Acetic acid 6-{[2-methyl-5-(pyrimidin-5-ylamino)-thiazole-4-carbonyl]-amino}-pyridin-2-ylmethyl ester was prepared as for example 116, steps A to D. Step D was performed using acetic acid 6-amino-pyridin-2-ylmethyl ester.

Acetic acid 6-amino-pyridin-2-ylmethyl ester was prepared as illustrated for example 135.

Example 138

Acetic acid 2-methyl-6-{[2-methyl-5-(pyridin-3-ylamino)-thiazole-4-carbonyl]-amino}-pyridin-3-yl ester The title compound, MS (ISP): m/e=384.4 (M+H$^+$), was prepared as for example 135, steps A to B. Step A was performed using acetic acid 6-amino-2-methyl-pyridin-3-yl ester, and yielded acetic acid 6-[(5-bromo-2-methyl-thiazole-4-carbonyl)-amino]-2-methyl-pyridin-3-yl ester, which was used in step B.

Acetic acid 6-amino-2-methyl-pyridin-3-yl ester was prepared according to the following scheme:

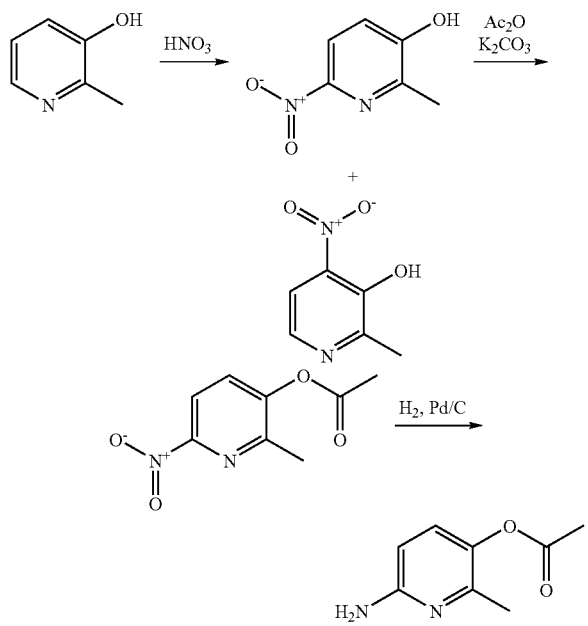

A) While maintaining a temperature of 0-5° C. with external ice cooling, 3-hydroxy-2-methyl pyridine (10.00 g, 91.63 mmol) was added gradually to concentrated sulfuric acid (65.00 ml). A mixture of concentrated sulfuric acid (8.50 ml) and nitric acid (6.50 g, 103.16 mmol) was added over 2 h. The resulting mixture was poured onto ice. Addition of a few milliliters of saturated ammonium hydroxide caused precipitation of crude 2-methyl-6-nitro-pyridin-3-ol. This was collected by filtration and recrystallized from methanol/water to yield pure 2-methyl-6-nitro-pyridin-3-ol (1.37 g, 10%). Basification of the mother liquors to pH 3-4 triggered precipitation of the isomeric 2-methyl-4-nitro-pyridin-3-ol (major component), which was discarded.

B) A solution of 2-methyl-6-nitro-pyridin-3-ol (0.77 g, 5.00 mmol) in acetone (50.00 ml) was treated with acetic anhydride (1.00 g, 9.80 mmol) and potassium carbonate (2.07 g, 15.00 mmol). The mixture was stirred for 1 h at room temperature then filtered, washing with acetone. The solvent was removed, yielding acetic acid 2-methyl-6-nitro-pyridin-3-yl ester (0.75 g, 77%) as a white solid, MS (ISP): m/e=196.1 (M+), which was used crude.

C) Acetic acid 2-methyl-6-nitro-pyridin-3-yl ester (0.30 g, 1.53 mmol) was dissolved in ethanol. 10% Pd/C (0.04 g, 0.38 mmol) was added, and the mixture was put under an atmosphere of hydrogen and stirred vigorously for 50 min at room temperature. The catalyst was filtered off, washing with ethanol, and the solvent removed under vacuum to yield acetic acid 6-amino-2-methyl-pyridin-3-yl ester (0.24 g, 95%) as a white solid, MS (ISP): m/e=166.2 (M+), which was used crude.

Example 139

2-Methyl-5-(pyridin-3-ylamino)-thiazole-4-carboxylic acid (5-hydroxy-6-methyl-pyridin-2-yl)-amide The title compound, MS (ISP): m/e=342.1 (M+H+), was prepared as for example 136, by hydrolysis of acetic acid 2-methyl-6-{[2-methyl-5-(pyridin-3-ylamino)-thiazole-4-carbonyl]-amino}-pyridin-3-yl ester, prepared as described in example 138.

Example 140

2-Methyl-5-(pyrimidin-5-ylamino)-thiazole-4-carboxylic acid (5-hydroxy-6-methyl-pyridin-2-yl)-amide The title compound, MS (ISP): m/e=343.0 (M+H+), was prepared as for example 136, by hydrolysis of acetic acid 2-methyl-6-{[2-methyl-5-(pyrimidin-5-ylamino)-thiazole-4-carbonyl]-amino}-pyridin-3-yl ester.

Acetic acid 2-methyl-6-{[2-methyl-5-(pyrimidin-5-ylamino)-thiazole-4-carbonyl]-amino}-pyridin-3-yl ester was prepared as for example 116, steps A to D. Step D was performed using acetic acid 6-amino-2-methyl-pyridin-3-yl ester.

Acetic acid 6-amino-2-methyl-pyridin-3-yl ester was prepared as illustrated for example 138.

Example 141

3-[4-(3-Chloro-phenylcarbamoyl)-2-methyl-thiazol-5-ylamino]-benzoic acid methyl ester The title compound, MS (ISP): m/e=401.4 (M+H+), was prepared as for example 130, steps A to B. Step A was performed using 3-chloro aniline and yielded 5-bromo-2-methyl-thiazole-4-carboxylic acid (3-chloro-phenyl)-amide. This was coupled with 3-amino-benzoic acid methyl ester in step B.

Example 142

5-(3-Hydroxymethyl-phenylamino)-2-methyl-thiazole-4-carboxylic acid (3-chloro-phenyl)-amide The title compound, MS (ISP): m/e=374.5 (M+H+), was prepared by reduction of 3-[4-(3-chloro-phenylcarbamoyl)-2-methyl-thiazol-5-ylamino]-benzoic acid methyl ester (prepared as illustrated in example 141) as follows.

A solution of 3-[4-(3-chloro-phenylcarbamoyl)-2-methyl-thiazol-5-ylamino]-benzoic acid methyl ester (0.02 g, 0.05 mmol) in THF (1.00 ml) was treated at room temperature with lithium aluminium hydride (0.008 g, 0.20 mmol) and stirred at room temperature for 30 min. The reaction mixture was quenched with a drop of 5N NaOH and sodium sulphate. The solids were filtered and the mother liquor evaporated. The residue was purified by flash chromatography (heptane/ethyl acetate) to yield the title compound (0.02 g, 90%) as a light brown gum.

Example 143

5-(3-Acetylamino-phenylamino)-2-methyl-thiazole-4-carboxylic acid (3-chloro-phenyl)-amide The title compound, MS (ISP): m/e=401.3 (M+H+), was prepared as for example 141, steps A to B. Step B was performed using N-(3-amino-phenyl)-acetamide.

Example 144

2-Methyl-5-(3-sulfamoyl-phenylamino)-thiazole-4-carboxylic acid (3-chloro-phenyl)-amide The title compound, MS (ISP): m/e=423.2 (M+H$^+$), was prepared as for example 141, steps A to B. Step B was performed using 3-amino-benzenesulfonamide.

Example 145

{3-[4-(3-Chloro-phenylcarbamoyl)-2-methyl-thiazol-5-ylamino]-benzyl}-carbamic acid tert-butyl ester The title compound, MS (ISP): m/e=473.6 (M+H$^+$), was prepared as for example 141, steps A to B. Step B was performed using (3-amino-benzyl)-carbamic acid tert-butyl ester.

Example 146

5-(3-Aminomethyl-phenylamino)-2-methyl-thiazole-4-carboxylic acid (3-chloro-phenyl)-amide The title compound, MS (ISP): m/e=373.1 (M+H$^+$), was prepared by deprotection of {3-[4-(3-chloro-phenylcarbamoyl)-2-methyl-thiazol-5-ylamino]-benzyl}-carbamic acid tert-butyl ester (prepared as illustrated in example 145) as follows.

A solution of {3-[4-(3-chloro-phenylcarbamoyl)-2-methyl-thiazol-5-ylamino]-benzyl}-carbamic acid tert-butyl ester (0.02 g, 0.04 mmol) in dichloromethane (0.50 ml) was treated with trifluoroacetic acid (0.10 ml) and stirred at room temperature for 5 min. The reaction mixture was diluted with dichloromethane and quenched with saturated sodium hydrogenocarbonate. The organic layer is separated, dried over sodium sulphate and evaporated, to yield the title compound (0.015 g, 94%).

Example 147

3-[2-Methyl-4-(6-methyl-pyridin-2-ylcarbamoyl)-thiazol-5-ylamino]-benzoic acid methyl ester The title compound, MS (ISP): m/e=382.9 (M+H$^+$), was prepared as for example 130, steps A to B. Step B was performed using 3-amino-benzoic acid methyl ester.

Example 148

5-(3-Hydroxymethyl-phenylamino)-2-methyl-thiazole-4-carboxylic acid (6-methyl-pyridin-2-yl)-amide The title compound, MS (ISP): m/e=354.9 (M+H$^+$), was prepared by reduction of 3-[2-methyl-4-(6-methyl-pyridin-2-ylcarbamoyl)-thiazol-5-ylamino]-benzoic acid methyl ester (prepared as illustrated in example 147) with lithium aluminium hydride, as described for example 142.

Example 149

5-(3-Methanesulfonyl-phenylamino)-2-methyl-thiazole-4-carboxylic acid (6-methyl-pyridin-2-yl)-amide The title compound, MS (ISP): m/e=403.4 (M+H$^+$), was prepared as for example 130, steps A to B. Step B was performed using 3-methanesulfonyl-phenylamine.

Example 150

2-Methyl-5-(3-sulfamoyl-phenylamino)-thiazole-4-carboxylic acid (6-methyl-pyridin-2-yl)-amide The title compound, MS (ISP): m/e=403.9 (M+H$^+$), was prepared as for example 130, steps A to B. Step B was performed using 3-amino-benzenesulfonamide.

Example 151

5-Dimethylamino-2-methyl-thiazole-4-carboxylic acid (6-methyl-pyridin-2-yl)-amide The title compound, MS (ISP): m/e=277.1 (M+H$^+$), was prepared by reaction of 2-bromo-5-methyl-thiophene-3-carboxylic acid (6-methyl-pyridin-2-yl)-amide (prepared as illustrated in example 130) with dimethylamine as follows.

2-Bromo-5-methyl-thiophene-3-carboxylic acid (6-methyl-pyridin-2-yl)-amide (0.05 g, 0.16 mmol) was dissolved in a 2N solution of dimethylamine in methanol (2.00 ml). The mixture was stirred at 50° C. for 48 h (after the first 24 h, another 1.00 ml of dimethylamine solution was added). The volatiles were then evaporated, and the residue purified by flash chromatography (heptane/ethyl acetate), yielding the title compound (0.02 g, 45%) as a white solid.

Example 152

2-(2-Methoxy-ethyl)-5-(pyridin-3-ylamino)-thiazole-4-carboxylic acid (6-methyl-pyridin-2-yl)-amide The title compound was prepared as described in schemes 2 and 3

A) A solution of sodium nitrite (57.30 g, 830.60 mmol) in water (710.00 ml) was treated with ethyl cyanoacetate (100.00 g, 884.00 mmol). 85% Orthophosphoric acid (36.60 ml, 540.00 mmol) was added dropwise over 45 min, while keeping the temperature of the reaction mixture below 35° C. with the aid of an ice bath. At the end of the addition, the mixture was warmed to 40° C. and stirred for 1 hour. The reaction was quenched at 45° C. with fuming HCl (73.90 ml, 880.00 mmol), and the mixture was then left to cool to room temperature and at 0° C. overnight to complete precipitation. The solid was filtered, the filtrate washed with water and dried under high vacuum overnight to yield 70 g of cyano-hydroxyimino-acetic acid ethyl ester as white crystals. A second batch was obtained by extracting the mother liquor with ether (44.00 g, total yield 91%).

B) Cyano-hydroxyimino-acetic acid ethyl ester (30.00 g, 211.10 mmol) was added portionwise to a solution of water (766.00 ml) and saturated sodium bicarbonate (192.00 ml). Sodium dithionite (73.50 g, 422.00 mmol) was then added during 5 min. The mixture was stirred at room temperature for 2 hours, then extracted four times with dichloromethane. The combined organic extracts were dried with $Na_2SO_4$ and evaporated to afford aminocyanacetic acid ethyl ester as a light yellow oil (11.80 g, 44%).

C) A solution of aminocyanacetic acid ethyl ester (1.00 g, 7.80 mmol) in ethyl acetate (16.00 ml) was cooled to 0° C. and treated with dimethylaminopyridine (0.09 g, 0.78 mmol) and dicyclohexylcarbodiimide (1.93 g, 9.36 mmol). 3-Methoxypropionic acid (0.81 g, 7.80 mmol) was added portionwise. After completed addition, the mixture was stirred at 0° C. for 1 h) then at room temperature for 3 h. The precipitated dicyclohexylurea was filtered off and the mother liquors washed with water, dried over sodium sulphate and evaporated. The residue was purified by trituration in diisopropylether to yield cyano-(3-methoxy-propionylamino)-acetic acid ethyl ester (1.27 g, 76%), MS (ISP): m/e=215.3 (M+H$^+$).

D) A suspension of cyano-(3-methoxy-propionylamino)-acetic acid ethyl ester (0.95 g, 4.44 mmol) in toluene (11.00 ml) was flushed with argon. 2,4-bis(4-Methoxyphenyl)-1,3,2,4-dithiadiphosphetane 2,4-disulfide (Lawesson's reagent) (0.90 g, 2.22 mmol) was added at once and the mixture was warmed at 110° C. for 2 h. Toluene was evaporated and the residue purified by flash chromatography (heptane/ethyl acetate) to yield 5-amino-2-(2-methoxy-ethyl)-thiazole-4-carboxylic acid ethyl ester (0.42 g, 40%), MS (ISP): m/e=231.1 (M+H$^+$).

E) A microwave vial was charged with Pd$_2$dba$_3$-chloroform complex (0.09 g, 0.09 mmol), Xantphos (0.17 g, 0.30 mmol) and cesium carbonate (1.00 g, 3.06 mmol), sealed and flushed with argon. A solution of 5-amino-2-(2-methoxy-ethyl)-thiazole-4-carboxylic acid ethyl ester (0.40 g, 1.75 mmol) and 3-bromopyridine (0.28 g, 1.75 mmol) in dioxane (5.80 ml) was degassed by sonicating and bubbling with argon, then transferred to the reaction vial. After stirring at room temperature for 5 min, the reaction mixture was irradiated in a microwave oven at 150° C. for 10 min. The mixture was diluted with THF, filtered and the mother liquors evaporated. The residue was purified by flash chromatography (heptane/ethyl acetate/methanol) to yield 2-(2-methoxy-ethyl)-5-(pyridin-3-ylamino)-thiazole-4-carboxylic acid ethyl ester (0.18 g, 40%), MS (ISP): m/e=308.3 (M+H$^+$).

F) A solution of 2-(2-methoxy-ethyl)-5-(pyridin-3-ylamino)-thiazole-4-carboxylic acid ethyl ester (0.17 g, 0.56 mmol) in methanol (1.00 ml) was treated with a 2.55 N solution of KOH in water (0.66 ml). The mixture was stirred at 55° C. for 40 min, then the volatiles were evaporated. The residue was redissolved in water (1.30 ml) and acidified to pH 3 with 1N HCl. Filtration and drying under vacuum afforded 2-(2-methoxy-ethyl)-5-(pyridin-3-ylamino)-thiazole-4-carboxylic acid (0.08 g, 50%), MS (ISP): m/e=278.1 (M–H)

G) A solution of 2-(2-methoxy-ethyl)-5-(pyridin-3-ylamino)-thiazole-4-carboxylic acid (0.032 g, 0.11 mmol) in dimethylformamide (1.00 ml) was treated with DIPEA (0.042 g, 0.33 mmol), TBTU (0.053 g, 0.16 mmol) and 6-methyl-pyridin-2-yl-amine (0.018 g, 0.16 mmol). The mixture was stirred at room temperature overnight, then purified by direct injection in preparative HPLC (ZORBAX Eclipse XDB-C18, 21.2×50 mm, 5 μm, gradient acetonitrile/water+0.1% formic acid). The tide compound (0.011 g, 27%) was obtained as a white solid, MS (ISP): m/e=370.1 (M+H$^+$).

Example 153

2-Methoxymethyl-5-(pyridin-3-ylamino)-thiazole-4-carboxylic acid (6-methyl-pyridin-2-yl)-amide The title compound, MS (ISP): m/e=356.4 (M+H$^+$), was prepared as for example 152, steps A to G. Step C was substituted with an alternative coupling procedure as follows.

A solution of aminocyanacetic acid ethyl ester (1.00 g, 7.80 mmol) in dichloromethane (15.00 ml) was cooled to 0° C. and treated with pyridine (0.62 g, 7.80 mmol). Methoxy-acetyl chloride (0.85 g, 7.80 mmol) was added dropwise during 15 min. The mixture was stirred for 5 min at 0° C., then warmed to room temperature and stirred for 10 min. The volatiles were evaporated, and the residue was redissolved in dichloromethane and washed twice with water. The organic layer was dried with sodium sulphate and evaporated. The residue was triturated in diisopropyl ether to yield cyano-(2-methoxy-acetylamino)-acetic acid ethyl ester (1.04 g, 66%), MS (ISP): m/e=201.1 (M+H$^+$).

Cyano-(2-methoxy-acetylamino)-acetic acid ethyl ester was cyclized to 5-amino-2-methoxymethyl-thiazole-4-carboxylic acid ethyl ester in step D, which was used in step E to generate 2-methoxymethyl-5-(pyridin-3-ylamino)-thiazole-4-carboxylic acid ethyl ester. This was hydrolized to 2-methoxymethyl-5-(pyridin-3-ylamino)-thiazole-4-carboxylic acid in step F, which was used in step G to generate the title compound.

Example 154

2-Cyclopropyl-5-(pyridin-3-ylamino)-thiazole-4-carboxylic acid (6-methyl-pyridin-2-yl)-amide The title compound, MS (ISP): m/e=352.3 (M+H$^+$), was prepared as for example 153, steps A to G. Step C was performed using cyclopropanecarbonyl chloride, and yielded cyano-(cyclopropanecarbonyl-amino)-acetic acid ethyl ester, which was cyclized to 5-amino-2-cyclopropyl-thiazole-4-carboxylic acid ethyl ester in step D. This was used in step E to generate 2-cyclopropyl-5-(pyridin-3-ylamino)-thiazole-4-carboxylic acid ethyl ester, which was hydrolized to 2-cyclopropyl-5-(pyridin-3-ylamino)-thiazole-4-carboxylic acid in step F. Coupling as described in step G generated the title compound.

Example 155

2-Cyclobutyl-5-(pyridin-3-ylamino)-thiazole-4-carboxylic acid (6-methyl-pyridin-2-yl)-amide The title compound, MS (ISP): m/e=366.0 (M+H$^+$), was prepared as for example 153, steps A to G. Step C was performed using cyclobutanecarbonyl chloride, and yielded cyano-(cyclobutanecarbonyl-amino)-acetic acid ethyl ester, which was cyclized to 5-amino-2-cyclobutyl-thiazole-4-carboxylic acid ethyl ester in step D. This was used in step E to generate 2-cyclobutyl-5-(pyridin-3-ylamino)-thiazole-4-carboxylic acid ethyl ester, which was hydrolized to 2-cyclobutyl-5-(pyridin-3-ylamino)-thiazole-4-carboxylic acid in step F. Coupling as described in step G generated the title compound.

Example 156

2-Ethyl-5-(pyridin-3-ylamino)-thiazole-4-carboxylic acid (6-methyl-pyridin-2-yl)-amide The title compound, MS (ISP): m/e=340.3 (M+H$^+$), was prepared as for example 153, steps A to G. Step C was performed using propionyl chloride, and yielded cyano-propionylamino-acetic acid ethyl ester, which was cyclized to 5-amino-2-ethyl-thiazole-4-carboxylic acid ethyl ester in step D. This was used in step E to generate 2-ethyl-5-(pyridin-3-ylamino)-thiazole-4-carboxylic acid ethyl ester, which was hydrolized to 2-ethyl-5-(pyridin-3-ylamino)-thiazole-4-carboxylic acid in step F. Coupling as described in step G generated the title compound.

Example 157

2-Propyl-5-(pyridin-3-ylamino)-thiazole-4-carboxylic acid (6-methyl-pyridin-2-yl)-amide The title compound, MS (ISP): m/e=354.0 (M+H$^+$), was prepared as for example 153, steps A to G. Step C was performed using butyryl chloride, and yielded butyrylaminocyano-acetic acid ethyl ester, which was cyclized to 5-amino-2-propyl-thiazole-4-carboxylic acid ethyl ester in step D. This was used in step E to generate 2-propyl-5-(pyridin-3-ylamino)-thiazole-4-carboxylic acid ethyl ester, which was hydrolized to 2-propyl-5-(pyridin-3-ylamino)-thiazole-4-carboxylic acid in step F. Coupling as described in step G generated the title compound.

Example 158

2-Isopropyl-5-(pyridin-3-ylamino)-thiazole-4-carboxylic acid (6-methyl-pyridin-2-yl)-amide The title compound, MS (ISP): m/e=352.3 (M+H$^+$), was prepared as for example 153, steps A to G. Step C was performed using isobutyryl chloride, and yielded cyano-isobutyrylamino-acetic acid ethyl ester, which was cyclized to 5-amino-2-isopropyl-thiazole-4-carboxylic acid ethyl ester in step D. This was used in step E to generate 2-isopropyl-5-(pyridin-3-ylamino)-thiazole-4-carboxylic acid ethyl ester, which was hydrolized to 2-isopropyl-5-(pyridin-3-ylamino)-thiazole-4-carboxylic acid in step F. Coupling as described in step G generated the title compound.

Example 159

2-Methyl-5-(2-methyl-pyridin-3-ylamino)-thiazole-4-carboxylic acid (5-fluoro-pyridin-2-yl)-amide The title compound was prepared as illustrated in scheme 7.

A) A solution of 5-bromo-2-methyl-thiazole-4-carboxylic acid (prepared as described in example 119, steps A to B) (1.50 g, 6.75 mmol) in methanol (80.00 ml) was treated with a saturated solution of HCl in ether (3.00 ml). The reaction mixture was heated at reflux for 3 h, then the volatiles were removed. The residue was purified by flash chromatography (methylene chloride/methanol) yielding 5-bromo-2-methyl-thiazole-4-carboxylic acid methyl ester (1.30 g, 82%) as a white solid, MS (ISP): m/e=235.9, 237.9 (M+H$^+$).

B) A solution of 2-amino-5-fluoropyridine (6.0 g, 53 mmol) in 40 ml dry dioxane was treated at 0° C. with trimethylaluminium (2M in hexane, 26.8 ml, 53 mmol). The mixture was stirred at room temperature for 1 h. A solution of 5-bromo-2-methyl-thiazole-4-carboxylic acid methyl ester (4.2 g, 18 mmol) in 40 mL dry dioxane was added and the reaction mixture was refluxed for 4 h. 10 ml water and 10 g sodium sulfate were sequentially added and filtered. The filtrate was evaporated and the residue purified by flash chromatography (hetane, ethyl acetate) to yield 5-bromo-2-methyl-thiazole-4-carboxylic acid (5-fluoro-pyridin-2-yl)-amide (3.0 g, 53%) as a white solid, MS (ISP): m/e=318.0 (M+H$^+$).

C) A solution of 5-bromo-2-methyl-thiazole-4-carboxylic acid (5-fluoro-pyridin-2-yl)-amide (0.24 g, 0.76 mmol) and 2-methyl-pyridin-3-ylamine (0.099 g, 0.92 mmol) in dry dioxane (12 ml) was degassed by sonication and argon bubbling. 4,5-Bis(diphenylphosphino)-9,9-dimethylxanthene (Xantphos) (0.149 g, 0.26 mmol) and palladium dibenzylideneacetone chloroform complex (0.081 g, 0.08 mmol) were added and the mixture was stirred until dissolution was complete. Finally, the mixture was treated with cesium carbonate (0.495 g, 1.52 mmol) and irradiated in a microwave oven at 100° C. for 10 min, 130° C. for 10 min and 150° C. for 10 min. The solvent was removed under vacuum and the residue purified by flash chromatography (heptane, ethyl acetate) to yield the title compound (0.178 g, 68%) as a light brown solid, MS (ISP): m/e=344.0 (M+H$^+$).

Example 160

5-(2-Fluoro-5-methanesulfonyl-phenylamino)-2-methyl-thiazole-4-carboxylic acid (2-methyl-pyridin-4-yl)-amide The title compound, MS (ISP): m/e=421.1 (M+H$^+$), was prepared as for example 159, steps A to C. Step B was performed using 2-methyl-pyridin-4-ylamine and step C was performed using 2-fluoro-5-methylsulfonyl-aniline.

Example 161

2-Methyl-5-(3-sulfamoyl-phenylamino)-thiazole-4-carboxylic acid (2-methyl-pyridin-4-yl)-amide The title compound, MS (ISP): m/e=404.4 (M+H$^+$), was prepared as for example 159, steps A to C. Step B was performed using 2-methyl-pyridin-4-ylamine and step C was performed using 3-aminobenzene sulfonamide.

Example 162

2-Methyl-5-((6-trifluoromethyl-pyridin-3-yl)amino)-thiazole-4-carboxylic acid (2-methyl-pyridin-4-yl)-amide The title compound, MS (ISP): m/e=394.0 (M+H$^+$), was prepared as for example 159, steps A to C. Step B was performed using 2-methyl-pyridin-4-ylamine and step C was performed using 3-amino-6-(trifluoromethyl)pyridine.

Example 163

2-Methyl-5-(3-sulfamoyl-phenylamino)-thiazole-4-carboxylic acid (5-fluoro-pyridin-2-yl)-amide The title compound was prepared as illustrated in scheme 8.

A) A suspension of 2-acetylamino-cyanoacetic acid ethyl ester (1.70 g, 10.00 mmol) and 2,4-bis(4-methoxyphenyl)-1,3,2,4-dithiadiphosphetane 2,4-disulfide (Lawesson's reagent) (2.02 g, 5.00 mmol) in toluene (25.00 ml) was heated under argon to 110° C. and stirred for 22 h. The solvent was then evaporated, and the residue purified by flash chromatography (heptane/ethyl acetate 1:1) to yield 5-amino-2-methyl-thiazole-4-carboxylic acid ethyl ester (0.94 g, 50.5%) as a yellow solid, MS (ISP): m/e=187.3 (M+H$^+$).

B) A microwave vial was charged with 5-amino-2-methyl-thiazole-4-carboxylic acid ethyl ester (0.300 g, 1.61 mmol), 4,5-bis(diphenylphosphino)-9,9-dimethylxanthene (Xantphos) (0.28 g, 0.48 mmol) and palladium dibenzylideneacetone (Pd$_2$dba$_3$)-chloroform complex (0.17 g, 0.16 mmol). Degassed dioxane (15.00 ml) was added, followed by 3-bromobenzenesulfonamide (0.38 g, 1.61 mmol) and cesium carbonate (0.93 g, 2.87 mmol) The vial was then irradiated in a microwave oven at 150° C. for 15 min. The mixture was diluted with THF and the solids filtered, washing with THF. The filtrate was evaporated and the residue purified by flash chromatography (heptane ethyl acetate) to yield 2-methyl-5-(3-sulfamoyl-phenylamino)-thiazole-4-carboxylic acid ethyl ester (0.13 g, 24%) as an off-white solid, MS (ISP): m/e=342.1 (M+H$^+$).

C) A solution of 2-amino-5-fluoro pyridine (0.15 g, 1.38 mmol) in 10 ml dry dioxane was treated at 0° C. with trimethylaluminium (2M in hexane, 0.69 ml, 1.38 mmol). The mixture was stirred at room temperature for 1 h. 2-Methyl-5-(3-sulfamoyl-phenylamino)-thiazole-4-carboxylic acid ethyl ester (0.12 g, 0.35 mmol) was added and the reaction mixture was refluxed for 4 h. 1 ml water and 2 g sodium sulfate were sequentially added and filtered. The filtrate was evaporated and the residue purified by flash chromatography (hetane, ethyl acetate) to yield 2-methyl-5-(3-sulfamoyl-phenylamino)-thiazole-4-carboxylic acid (5-fluoro-pyridin-2-yl)-amide (0.004 g, 3%) as an off-white solid, MS (ISP): m/e=408.4 (M+H$^+$).

Example 164

2-Methyl-5-(2-methyl-pyridin-3-ylamino)-thiazole-4-carboxylic acid (2-methyl-pyridin-4-yl)-amide The title compound, MS (ISP): m/e=340.3 (M+H$^+$), was prepared as for example 159, steps A to C. Step B was performed using 2-methyl-pyridin-4-ylamine and step C was performed using 2-methyl-pyridin-3-ylamine.

Example 165

5-(3-Methanesulfonyl-phenylamino)-2-methyl-thiazole-4-carboxylic acid (5-fluoro-pyridin-2-yl)-amide The title compound, MS (ISP): m/e=407.4 (M+H$^+$), was prepared as for example 159, steps A to C. Step B was performed using 2-amino-5-fluoro pyridine and step C was performed using 3-methylsulfonylaniline.

Example 166

2-Methyl-5-(pyrazin-2-ylamino)-thiazole-4-carboxylic acid (5-fluoro-pyridin-2-yl)-amide The title compound, MS (ISP): m/e=331.3 (M+H$^+$), was prepared as for example 159, steps A to C. Step B was performed using 2-amino-5-fluoro pyridine and step C was performed using aminopyrazine.

Example 167

5-(5-Chloro-pyridin-3-ylamino)-2-methyl-thiazole-4-carboxylic acid (5-fluoro-pyridin-2-yl)-amide The title compound, MS (ISP): m/e=364.1 (M+H$^+$), was prepared as for example 159, steps A to C. Step B was performed using 2-amino-5-fluoro pyridine and step C was performed using 5-chloropyridin-3-amine.

Example 168

2-Methyl-5-(4-methyl-pyridin-2-ylamino)-thiazole-4-carboxylic acid (5-fluoro-pyridin-2-yl)-amide The title compound, MS (ISP): m/e=344.1 (M+H$^+$), was prepared as for example 159, steps A to C. Step B was performed using 2-amino-5-fluoro pyridine and step C was performed using 2-amino-5-methylpyridine.

Example 169

5-(4-Fluoro-phenylamino)-2-methyl-thiazole-4-carboxylic acid (2-chloro-pyridin-4-yl)-amide The title compound, MS (ISP): m/e=363.3 (M+H$^+$), was prepared as for example 159, steps A to C. Step B was performed using 2-chloro-pyridin-4-ylamine and step C was performed using 4-fluoroaniline.

Example 170

2-Methyl-5-(pyrimidin-5-ylamino)-thiazole-4-carboxylic acid (2-chloro-pyridin-4-yl)-amide The title compound, MS (ISP): m/e=347.3 (M+H$^+$), was prepared as for example 159, steps A to C. Step B was performed using 2-chloro-pyridin-4-ylamine and step C was performed using 5-aminopyrimidine.

Example 171

2-Methyl-5-(2-methyl-pyridin-4-ylamino)-thiazole-4-carboxylic acid (5-fluoro-pyridin-2-yl)-amide The title compound, MS (ISP): m/e=344.1 (M+H$^+$), was prepared as for example 159, steps A to C. Step B was performed using 2-amino-5-fluoro pyridine and step C was performed using 2-methyl-pyridin-4-ylamine.

Example 172

2-Methyl-5-(2-methyl-pyridin-3-ylamino)-thiazole-4-carboxylic acid (2-chloro-pyridin-4-yl)-amide The title compound, MS (ISP): m/e=360.3 (M+H$^+$), was prepared as for example 159, steps A to C. Step B was performed using 2-chloro-pyridin-4-ylamine and step C was performed using 2-methyl-pyridin-3-ylamine.

Example 173

2-Methyl-5-(pyrazin-2-ylamino)-thiazole-4-carboxylic acid (2-chloro-pyridin-4-yl)-amide The title compound, MS (ISP): m/e=347.1 (M+H$^+$), was prepared as for example 159, steps A to C. Step B was performed using 2-chloro-pyridin-4-ylamine and step C was performed using aminopyrazine.

Example 174

5-(5-Chloro-pyridin-3-ylamino)-2-methyl-thiazole-4-carboxylic acid (2-methyl-pyridin-4-yl)-amide The title compound, MS (ISP): m/e=360.4 (M+H$^+$), was prepared as for example 159, steps A to C. Step B was performed using 2-methyl-pyridin-4-ylamine and step C was performed using 5-chloropyridin-3-amine.

Example 175

5-((3-Difluoromethoxy-phenyl)amino)-2-methyl-thiazole-4-carboxylic acid (5-fluoro-pyridin-2-yl)-amide The title compound, MS (ISP): m/e=395.0 (M+H$^+$), was prepared as for example 159, steps A to C. Step B was performed using 2-amino-5-fluoro pyridine and step C was performed using 3-(difluoromethoxy)aniline.

Example 176

5-(3-Diethylsulfamoyl-phenylamino)-2-methyl-thiazole-4-carboxylic acid (5-fluoro-pyridin-2-yl)-amide The title compound, MS (ISP): m/e=464.4 (M+H$^+$), was prepared as for example 159, steps A to C. Step B was performed using 2-amino-5-fluoro pyridine and step C was performed using 3-amino-N,N-diethyl-benzenesulfonamide.

Example 177

5-(5-Chloro-pyridin-3-ylamino)-2-methyl-thiazole-4-carboxylic acid (2-chloro-pyridin-4-yl)-amide The title compound, MS (ISP): m/e=380.1 (M+H$^+$), was prepared as for example 159, steps A to C. Step B was performed using 2-chloro-pyridin-4-ylamine and step C was performed using 5-chloropyridin-3-amine.

Example 178

5-(5-Cyano-pyridin-3-ylamino)-2-methyl-thiazole-4-carboxylic acid (5-fluoro-pyridin-2-yl)-amide The title compound, MS (ISP): m/e=355.3 (M+H$^+$), was prepared as for example 163, steps A to C. Step B was performed using 5-bromopyridine-3-carbonitrile and step C was performed using 2-amino-5-fluoro pyridine.

Example 179

5-(5-Cyano-pyridin-3-ylamino)-2-methyl-thiazole-4-carboxylic acid (2-methyl-pyrimidin-4-yl)-amide The title compound, MS (ISP): m/e=352.3 (M+H$^+$), was prepared as for example 163, steps A to C. Step B was performed using 5-bromopyridine-3-carbonitrile and step C was performed using 2-methyl-4-amino-pyrimidine.

Example 180

2-Methyl-5-(4-methyl-pyridin-3-ylamino)-thiazole-4-carboxylic acid (5-fluoro-pyridin-2-yl)-amide The title compound, MS (ISP): m/e=344.0 (M+H$^+$), was prepared as for example 163, steps A to C. Step B was performed using 3-bromo-4-methylpyridine and step C was performed using 2-amino-5-fluoro pyridine.

Example 181

2-Methyl-5-(pyrimidin-5-ylamino)-thiazole-4-carboxylic acid (2-methyl-pyrimidin-4-yl)-amide The title compound, MS (ISP): m/e=328.3 (M+H$^+$), was prepared as for example 159, steps A to C. Step B was performed using 2-methyl-4-amino-pyrimidine and step C was performed using 5-aminopyrimidine.

Example 182

5-(5-Cyano-pyridin-3-ylamino)-2-methyl-thiazole-4-carboxylic acid (2-methyl-pyridin-4-yl)-amide The title compound, MS (ISP): m/e=351.4 (M+H$^+$), was prepared as for example 163, steps A to C. Step B was performed using 5-bromopyridine-3-carbonitrile and step C was performed using 2-methyl-pyridin-4-ylamine.

Example 183

5-(5-Cyano-pyridin-3-ylamino)-2-methyl-thiazole-4-carboxylic acid (4-methyl-pyrimidin-2-yl)-amide The title compound, MS (ISP): m/e=352.3 (M+H$^+$), was prepared as for example 163, steps A to C. Step B was performed using 5-bromopyridine-3-carbonitrile and step C was performed using 2-amino-4-methylpyrimidine.

Example 184

2-Methyl-5-(3-oxazol-5-yl-phenylamino)-thiazole-4-carboxylic acid (2-methyl-pyrimidin-4-yl)-amide The title compound, MS (ISP): m/e=393.1 (M+H$^+$), was prepared as for example 159, steps A to C. Step B was performed using 2-methyl-4-amino-pyrimidine and step C was performed using 3-(1,3-oxazol-5-yl)aniline.

Example 185

2-Methyl-5-(4-methyl-pyridin-3-ylamino)-thiazole-4-carboxylic acid (2-chloro-pyridin-4-yl)-amide The title compound, MS (ISP): m/e=360.3 (M+H$^+$), was prepared as for example 163, steps A to C. Step B was performed using 3-bromo-4-methylpyridine and step C was performed using 4-amino-2-chloropyridine.

Example 186

5-(5-Methanesulfonyl-pyridin-3-ylamino)-2-methyl-thiazole-4-carboxylic acid (2-methyl-pyridin-4-yl)-amide The title compound, MS (ISP): m/e=404.4 (M+H$^+$), was prepared as for example 163, steps A to C. Step B was performed using 3-bromo-5-methanesulfonyl-pyridine and step C was performed using 2-methyl-pyridin-4-ylamine.

Example 187

5-(3-Fluoro-phenylamino)-2-methyl-thiazole-4-carboxylic acid (2-methyl-pyrimidin-4-yl)-amide The title compound, MS (ISP): m/e=344.1 (M+H$^+$), was prepared as for example 159, steps A to C. Step B was performed using 2-methyl-4-amino-pyrimidine and step C was performed using 3-fluoro-aniline.

Example 188

2-Methyl-5-(6-methyl-pyridazin-4-ylamino)-thiazole-4-carboxylic acid (2-methyl-pyridin-4-yl)-amide The title compound, MS (ISP): m/e=341.3 (M+H$^+$), was obtained as a by-product of 2-methyl-5-(6-methyl-pyridazin-4-ylamino)-thiazole-4-carboxylic acid (2-chloro-pyridin-4-yl)-amide (example 190) through substitution of the chloro for methyl by the trimethylaluminium reagent.

Example 189

5-(3-Cyano-phenylamino)-2-methyl-thiazole-4-carboxylic acid (2-methyl-pyrimidin-4-yl)-amide The title compound, MS (ISP): m/e=351.4 (M+H$^+$), was prepared as for example 159, steps A to C. Step B was performed using 2-methyl-4-amino-pyrimidine and step C was performed using 3-aminobenzonitrile.

Example 190

2-Methyl-5-(6-methyl-pyridazin-4-ylamino)-thiazole-4-carboxylic acid (2-chloro-pyridin-4-yl)-amide The title compound, MS (ISP): m/e=361.4 (M+H$^+$), was prepared as for example 163, steps A to C. Step B was performed using 5-chloro-3-methyl-pyridazine and step C was performed using 4-amino-2-chloropyridine.

Example 191

5-(3-Ethylsulfamoyl-phenylamino)-2-methyl-thiazole-4-carboxylic acid (5-fluoro-pyridin-2-yl)-amide The title compound, MS (ISP): m/e=436.1 (M+H$^+$), was prepared as for example 159, steps A to C. Step B was performed using 2-amino-5-fluoro pyridine and step C was performed using 3-amino-N-ethyl-benzenesulfonamide.

Example 192

5-(Isoxazol-3-ylamino)-2-methyl-thiazole-4-carboxylic acid (2-methyl-pyrimidin-4-yl)-amide The title compound, MS (ISP): m/e=317.3 (M+H$^+$), was prepared as for example 159, steps A to C. Step B was performed using 2-methyl-4-amino-pyrimidine and step C was performed using 3-aminoisoxazole.

Example 193

5-(4-Cyano-pyridin-2-ylamino)-2-methyl-thiazole-4-carboxylic acid (2-methyl-pyridin-4-yl)-amide The title compound, MS (ISP): m/e=351.3 (M+H$^+$), was prepared as for example 159, steps A to C. Step B was performed using 2-methyl-pyridin-4-ylamine and step C was performed using 2-amino-isonicotinonitrile.

Example 194

5-(3,5-Difluoro-phenylamino)-2-methyl-thiazole-4-carboxylic acid (2-methyl-pyrimidin-4-yl)-amide The title compound, MS (ISP): m/e=362.3 (M+H$^+$), was prepared as for example 159, steps A to C. Step B was performed using 2-methyl-4-amino-pyrimidine and step C was performed using 3,5-difluoro-aniline.

Example 195

5-(2-Chloro-pyridin-4-ylamino)-2-methyl-thiazole-4-carboxylic acid (2-methyl-pyridin-4-yl)-amide The title compound, MS (ISP): m/e=360.0 (M+H$^+$), was prepared as for example 159, steps A to C. Step B was performed using 2-methyl-pyridin-4-ylamine and step C was performed using 4-amino-2-chloropyridine.

Example 196

5-(4-Chloro-pyridin-2-ylamino)-2-methyl-thiazole-4-carboxylic acid (2-methyl-pyrimidin-4-yl)-amide The title compound, MS (ISP): m/e=361.0 (M+H$^+$), was prepared as for example 159, steps A to C. Step B was performed using 2-methyl-pyridin-4-ylamine and step C was performed using 4-chloro-pyridin-2-ylamine.

Example 197

2-Methyl-5-(pyrimidin-5-ylamino)-thiazole-4-carboxylic acid (3-chloro-4-fluoro-phenyl)-amide The title compound, MS (ISP): m/e=364.0 (M+H$^+$), was prepared as for example 163, steps A to C. Step B was performed using 5-bromopyrimidine and step C was performed using 3-chloro-4-fluoro-aniline.

Example 198

5-(5-Methanesulfonyl-pyridin-3-ylamino)-2-methyl-thiazole-4-carboxylic acid (6-fluoro-pyridin-3-yl)-amide The title compound, MS (ISP): m/e=408.3 (M+H$^+$), was prepared as for example 163, steps A to C. Step B was performed using 3-bromo-5-methanesulfonyl-pyridine and step C was performed using 2-amino-5-fluoropyridine.

Example 199

5-(5-Methanesulfonyl-pyridin-3-ylamino)-2-methyl-thiazole-4-carboxylic acid (2-methyl-pyrimidin-4-yl)-amide The title compound, MS (ISP): m/e=405.4 (M+H$^+$), was prepared as for example 163, steps A to C. Step B was performed using 3-bromo-5-methanesulfonyl-pyridine and step C was performed using 2-methyl-4-amino-pyrimidine.

Example 200

5-(3-Methanesulfonyl-phenylamino)-2-methyl-thiazole-4-carboxylic acid (2-methyl-pyrimidin-4-yl)-amide The title compound, MS (ISP): m/e=404.4 (M+H$^+$), was prepared as for example 159, steps A to C. Step B was performed using 2-methyl-4-amino-pyrimidine and step C was performed using 3-methylsulphonylaniline.

Example 201

5-(3-Fluoro-phenylamino)-2-methyl-thiazole-4-carboxylic acid (2-methyl-pyridin-4-yl)-amide The tide compound, MS (ISP): m/e=343.1 (M+H$^+$), was prepared as for example 159, steps A to C. Step B was performed using 2-methyl-pyridin-4-ylamine and step C was performed using 3-fluoroaniline.

Example 202

5-(3,5-Difluoro-phenylamino)-2-methyl-thiazole-4-carboxylic acid (2-methyl-pyridin-4-yl)-amide The title compound, MS (ISP): m/e=361.4 (M+H$^+$), was prepared as for example 159, steps A to C. Step B was performed using 2-methyl-pyridin-4-ylamine and step C was performed using 3,5-difluoroaniline.

Example 203

2-Methyl-5-(pyrimidin-5-ylamino)-thiazole-4-carboxylic acid (4-fluoro-3-methyl-phenyl)-amide The title compound, MS (ISP): m/e=344.3 (M+H$^+$), was prepared as for example 163, steps A to C. Step B was performed using 5-bromopyrimidine and step C was performed using 4-fluoro-3-methyl-aniline.

Example 204

2-Methyl-5-(pyridin-3-ylamino)-thiazole-4-carboxylic acid (2-ethyl-pyrimidin-4-yl)-amide The title compound, MS (ISP): m/e=341.3 (M+H$^+$), was prepared as for example 163, steps A to C. Step B was performed using 3-bromopyridine and step C was performed using 2-ethyl-4-amino-pyrimidine.

Example 205

Cyclopropylmethyl-[2-methyl-4-(2-methyl-pyrimidin-4-ylcarbamoyl)-thiazol-5-yl]-carbamic acid cyclopropylmethyl ester A) A suspension of 2-acetylamino-cyanoacetic acid ethyl ester (1.70 g, 10.00 mmol) and 2,4-bis(4-methoxyphenyl)-1,3,2,4-dithiadiphosphetane 2,4-disulfide (Lawesson's reagent) (2.02 g, 5.00 mmol) in toluene (25.00 ml) was heated under argon to 110° C. and stirred for 22 h. The solvent was then evaporated, and the residue purified by flash chromatography (heptane/ethyl acetate 1:1) to yield 5-amino-2-methyl-thiazole-4-carboxylic acid ethyl ester (0.94 g, 50.5%) as a yellow solid, MS (ISP): m/e=187.3 (M+H$^+$).

B) 5-Amino-2-methyl-thiazole-4-carboxylic acid ethyl ester (0.200 g, 1.07 mmol) was dissolved in 10 mL dry DMF. Potassium carbonate (0.45 g, 3.26 mmol) and cyclopropyl methylbromide (0.166 g, 1.23 mmol) were added and the reaction mixture was stirred at 80° C. overnight. The reaction mixture was diluted with 100 mL water and extracted three times with ethyl acetate (50 mL each). The organic phases were pooled, dried with sodium sulfate and evaporated. The crude product was flash-chromatographed on silica gel with heptane/ethyl acetate 100:0→0:100 gradient to yield 5-(cyclopropylmethoxycarbonyl-(cyclopropylmethyl)-amino)-2-methyl-thiazole-4-carboxylic acid ethyl ester (140 mg, 39%).

C) A solution of 2-methyl-4-amino-pyrimidine (0.184 g, 1.68 mmol) in 10 ml dry dioxane was treated at 0° C. with trimethylaluminium (2M in hexane, 0.84 ml, 1.68 mmol). The mixture was stirred at room temperature for 1 h. 5-(Cyclopropylmethoxycarbonyl-(cyclopropylmethyl)-amino)-2-methyl-thiazole-4-carboxylic acid ethyl ester (0.135 g, 0.40 mmol) was added and the reaction mixture was refluxed for 4 h. 1 ml water and 2 g sodium sulfate were sequentially added and filtered. The filtrate was evaporated and the residue purified by flash chromatography with heptane/ethyl acetate 100:0→0:100 gradient to yield cyclopropylmethyl-[2-methyl-4-(2-methyl-pyrimidin-4-ylcarbamoyl)-thiazol-5-yl]-carbamic acid cyclopropylmethyl ester (0.101 g, 63%) as a colourless oil, MS (ISP): m/e=402.5 (M+H$^+$).

Example 206

2-Methyl-5-(5-methyl-pyridin-3-ylamino)-thiazole-4-carboxylic acid (5-fluoro-pyridin-2-yl)-amide The title compound, MS (ISP): m/e=344.1 (M+H$^+$), was prepared as for example 163, steps A to C. Step B was performed using 3,5-dichloropyridine and step C was performed using 2-amino-5-fluoropyridine. The chloro was substituted by methyl through the trimethylaluminium reagent.

Example 207

5-(2-Chloro-pyridin-4-ylamino)-2-methyl-thiazole-4-carboxylic acid (2-methyl-pyrimidin-4-yl)-amide The title compound, MS (ISP): m/e=361.4 (M+H$^+$), was prepared as for example 159, steps A to C. Step B was performed using 2-methyl-4-amino-pyrimidine and step C was performed using 4-amino-2-chloroaniline.

Example 208

5-(((Cyclopropylmethyl)-amino)-2-methyl-thiazole-4-carboxylic acid (2-methyl-pyrimidin-4-yl)-amide Cyclopropylmethyl-[2-methyl-4-(2-methyl-pyrimidin-4-ylcarbamoyl)-thiazol-5-yl]-carbamic acid cyclopropylmethyl ester (example 205, 0.091 g, 0.227 mmol) was dissolved in 1 mL trifluoroacetic acid and stirred at 50° C. for 3 h. The reaction mixture was diluted with 20 mL saturated sodium bicarbonate solution and extracted three times with ethyl acetate (30 mL each). The organic phases were pooled, dried with sodium sulfate and evaporated. The crude product was flash-chromatographed on silica gel with heptane/ethyl acetate 100:0→0:100 gradient to yield the desired compound as a white solid (37 mg, 54%), MS (ISP): m/e=304.0 (M+H$^+$).

Example 209

5-(3-Carbamoyl-phenylamino)-2-methyl-thiazole-4-carboxylic acid (2-methyl-pyrimidin-4-yl)-amide The title compound, MS (ISP): m/e=369.0 (M+H$^+$), was prepared as for example 159, steps A to C. Step B was performed using 2-methyl-4-amino-pyrimidine and step C was performed using 3-aminobenzamide.

Example 210

2-Methyl-5-((3-trifluoromethyl-phenyl)amino)-thiazole-4-carboxylic acid (2-methyl-pyridin-4-yl)-amide The title compound, MS (ISP): m/e=393.1 (M+H$^+$), was prepared as for example 159, steps A to C. Step B was performed using 2-methyl-pyridin-4-ylamine and step C was performed using 3-aminobenzotrifluoride.

Example 211

5-(3-Carbamoyl-phenylamino)-2-methyl-thiazole-4-carboxylic acid (2-methyl-pyridin-4-yl)-amide The title compound, MS (ISP): m/e=368.1 (M+H$^+$), was prepared as for example 159, steps A to C. Step B was performed using 2-methyl-pyridin-4-ylamine and step C was performed using 3-aminobenzamide.

Example 212

5-(5-Methoxy-pyridin-3-ylamino)-2-methyl-thiazole-4-carboxylic acid (2-methyl-pyridin-4-yl)-amide The title compound, MS (ISP): m/e=356.3 (M+H$^+$), was prepared as for example 159, steps A to C. Step B was performed using 5-bromo-3-methoxy-pyridine and step C was performed using 2-methyl-pyridin-4-ylamine.

Example 213

2-Methyl-5-(5-methyl-pyridin-3-ylamino)-thiazole-4-carboxylic acid (2-methyl-pyridin-4-yl)-amide The title compound, MS (ISP): m/e=340.3 (M+H$^+$), was prepared as for example 159, steps A to C. Step B was performed using 5-bromo-3-picoline and step C was performed using 2-methyl-pyridin-4-ylamine.

Example 214

5-(5-Fluoro-pyridin-3-ylamino)-2-methyl-thiazole-4-carboxylic acid (2-methyl-pyridin-4-yl)-amide The title compound was prepared as illustrated in scheme 9.

A) A suspension of 2-acetylamino-cyanoacetic acid ethyl ester (1.70 g, 10.00 mmol) and 2,4-bis(4-methoxyphenyl)-1,3,2,4-dithiadiphosphetane 2,4-disulfide (Lawesson's reagent) (2.02 g, 5.00 mmol) in toluene (25.00 ml) was heated under argon to 110° C. and stirred for 22 h. The solvent was then evaporated, and the residue purified by flash chromatography (heptane/ethyl acetate 1:1) to yield 5-amino-2-methyl-thiazole-4-carboxylic acid ethyl ester (0.94 g, 50.5%) as a yellow solid, MS (ISP): m/e=187.3 (M+H$^+$).

B) 5-Amino-2-methyl-thiazole-4-carboxylic acid ethyl ester (0.40 g, 2.15 mmol) was dissolved in 20 ml dry THF. Di-tert.-butyl dicarbonate (0.526 g, 4.41 mmol) and 4-(N,N-dimethylamino)pyridine (0.036 g, 0.3 mmol) were added and the reaction mixture was stirred at 70° C. overnight. The solvent was evaporated, the residue taken up in 20 mL saturated sodium bicarbonate solution and extracted three times with ethyl acetate (30 mL each). The organic phases were pooled, dried with sodium sulfate and evaporated. The crude product was flash-chromatographed on silica gel with heptane/ethyl acetate 100:0→0:100 gradient to yield 5-tert-butoxycarbonylamino-2-methyl-thiazole-4-carboxylic acid ethyl ester as a light yellow solid (0.553 g, 90%), MS (ISP): m/e=287.1 (M+H$^+$).

C) A solution of 2-methyl-pyridin-4-ylamine (0.623 g, 5.77 mmol) in 20 ml dry dioxane was treated at 0° C. with trimethylaluminium (2M in hexane, 2.88 ml, 5.77 mmol). The mixture was stirred at room temperature for 1 h. 5-tert-Butoxycarbonylamino-2-methyl-thiazole-4-carboxylic acid ethyl ester (0.55 g, 1.92 mmol) was added and the reaction mixture was refluxed for 4 h. 1 ml water and 2 g sodium sulfate were sequentially added and filtered. The filtrate was evaporated and the residue purified by flash chromatography on silica gel with heptane/ethyl acetate 100:0→0:100 to yield [2-methyl-4-(2-methyl-pyridin-4-ylcarbamoyl)-thiazol-5-yl]-carbamic acid tert-butyl ester (0.555 g, 83%) as a light yellow solid, MS (ISP): m/e=349.5 (M+H$^+$).

D) [2-Methyl-4-(2-methyl-pyridin-4-ylcarbamoyl)-thiazol-5-yl]-carbamic acid tert-butyl ester (0.532 g, 1.53 mmol) was dissolved in 12 mL trifluoroacetic acid and stirred at room temperature for 30 min. The reaction mixture was treated with 2N sodium carbonate solution until pH 10 and extracted three times with ethyl acetate (50 mL each). The organic phases were pooled, dried with sodium sulfate and evaporated. The crude product was flash-chromatographed on silica gel with heptane/ethyl acetate 100:0→0:100 gradient to yield 5-amino-2-methyl-thiazole-4-carboxylic acid (2-methyl-pyridin-4-yl)-amide as a light yellow solid (0.361 g, 95%), MS (ISP): m/e=249.1 (M+H$^+$).

E) 5-Amino-2-methyl-thiazole-4-carboxylic acid (2-methyl-pyridin-4-yl)-amide (0.15 g, 0.605 mmol) was dissolved in 5 mL fry DMF. 3,5-Difluoropyridine (0.213 g, 1.85 mmol) and cesium carbonate (0.59 g, 1.85 mmol) were added. The reaction mixture was irradiated in the microwave at 150° C. for 45 min, diluted with 100 mL water and extracted three times with ethyl acetate (50 mL each). The organic phases were pooled, dried with sodium sulfate and evaporated. The crude product was flash-chromatographed on silica gel with heptane/ethyl acetate 100:0→0:100 gradient to yield the title compound as an off-white solid (0.135 g, 65%), MS (ISP): m/e=344.1 (M+H$^+$).

Example 215

5-(3-Cyano-phenylamino)-2-methyl-thiazole-4-carboxylic acid (2-methyl-pyridin-4-yl)-amide The title compound, MS (ISP): m/e=350.4 (M+H$^+$), was prepared as for example 159, steps A to C. Step B was performed using 2-methyl-pyridin-4-ylamine and step C was performed using 3-aminobenzonitrile.

Example 216

2-Methyl-5-(2-methyl-2H-pyrazol-3-ylamino)-thiazole-4-carboxylic acid (2-methyl-pyridin-4-yl)-amide The title compound, MS (ISP): m/e=329.0 (M+H$^+$), was prepared as for example 159, steps A to C. Step B was performed using 2-methyl-pyridin-4-ylamine and step C was performed using 5-amino-1-methylpyrazole.

Example 217

3-[2-Methyl-4-(2-methyl-pyridin-4-ylcarbamoyl)-thiazol-5-ylamino]-benzoic acid methyl ester The title compound, MS (ISP): m/e=383.1 (M+H$^+$), was prepared as for example 159, steps A to C. Step B was performed using 2-methyl-pyridin-4-ylamine and step C was performed using methyl-3-aminobenzoate.

Example 218

5-(2,5-Difluoro-phenylamino)-2-methyl-thiazole-4-carboxylic acid (2-methyl-pyridin-4-yl)-amide The title compound, MS (ISP): m/e=361.4 (M+H$^+$), was prepared as for example 159, steps A to C. Step B was performed using 2-methyl-pyridin-4-ylamine and step C was performed using 2,5-difluoroaniline.

Example 219

2-Methyl-5-(pyridin-3-ylamino)-thiazole-4-carboxylic acid (4-methyl-pyrimidin-2-yl)-amide The title compound, MS (ISP): m/e=327.3 (M+H$^+$), was prepared as for example 163, steps A to C. Step B was performed using 3-bromo-pyridine and step C was performed using 2-amino-4-methylpyrimidine.

Example 220

5-(3,5-Difluoro-phenylamino)-2-methyl-thiazole-4-carboxylic acid (2-chloro-pyridin-4-yl)-amide The title compound, MS (ISP): m/e=381.0 (M+H$^+$), was prepared as for example 159, steps A to C. Step B was performed using 4-amino-2-chloropyridine and step C was performed using 3,5-difluoroaniline.

Example 221

5-(3-Hydroxymethyl-phenylamino)-2-methyl-thiazole-4-carboxylic acid (2-methyl-pyridin-4-yl)-amide 3-[2-Methyl-4-(2-methyl-pyridin-4-ylcarbamoyl)-thiazol-5-ylamino]-benzoic acid methyl ester (example 222, 0.425 g, 1.11 mmol) was dissolved in 15 mL dry THF. Lithiumalumiumhydride (0.169 g, 4.44 mmol) was added and the reaction mixture was stirred at room temperature for 1 h. Water (0.169 mL), 15% NaOH (0.169 mL) and again water (0.507 mL) was slowly added and the reaction mixture was filtered and evaporated. The crude material was recrystallized from ethyl acetate and dichloromethane to yield the title compound as a yellow solid (0.257 g, 65%), MS (ISP): m/e=355.3 (M+H$^+$).

Example 222

2-Methyl-5-(pyridin-2-ylamino)-thiazole-4-carboxylic acid (2-chloro-pyridin-4-yl)-amide The title compound, MS (ISP): m/e=346.1 (M+H$^+$), was prepared as for example 159, steps A to C. Step B was performed using 4-amino-2-chloropyridine and step C was performed using 2-aminopyridine.

Example 223

2-Methyl-5-((5-trifluoromethyl-pyridin-3-yl)amino)-thiazole-4-carboxylic acid (2-methyl-pyridin-4-yl)-amide The title compound was prepared as illustrated in scheme 9.

A) A suspension of 2-acetylamino-cyanoacetic acid ethyl ester (1.70 g, 10.00 mmol) and 2,4-bis(4-methoxyphenyl)-1,3,2,4-dithiadiphosphetane 2,4-disulfide (Lawesson's reagent) (2.02 g, 5.00 mmol) in toluene (25.00 ml) was heated under argon to 110° C. and stirred for 22 h. The solvent was then evaporated, and the residue purified by flash chromatography (heptane/ethyl acetate 1:1) to yield 5-amino-2-methyl-thiazole-4-carboxylic acid ethyl ester (0.94 g, 50.5%) as a yellow solid, MS (ISP): m/e=187.3 (M+H$^+$).

B) 5-Amino-2-methyl-thiazole-4-carboxylic acid ethyl ester (0.40 g, 2.15 mmol) was dissolved in 20 ml dry THF. Di-tert.-butyl dicarbonate (0.526 g, 4.41 mmol) and 4-(N,N-dimethylamino)pyridine (0.036 g, 0.3 mmol) were added and the reaction mixture was stirred at 70° C. overnight. The solvent was evaporated, the residue taken up in 20 mL saturated sodium bicarbonate solution and extracted three times with ethyl acetate (30 mL each). The organic phases were pooled, dried with sodium sulfate and evaporated. The crude product was flash-chromatographed on silica gel with heptane/ethyl acetate 100:0→0:100 gradient to yield 5-tert-butoxycarbonylamino-2-methyl-thiazole-4-carboxylic acid ethyl ester as a light yellow solid (0.553 g, 90%), MS (ISP): m/e=287.1 (M+H$^+$).

C) A solution of 2-methyl-pyridin-4-ylamine (0.623 g, 5.77 mmol) in 20 ml dry dioxane was treated at 0° C. with trimethylaluminium (2M in hexane, 2.88 ml, 5.77 mmol). The mixture was stirred at room temperature for 1 h. 5-tert-Butoxycarbonylamino-2-methyl-thiazole-4-carboxylic acid ethyl ester (0.55 g, 1.92 mmol) was added and the reaction mixture was refluxed for 4 h. 1 ml water and 2 g sodium sulfate were sequentially added and filtered. The filtrate was evaporated and the residue purified by flash chromatography on silica gel with heptane/ethyl acetate 100:0→0:100 to yield [2-methyl-4-(2-methyl-pyridin-4-ylcarbamoyl)-thiazol-5-yl]-carbamic acid tert-butyl ester (0.555 g, 83%) as a light yellow solid, MS (ISP): m/e=349.5 (M+H$^+$).

D) [2-Methyl-4-(2-methyl-pyridin-4-ylcarbamoyl)-thiazol-5-yl]-carbamic acid tert-butyl ester (0.532 g, 1.53 mmol) was dissolved in 12 mL trifluoroacetic acid and stirred at room temperature for 30 min. The reaction mixture was treated with 2N sodium carbonate solution until pH 10 and extracted three times with ethyl acetate (50 mL each). The organic phases were pooled, dried with sodium sulfate and evaporated. The crude product was flash-chromatographed on silica gel with heptane/ethyl acetate 100:0→0:100 gradient to yield 5-amino-2-methyl-thiazole-4-carboxylic acid (2-methyl-pyridin-4-yl)-amide as a light yellow solid (0.361 g, 95%), MS (ISP): m/e=249.1 (M+H$^+$).

E) A microwave vial was charged with 5-amino-2-methyl-thiazole-4-carboxylic acid (2-methyl-pyridin-4-yl)-amide (0.200 g, 0.806 mmol), 4,5-bis(diphenylphosphino)-9,9-dimethylxanthene (Xantphos) (0.159 g, 0.275 mmol) and palladium dibenzylideneacetone (Pd$_2$dba$_3$)-chloroform complex (0.086 g, 0.083 mmol). Degassed dioxane (10 ml) was added, followed by 3-bromo-5-(trifluoromethyl)pyridine (0.223 g, 0.991 mmol) and cesium carbonate (0.527 g, 1.62 mmol) The vial was then irradiated in a microwave oven at 150° C. for 90 min. The mixture was diluted with THF and the solids filtered, washing with THF. The filtrate was evaporated and the residue purified by flash chromatography on silica gel with dichloromethane/methanol 100:0→90:10 gradient to yield the title compound (0.147 g, 46%) as an off-white solid, MS (ISP): m/e=394.0 (M+H$^+$).

Example 224

5-(4-Fluoro-pyridin-2-ylamino)-2-methyl-thiazole-4-carboxylic acid (2-methyl-pyridin-4-yl)-amide The title compound, MS (ISP): m/e=344.1 (M+H$^+$), was prepared as for example 223, steps A to E. Step C was performed using 2-methyl-pyridin-4-ylamine and step E was performed using 2-chloro-4-fluoropyridine.

Example 225

5-(2-Chloro-pyridin-4-ylamino)-2-methyl-thiazole-4-carboxylic acid (2-chloro-pyridin-4-yl)-amide The title compound, MS (ISP): m/e=380.1 (M+H$^+$), was prepared as for example 159, steps A to C. Step B was performed using 4-amino-2-chloropyridine and step C was performed using 4-amino-2-chloropyridine.

Example 226

5-((Cyclopropylmethyl)-amino)-2-methyl-thiazole-4-carboxylic acid (2-methyl-pyridin-4-yl)-amide The title compound was prepared as illustrated in scheme 9.

A) A suspension of 2-acetylamino-cyanoacetic acid ethyl ester (1.70 g, 10.00 mmol) and 2,4-bis(4-methoxyphenyl)-1,3,2,4-dithiadiphosphetane 2,4-disulfide (Lawesson's reagent) (2.02 g, 5.00 mmol) in toluene (25.00 ml) was heated under argon to 110° C. and stirred for 22 h. The solvent was then evaporated, and the residue purified by flash chromatography (heptane/ethyl acetate 1:1) to yield 5-amino-2-methyl-thiazole-4-carboxylic acid ethyl ester (0.94 g, 50.5%) as a yellow solid, MS (ISP): m/e=187.3 (M+H$^+$).

B) 5-Amino-2-methyl-thiazole-4-carboxylic acid ethyl ester (0.40 g, 2.15 mmol) was dissolved in 20 ml dry THF. Di-tert.-butyl dicarbonate (0.526 g, 4.41 mmol) and 4-(N,N-dimethylamino)pyridine (0.036 g, 0.3 mmol) were added and the reaction mixture was stirred at 70° C. overnight. The solvent was evaporated, the residue taken up in 20 mL saturated sodium bicarbonate solution and extracted three times with ethyl acetate (30 mL each). The organic phases were pooled, dried with sodium sulfate and evaporated. The crude product was flash-chromatographed on silica gel with heptane/ethyl acetate 100:0→0:100 gradient to yield 5-tert-butoxycarbonylamino-2-methyl-thiazole-4-carboxylic acid ethyl ester as a light yellow solid (0.553 g, 90%), MS (ISP): m/e=287.1 (M+H$^+$).

C) A solution of 2-methyl-pyridin-4-ylamine (0.623 g, 5.77 mmol) in 20 ml dry dioxane was treated at 0° C. with trimethylaluminium (2M in hexane, 2.88 ml, 5.77 mmol). The mixture was stirred at room temperature for 1 h. 5-tert-Butoxycarbonylamino-2-methyl-thiazole-4-carboxylic acid ethyl ester (0.55 g, 1.92 mmol) was added and the reaction mixture was refluxed for 4 h. 1 ml water and 2 g sodium sulfate were sequentially added and filtered. The filtrate was evaporated and the residue purified by flash chromatography on silica gel with heptane/ethyl acetate 100:0→0:100 to yield [2-methyl-4-(2-methyl-pyridin-4-ylcarbamoyl)-thiazol-5-yl]-carbamic acid tert-butyl ester (0.555 g, 83%) as a light yellow solid, MS (ISP): m/e=349.5 (M+H$^+$).

D) [2-Methyl-4-(2-methyl-pyridin-4-ylcarbamoyl)-thiazol-5-yl]-carbamic acid tert-butyl ester (0.532 g, 1.53 mmol) was dissolved in 12 mL trifluoroacetic acid and stirred at room temperature for 30 min. The reaction mixture was treated with 2N sodium carbonate solution until pH 10 and extracted three times with ethyl acetate (50 mL each). The organic phases were pooled, dried with sodium sulfate and evaporated. The crude product was flash-chromatographed on silica gel with heptane/ethyl acetate 100:0→0:100 gradient to yield 5-amino-2-methyl-thiazole-4-carboxylic acid (2-methyl-pyridin-4-yl)-amide as a light yellow solid (0.361 g, 95%), MS (ISP): m/e=249.1 (M+H$^+$).

E) 5-Amino-2-methyl-thiazole-4-carboxylic acid (2-methyl-pyridin-4-yl)-amide (0.200 g, 0.806 mmol) was treated with cyclopropanecarboxaldehyde (0.230 g, 3.22 mmol) and tetraisopropyl-orthotitanate (0.916 g, 3.22 mmol) and stirred at room temperature overnight. Ethanol (5 mL) and sodium cyanoborohydride (0.213 g, 3.22 mmol) were added and the reaction mixture was stirred for 5 h. Water (0.5 mL) was added to the reaction mixture and the solvent was evaporated. The residue was purified by flash chromatography on silica gel with ethyl acetate/methanol 100:0→90:10 gradient to yield the title compound (0.110 g, 45%) as a light yellow solid, MS (ISP): m/e=303.1 (M+H$^+$).

Example 227

5-(5-Hydroxymethyl-pyridin-3-ylamino)-2-methyl-thiazole-4-carboxylic acid (2-methyl-pyridin-4-yl)-amide The tide compound, MS (ISP): m/e=356.3 (M+H$^+$), was prepared as for example 223, steps A to E. Step C was performed using 2-methyl-pyridin-4-ylamine and step E was performed using 5-bromo-3-pyridinemethanol.

Example 228

5-(2-Cyano-pyridin-4-ylamino)-2-methyl-thiazole-4-carboxylic acid (2-methyl-pyridin-4-yl)-amide The title compound, MS (ISP): m/e=351.4 (M+H$^+$), was prepared as for example 223, steps A to E. Step C was performed using 2-methyl-pyridin-4-ylamine and step E was performed using 4-bromo-pyridine-2-carbonitrile.

Example 229

2-Methyl-5-(2-methyl-2H-pyrazol-3-ylamino)-thiazole-4-carboxylic acid (2-chloro-pyridin-4-yl)-amide The title compound, MS (ISP): m/e=349.4 (M+H$^+$), was prepared as for example 159, steps A to C. Step B was performed using 4-amino-2-chloropyridine and step C was performed using 5-amino-1-methyl-pyrazole.

Example 230

5-(3-Chloro-5-fluoro-phenylamino)-2-methyl-thiazole-4-carboxylic acid (2-methyl-pyridin-4-yl)-amide The title compound, MS (ISP): m/e=377.3 (M+H$^+$), was prepared as for example 223, steps A to E. Step C was performed using 2-methyl-pyridin-4-ylamine and step E was performed using 1-bromo-3-chloro-5-fluoro-benzene.

Example 231

5-[2-Methyl-4-(2-methyl-pyridin-4-ylcarbamoyl)-thiazol-5-ylamino]-nicotinamide

The title compound, MS (ISP): m/e=369.3 (M+H$^+$), was prepared as for example 223, steps A to E. Step C was performed using 2-methyl-pyridin-4-ylamine and step E was performed using 5-bromo-nicotinamide.

Example 232

2-Methyl-5-(5-sulfamoyl-pyridin-3-ylamino)-thiazole-4-carboxylic acid (2-methyl-pyridin-4-yl)-amide The title compound, MS (ISP): m/e=405.3 (M+H$^+$), was prepared as for example 223, steps A to E. Step C was performed using 2-methyl-pyridin-4-ylamine and step E was performed using 5-bromo-pyridine-3-sulfonic acid amide.

Example 233

5-(3-Hydroxymethyl-phenylamino)-2-methyl-thiazole-4-carboxylic acid (2-chloro-pyridin-4-yl)-amide The title compound, MS (ISP): m/e=375.3 (M+H$^+$), was prepared as for example 223, steps A to E. Step C was performed using 2-methyl-pyridin-4-ylamine and step E was performed using 3-aminobenzyl alcohol.

Example 234

5-(3-Cyano-5-fluoro-phenylamino)-2-methyl-thiazole-4-carboxylic acid (2-methyl-pyridin-4-yl)-amide The title compound, MS (ISP): m/e=368.3 (M+H$^+$), was prepared as for example 223, steps A to E. Step C was performed using 2-methyl-pyridin-4-ylamine and step E was performed using 3-chloro-5-fluoro-benzonitrile.

Example 235

5-(3,5-Difluoro-phenylamino)-2-methyl-thiazole-4-carboxylic acid (2-hydroxymethyl-pyridin-4-yl)-amide The title compound was prepared as illustrated in scheme 10.

A) To a solution of 5-bromo-2-methyl-thiazole-4-carboxylic acid (2-methyl-pyridin-4-yl)-amide (prepared as described in example 164, steps A and B with 2-methyl-pyridin-4-ylamine) (0.30 g, 0.96 mmol) in 15 mL methylene chloride was added m-chloroperbenzoic acid (70%, 0.474 g, 1.92 mmol) and the reaction mixture was stirred at room temperature overnight. Saturated sodium bicarbonate solution (50 mL) was added and the mixture was extracted three times with methylene chloride, and the combined organic layers were dried over sodium sulphate and evaporated. The crude 5-bromo-2-methyl-thiazole-4-carboxylic acid (2-methyl-1-oxy-pyridin-4-yl)-amide (0.315 g, 100%), MS (ISP): m/e=328.1 (M+), was used without any further purification for the next step.

B) To a solution of 5-bromo-2-methyl-thiazole-4-carboxylic acid (2-methyl-1-oxy-pyridin-4-yl)-amide (2-methyl-pyridin-4-yl)-amide (0.315 g, 0.96 mmol) in 15 mL methylene chloride was added trifluoroacetic acid (0.605 g, 2.88 mmol) and the reaction mixture was stirred at room temperature overnight. The solvents were evaporated and the residue was purified by flash chromatography on silica gel with methylene chloride/methanol 100:0→90:10 gradient to yield 5-bromo-2-methyl-thiazole-4-carboxylic acid (2-hydroxymethyl-pyridin-4-yl)-amide (0.137 g, 43%) as a light yellow solid, MS (ISP): m/e=330.1 (M+H$^+$).

C) A microwave vial was charged with 5-bromo-2-methyl-thiazole-4-carboxylic acid (2-hydroxymethyl-pyridin-4-yl)-amide (0.135 g, 0.411 mmol), 4,5-bis(diphenylphosphino)-9,9-dimethylxanthene (Xantphos) (0.81 g, 0.140 mmol) and palladium dibenzylideneacetone (Pd$_2$dba$_3$)-chloroform complex (0.044 g, 0.043 mmol). Degassed dioxane (10 ml) was added, followed by 3,5-difluoroaniline (0.064 g, 0.496 mmol) and cesium carbonate (0.271 g, 0.831 mmol) The vial was then irradiated in a microwave oven at 150° C. for 40 min. The mixture was diluted with THF and the solids filtered, washing with THF. The filtrate was evaporated and the residue purified by flash chromatography on silica gel with dichloromethane/methanol 100:0→90:10 gradient to yield the title compound (0.013 g, 8%) as an off-white solid, MS (ISP): m/e=377.4 (M+H$^+$).

Example 236

5-((Cyclopropylmethyl)-amino)-2-methyl-thiazole-4-carboxylic acid (2-chloro-pyridin-4-yl)-amide The title compound was prepared as illustrated in scheme 10.

A) A suspension of 2-acetylamino-cyanoacetic acid ethyl ester (1.70 g, 10.00 mmol) and 2,4-bis(4-methoxyphenyl)-1,3,2,4-dithiadiphosphetane 2,4-disulfide (Lawesson's reagent) (2.02 g, 5.00 mmol) in toluene (25.00 ml) was heated under argon to 110° C. and stirred for 22 h. The solvent was then evaporated, and the residue purified by flash chromatography (heptane/ethyl acetate 1:1) to yield 5-amino-2-methyl-thiazole-4-carboxylic acid ethyl ester (0.94 g, 50.5%) as a yellow solid, MS (ISP): m/e=187.3 (M+H$^+$).

B) A-amino-2-methyl-thiazole-4-carboxylic acid ethyl ester (0.15 g, 0.806 mmol), cyclopropanecarboxaldehyde (0.23 g, 3.29 mmol) was treated with cyclopropanecarboxaldehyde (0.230 g, 3.22 mmol) and tetraisopropyl-orthotitanate (0.916 g, 3.22 mmol) and stirred at room temperature overnight. Ethanol (5 mL) and sodium cyanoborohydride (0.213 g, 3.22 mmol) were added and the reaction mixture was stirred for 5 h. Water (0.5 mL) was added to the reaction mixture and the solvent was evaporated. The residue was purified by flash chromatography on silica gel with ethyl acetate/methanol 100:0→90:10 gradient to yield 5-((cyclopropylmethyl)-amino)-2-methyl-thiazole-4-carboxylic acid isopropyl ester (0.170 g, 83%) as a yellow oil, MS (ISP): m/e=255.3 (M+H$^+$).

C) A solution of 2-amino-2-chloropyridine (0.266 g, 2.07 mmol) in 7 ml dry dioxane was treated at 0° C. with trimethylaluminium (2M in hexane, 1.00 ml, 2.00 mmol). The mixture was stirred at room temperature for 1 h. 5-((Cyclopropylmethyl)-amino)-2-methyl-thiazole-4-carboxylic acid isopropyl ester (0.170 g, 0.669 mmol) was added and the reaction mixture was refluxed for 5 h. 1 ml water and 2 g sodium sulfate were sequentially added and filtered. The filtrate was evaporated and the residue purified by flash chromatography on silica gel with heptane/ethyl acetate 100:0→0:100 to yield the title compound (0.030 g, 14%) as a yellow solid, MS (ISP): m/e=323.5 (M+H$^+$).

Example 237

5-(5-Fluoro-pyridin-3-ylamino)-2-methyl-thiazole-4-carboxylic acid (2-chloro-pyridin-4-yl)-amide The title compound, MS (ISP): m/e=364.3 (M+H$^+$), was prepared as for example 214, steps A to E. Step C was performed using 2-amino-2-chloropyridine and step E was performed using 3,5-difluoropyridine.

Example 238

5-(3-Imidazol-1-yl-phenylamino)-2-methyl-thiazole-4-carboxylic acid (2-methyl-pyridin-4-yl)-amide The title compound, MS (ISP): m/e=391.3 (M+H$^+$), was prepared as for example 223, steps A to E. Step C was performed using 2-methyl-pyridin-4-ylamine and step E was performed using 1-(3-chlorophenyl)imidazole.

Example 239

2-Methyl-5-[3-(1-methyl-1H-pyrazol-3-yl)-phenylamino]-thiazole-4-carboxylic acid (2-methyl-pyridin-4-yl)-amide The title compound, MS (ISP): m/e=405.3 (M+H$^+$), was prepared as for example 223, steps A to E. Step C was performed using 2-methyl-pyridin-4-ylamine and step E was performed using 3-(3-bromo-phenyl)-1-methyl-1H-pyrazole.

Example 240

5-(3,5-Difluoro-phenylamino)-2-methyl-thiazole-4-carboxylic acid (4-methyl-thiazol-2-yl)-amide The title compound, MS (ISP): m/e=367.0 (M+H$^+$), was prepared as for example 163, steps A to C. Step B was performed using 1-bromo-3,5-difluorobenzene and step C was performed using 2-amino-4-methylthiazole.

Example 241

5-(5-Fluoro-pyridin-3-ylamino)-2-methyl-thiazole-4-carboxylic acid (4-methyl-thiazol-2-yl)-amide The title compound, MS (ISP): m/e=350.4 (M+H$^+$), was prepared as for example 163, steps A to C. Step B was performed using 3,5-difluoropyridine and step C was performed using 2-amino-4-methylthiazole.

Alternatively, the title compound can be prepared as in example 163 using steps A to C using 3-Bromo-5-fluoropyridine (the preparation of which is described in example P hereinafter) with the difference that step B is performed with conventional heating means instead of microwaves.

Example 242

5-(5-Fluoro-pyridin-3-ylamino)-2-methyl-thiazole-4-carboxylic acid (2-methyl-pyrimidin-4-yl)-amide The title compound, MS (ISP): m/e=345.0 (M+H$^+$), was prepared as for example 223, steps A to E. Step C was performed using 2-methyl-4-amino-pyrimidine and step E was performed using 3,5-difluoropyridine.

Example 243

5-(4-Fluoro-pyridin-2-ylamino)-2-methyl-thiazole-4-carboxylic acid (2-methyl-pyrimidin-4-yl)-amide The title compound, MS (ISP): m/e=345.0 (M+H$^+$), was prepared as for example 223, steps A to E. Step C was performed using 2-methyl-4-amino-pyrimidine and step E was performed using 2-chloro-4-fluoropyridine.

Example 244

5-(5-Fluoro-pyridin-3-ylamino)-2-methyl-thiazole-4-carboxylic acid (5-fluoro-pyridin-2-yl)-amide The title compound, MS (ISP): m/e=348.0 (M+H$^+$), was prepared as for example 163, steps A to C. Step B was performed using 3,5-difluoropyridine and step C was performed using 2-amino-5-fluoropyridine.

Example 245

5-(5-Fluoro-pyridin-3-ylamino)-2-methyl-thiazole-4-carboxylic acid (1-methyl-1H-pyrazol-3-yl)-amide The title compound, MS (ISP): m/e=333.3 (M+H$^+$), was prepared as for example 163, steps A to C. Step B was performed using 3,5-difluoropyridine and step C was performed using 3-amino-1-methylpyrazole.

Example 246

2-Methyl-5-[(pyridin-3-ylmethyl)-amino]-thiazole-4-carboxylic acid (2-methyl-pyridin-4-yl)-amide The title compound, MS (ISP): m/e=340.0 (M+H$^+$), was prepared as for example 226, steps A to E. Step C was performed using 2-methyl-4-amino-pyridine and step E was performed using 3-pyridinecarboxaldehyde.

Example 247

2-Methyl-5-(2-methyl-2H-pyrazol-3-ylamino)-thiazole-4-carboxylic acid (2-methyl-pyrimidin-4-yl)-amide The title compound, MS (ISP): m/e=330.1 (M+H⁺), was prepared as for example 223, steps A to E. Step C was performed using 2-methyl-4-amino-pyrimidine and step E was performed using 5-amino-1-methylpyrazole.

Example 248

5-(2-Ethyl-2H-pyrazol-3-ylamino)-2-methyl-thiazole-4-carboxylic acid (2-methyl-pyrimidin-4-yl)-amide The tide compound, MS (ISP): m/e=344.1 (M+H⁺), was prepared as for example 223, steps A to E. Step C was performed using 2-methyl-4-amino-pyrimidine and step E was performed using 5-amino-1-ethylpyrazole.

Example 249

5-(2,5-Dimethyl-2H-pyrazol-3-ylamino)-2-methyl-thiazole-4-carboxylic acid (2-methyl-pyrimidin-4-yl)-amide The title compound, MS (ISP): m/e=344.1 (M+H⁺), was prepared as for example 223, steps A to E. Step C was performed using 2-methyl-4-amino-pyrimidine and step E was performed using 5-amino-1,3-dimethylpyrazole.

Example 250

2-Methyl-5-(1-methyl-1H-pyrazol-4-ylamino)-thiazole-4-carboxylic acid (2-methyl-pyrimidin-4-yl)-amide The title compound, MS (ISP): m/e=330.3 (M+H⁺), was prepared as for example 223, steps A to E. Step C was performed using 2-methyl-4-amino-pyrimidine and step E was performed using 1-methyl-1H-pyrazol-4-ylamine.

Example 251

2-Methyl-5-(3-methyl-isoxazol-5-ylamino)-thiazole-4-carboxylic acid (2-methyl-pyrimidin-4-yl)-amide The title compound, MS (ISP): m/e=331.1 (M+H⁺), was prepared as for example 223, steps A to E. Step C was performed using 2-methyl-4-amino-pyrimidine and step E was performed using 3-amino-5-methylisoxazole.

Example 252

2-Methyl-5-[(tetrahydro-pyran-4-ylmethyl)-amino]-thiazole-4-carboxylic acid (2-methyl-pyridin-4-yl)-amide The title compound, MS (ISP): m/e=347.3 (M+H⁺), was prepared as for example 226, steps A to E. Step C was performed using 2-methyl-4-amino-pyridine and step E was performed using tetrahydropyranyl-4-carboxaldehyde.

Example 253

2-Methyl-5-(1-methyl-1H-pyrazol-3-ylamino)-thiazole-4-carboxylic acid (2-methyl-pyrimidin-4-yl)-amide The title compound, MS (ISP): m/e=330.0 (M+H⁺), was prepared as for example 223, steps A to E. Step C was performed using 2-methyl-4-amino-pyrimidine and step E was performed using 1-methyl-1H-pyrazol-3-ylamine.

Example 254

5-(3,5-Difluoro-benzylamino)-2-methyl-thiazole-4-carboxylic acid (2-methyl-pyridin-4-yl)-amide The title compound, MS (ISP): m/e=375.4 (M+H⁺), was prepared as for example 226, steps A to E. Step C was performed using 2-methyl-4-amino-pyridine and step E was performed using 3,5-difluorobenzaldehyde.

Example 255

2-Methyl-5-[(pyridin-2-ylmethyl)-amino]-thiazole-4-carboxylic acid (2-methyl-pyridin-4-yl)-amide The title compound, MS (ISP): m/e=340.3 (M+H⁺), was prepared as for example 226, steps A to E. Step C was performed using 2-methyl-4-amino-pyridine and step E was performed using 2-pyridinecarboxaldehyde.

Example 256

2-Methyl-5-(1-methyl-1H-pyrazol-4-ylamino)-thiazole-4-carboxylic acid (2-methyl-pyridin-4-yl)-amide The title compound, MS (ISP): m/e=329.0 (M+H⁺), was prepared as for example 223, steps A to E. Step C was performed using 2-methyl-4-amino-pyrimidine and step E was performed using 1-methyl-1H-pyrazol-4-ylamine.

Example 257

5-(3,5-Difluoro-phenylamino)-2-methyl-thiazole-4-carboxylic acid (1-methyl-1H-[1,2,4]triazol-3-yl)-amide The title compound, MS (ISP): m/e=351.4 (M+H⁺), was prepared as for example 163, steps A to C. Step B was performed using 1-bromo-3,5-difluorobenzene and step C was performed using 1-methyl-1H-[1,2,4]triazol-3-ylamine.

Example 258

5-(5-Difluoromethyl-pyridin-3-ylamino)-2-methyl-thiazole-4-carboxylic acid (2-methyl-pyridin-4-yl)-amide The title compound, MS (ISP): m/e=376.4 (M+H⁺), was prepared as for example 223, steps A to E. Step C was performed using 2-methyl-4-amino-pyridine and step E was performed using 5-difluoromethyl-pyridin-3-ylamine.

Example 259

5-(3,5-Difluoro-phenylamino)-2-methyl-thiazole-4-carboxylic acid (3-methyl-[1,2,4]thiadiazol-5-yl)-amide The title compound, MS (ISP): m/e=368.0 (M+H$^+$), was prepared as for example 163, steps A to C. Step B was performed using 1-bromo-3,5-difluorobenzene and step C was performed using 5-amino-3-methyl-1,2,4-thiadiazole.

Example 260

5-(3,5-Difluoro-phenylamino)-2-methyl-thiazole-4-carboxylic acid (1-methyl-1H-pyrazol-3-yl)-amide The title compound, MS (ISP): m/e=350.4 (M+H$^+$), was prepared as for example 163, steps A to C. Step B was performed using 1-bromo-3,5-difluorobenzene and step C was performed using 1-methyl-1H-pyrazol-3-ylamine.

Example 261

5-(5-Fluoro-pyridin-3-ylamino)-2-methyl-thiazole-4-carboxylic acid (4-trifluoromethyl-thiazol-2-yl)-amide The title compound, MS (ISP): m/e=404.3 (M+H$^+$), was prepared as for example 163, steps A to C. Step B was performed using 3,5-difluoropyridine and step C was performed using 4-(trifluoromethyl)-1,3-thiazole-2-amine.

Example 262

2-Methyl-5-(thiazol-2-ylamino)-thiazole-4-carboxylic acid (2-methyl-pyridin-4-yl)-amide The title compound, MS (ISP): m/e=332.1 (M+H$^+$), was prepared as for example 223, steps A to E. Step C was performed using 2-methyl-4-amino-pyridine and step E was performed using 2-aminothiazole.

Example 263

2-Methyl-5-[(3-methyl-3H-imidazol-4-ylmethyl)-amino]-thiazole-4-carboxylic acid (2-methyl-pyridin-4-yl)-amide The title compound, MS (ISP): m/e=343.3 (M+H$^+$), was prepared as for example 226, steps A to E. Step C was performed using 2-methyl-4-amino-pyridine and step E was performed using 1-methyl-1H-imidazole-5-carbaldehyde.

Example 264

2-Methyl-5-(3-[1,2,3]triazol-1-yl-phenylamino)-thiazole-4-carboxylic acid (2-methyl-pyridin-4-yl)-amide The title compound, MS (ISP): m/e=392.3 (M+H$^+$), was prepared as for example 223, steps A to E. Step C was performed using 2-methyl-4-amino-pyridine and step E was performed using 3-[1,2,3]triazol-1-yl-phenylamine.

Example 265

2-Methyl-5-[3-(2-methyl-imidazol-1-yl)-phenylamino]-thiazole-4-carboxylic acid (2-methyl-pyridin-4-yl)-amide The title compound, MS (ISP): m/e=405.3 (M+H$^+$), was prepared as for example 223, steps A to E. Step C was performed using 2-methyl-4-amino-pyridine and step E was performed using 3-(2-methyl-imidazol-1-yl)-phenylamine.

Example 266

{3-[2-Methyl-4-(2-methyl-pyridin-4-ylcarbamoyl)-thiazol-5-ylamino]-benzyl}-carbamic acid tert-butyl ester The tide compound, MS (ISP): m/e=454.3 (M+H$^+$), was prepared as for example 223, steps A to E. Step C was performed using 2-methyl-4-amino-pyridine and step E was performed using (3-amino-benzyl)-carbamic acid tert-butyl ester.

Example 267

5-(5-Chloro-pyridin-3-ylamino)-2-methyl-thiazole-4-carboxylic acid (1-methyl-1H-pyrazol-3-yl)-amide The title compound, MS (ISP): m/e=454.3 (M+H$^+$), was prepared as for example 223, steps A to E. Step C was performed using 1-methyl-1H-pyrazol-3-ylamine and step E was performed using 5-chloropyridin-3-amine.

Example 268

2-Methyl-5-(pyrimidin-5-ylamino)-thiazole-4-carboxylic acid (1-methyl-1H-pyrazol-3-yl)-amide The title compound, MS (ISP): m/e=316.1 (M+H$^+$), was prepared as for example 223, steps A to E. Step C was performed using 1-methyl-1H-pyrazol-3-ylamine and step E was performed using 5-aminopyrimidine.

Example 269

5-(4-Cyano-2-methyl-2H-pyrazol-3-ylamino)-2-methyl-thiazole-4-carboxylic acid (2-methyl-pyridin-4-yl)-amide The title compound, MS (ISP): m/e=354.1 (M+H$^+$), was prepared as for example 223, steps A to E. Step C was performed using 2-methyl-4-amino-pyridine and step E was performed using 5-amino-1-methyl-1H-pyrazole-4-carbonitrile.

Example 270

5-(3,5-Difluoro-phenylamino)-2-methyl-thiazole-4-carboxylic acid (1-cyclopropylmethyl-1H-pyrazol-3-yl)-amide The title compound, MS (ISP): m/e=390.3 (M+H$^+$), was prepared as for example 163, steps A to C. Step B was performed using 1-bromo-3,5-difluorobenzene and step C was performed using 1-cyclopropylmethyl-1H-pyrazol-3-ylamine.

Example 271

5-(5-Cyclopropyl-2-methyl-2H-pyrazol-3-ylamino)-2-methyl-thiazole-4-carboxylic acid (2-methyl-pyridin-4-yl)-amide The title compound, MS (ISP): m/e=369.1 (M+H$^+$), was prepared as for example 223, steps A to E. Step C was performed using 2-methyl-4-amino-pyridine and step E was performed using 5-amino-3-cyclopropyl-1-methylpyrazole.

Example 272

2-Methyl-5-(2-methyl-2H-pyrazol-3-ylamino)-thiazole-4-carboxylic acid (1-methyl-1H-pyrazol-3-yl)-amide The title compound, MS (ISP): m/e=318.0 (M+H$^+$), was prepared as for example 223, steps A to E. Step C was performed using 1-methyl-1H-pyrazol-3-ylamine and step E was performed using 5-amino-1-methylpyrazole.

Example 273

5-(2-Chloro-pyridin-4-ylamino)-2-methyl-thiazole-4-carboxylic acid (1-methyl-1H-pyrazol-3-yl)-amide The title compound, MS (ISP): m/e=349.3 (M+H$^+$), was prepared as for example 223, steps A to E. Step C was performed using 1-methyl-1H-pyrazol-3-ylamine and step E was performed using 4-amino-2-chloropyridine.

Example 274

5-(3-Methoxymethyl-phenylamino)-2-methyl-thiazole-4-carboxylic acid (2-methyl-pyridin-4-yl)-amide The title compound, MS (ISP): m/e=369.1 (M+H$^+$), was prepared as for example 223, steps A to E. Step C was performed using 2-methyl-4-amino-pyridine and step E was performed using 3-methoxymethyl-phenylamine.

Example 275

2-Methyl-5-[2-(2,2,2-trifluoro-ethyl)-2H-pyrazol-3-ylamino]-thiazole-4-carboxylic acid (2-methyl-pyridin-4-yl)-amide The title compound, MS (ISP): m/e=397.1 (M+H$^+$), was prepared as for example 223, steps A to E. Step C was performed using 2-methyl-4-amino-pyridine and step E was performed using 2-(2,2,2-trifluoro-ethyl)-2H-pyrazol-3-ylamine.

Example 276

5-(5-Cyclopropyl-2-methyl-2H-pyrazol-3-ylamino)-2-methyl-thiazole-4-carboxylic acid (1-methyl-1H-pyrazol-3-yl)-amide The title compound, MS (ISP): m/e=358.3 (M+H$^+$), was prepared as for example 115, steps A to E. Step D was performed using 5-amino-3-cyclopropyl-1-methylpyrazole and step E was performed using 1-methyl-1H-pyrazol-3-ylamine.

Example 277

5-(3,5-Difluoro-phenylamino)-2-methyl-thiazole-4-carboxylic acid [3-(acetylamino-methyl)-phenyl]-amide The title compound, MS (ISP): m/e=417.4 (M+H$^+$), was prepared as for example 163, steps A to C. Step B was performed using 1-bromo-3,5-difluorobenzene and step C was performed using N-(3-amino-benzyl)-acetamide.

Example 278

5-(3-Cyano-5-fluoro-phenylamino)-2-methyl-thiazole-4-carboxylic acid (1-methyl-1H-pyrazol-3-yl)-amide The title compound, MS (ISP): m/e=357.1 (M+H$^+$), was prepared as for example 223, steps A to E. Step C was performed using 1-methyl-1H-pyrazol-3-ylamine and step E was performed using 5-amino-3-fluorobenzonitrile.

Example 279

5-(3,5-Difluoro-phenylamino)-2-methyl-thiazole-4-carboxylic acid (4-cyclopropyl-thiazol-2-yl)-amide The title compound) MS (ISP): m/e=393.0 (M+H$^+$), was prepared as for example 163, steps A to C. Step B was performed using 1-bromo-3,5-difluorobenzene and step C was performed using 4-cyclopropyl-thiazol-2-ylamine.

Example 280

5-(3,5-Difluoro-phenylamino)-2-methyl-thiazole-4-carboxylic acid (3-methoxymethyl-phenyl)-amide The title compound, MS (ISP): m/e=390.1 (M+H$^+$), was prepared as for example 163, steps A to C. Step B was performed using 1-bromo-3,5-difluorobenzene and step C was performed using 3-methoxymethyl-phenylamine.

Example 281

5-(3,5-Difluoro-phenylamino)-2-methyl-thiazole-4-carboxylic acid [1-(2-methoxy-ethyl)-1H-pyrazol-3-yl]-amide The title compound, MS (ISP): m/e=394.0 (M+H$^+$), was prepared as for example 163, steps A to C. Step B was performed using 1-bromo-3,5-difluorobenzene and step C was performed using 1-(2-methoxy-ethyl)-1H-pyrazol-3-ylamine.

Example 282

5-[3-(Acetylamino-methyl)-phenylamino]-2-methyl-thiazole-4-carboxylic acid (2-methyl-pyridin-4-yl)-amide The title compound, MS (ISP): m/e=396.3 (M+H$^+$), was prepared as for example 223, steps A to E. Step C was performed using 2-methyl-4-amino-pyridine and step E was performed using N-(3-amino-benzyl)-acetamide.

Example 283

5-(5-Cyclopropyl-2-methyl-2H-pyrazol-3-ylamino)-2-methyl-thiazole-4-carboxylic acid (4-trifluoromethyl-thiazol-2-yl)-amide The title compound, MS (ISP): m/e=429.3 (M+H$^+$), was prepared as for example 115, steps A to E. Step D was performed using 5-amino-3-cyclopropyl-1-methylpyrazole and step E was performed using 4-trifluoromethyl-thiazole-2-ylamine.

Example 284

5-(3,5-Difluoro-phenylamino)-2-methyl-thiazole-4-carboxylic acid (5-fluoro-6-methyl-pyridin-2-yl)-amide The title compound, MS (ISP): m/e=379.0 (M+H$^+$), was prepared as for example 163, steps A to C. Step B was performed using 1-bromo-3,5-difluorobenzene and step C was performed using 2-amino-5-fluoro-6-methylpyridine (Sanchez & al., J. Heterocycl. Chem. 24, 215(1987).

Example 285

2-Methyl-5-(2-methyl-5-trifluoromethyl-2H-pyrazol-3-ylamino)-thiazole-4-carboxylic acid (2-methyl-pyridin-4-yl)-amide The title compound, MS (ISP): m/e=397.3 (M+H$^+$), was prepared as for example 223, steps A to E. Step C was performed using 2-methyl-4-amino-pyridine and step E was performed using 2-methyl-5-trifluoromethyl-2H-pyrazol-3-ylamine.

Example 286

5-(5-Fluoro-pyridin-3-ylamino)-2-methyl-thiazole-4-carboxylic acid (4-cyclopropyl-thiazol-2-yl)-amide The tide compound, MS (ISP): m/e=376.0 (M+H$^+$), was prepared as for example 163, steps A to C. Step B was performed using 3,5-difluoropyridine and step C was performed using 4-cyclopropyl-thiazol-2-ylamine.

Example 287

5-(5-Fluoro-pyridin-3-ylamino)-2-methyl-thiazole-4-carboxylic acid (3-methoxymethyl-phenyl)-amide The tide compound, MS (ISP): m/e=373.1 (M+H$^+$), was prepared as for example 163, steps A to C. Step B was performed using 3,5-difluoropyridine and step C was performed using 3-methoxymethyl-phenylamine.

Example 288

5-(3,5-Difluoro-phenylamino)-2-methyl-thiazole-4-carboxylic acid (4-methoxymethyl-thiazol-2-yl)-amide The tide compound, MS (ISP): m/e=397.3 (M+H$^+$), was prepared as for example 163, steps A to C. Step B was performed using 1-bromo-3,5-difluorobenzene and step C was performed using 4-methoxymethyl-thiazole-2-ylamine [CAS 640768-40-7].

Example 289

5-(5-Fluoro-pyridin-3-ylamino)-2-methyl-thiazole-4-carboxylic acid [1-(2-methoxy-ethyl)-1H-pyrazol-3-yl]-amide The tide compound, MS (ISP): m/e=377.4 (M+H$^+$), was prepared as for example 163, steps A to C. Step B was performed using 3,5-difluoropyridine and step C was performed using 1-(2-methoxy-ethyl)-1H-pyrazol-3-ylamine.

Example 290

2-Methyl-5-(pyridin-3-ylamino)-thiazole-4-carboxylic acid (4-trifluoromethyl-thiazol-2-yl)-amide The title compound, MS (ISP): m/e=386.0 (M+H$^+$), was prepared as for example 115, steps A to E. Step D was performed using 3-amino-pyridine and step E was performed using 4-trifluoromethyl-thiazole-2-ylamine.

Example 291

2-Methyl-5-(pyridin-3-ylamino)-thiazole-4-carboxylic acid (1-methyl-1H-pyrazol-3-yl)-amide The title compound, MS (ISP): m/e=315.1 (M+H$^+$), was prepared as for example 115, steps A to E. Step D was performed using 3-amino-pyridine and step E was performed using 1-methyl-1H-pyrazol-3-ylamine.

Example 292

2-Methyl-5-(pyridin-3-ylamino)-thiazole-4-carboxylic acid [1-(2-methoxy-ethyl)-1H-pyrazol-3-yl]-amide The title compound, MS (ISP): m/e=359.0 (M+H$^+$), was prepared as for example 115, steps A to E. Step D was performed using 3-amino-pyridine and step E was performed using 1-(2-methoxy-ethyl)-1H-pyrazol-3-ylamine.

Example 293

2-Methyl-5-(pyridin-3-ylamino)-thiazole-4-carboxylic acid (4-cyclopropyl-thiazol-2-yl)-amide The title compound, MS (ISP): m/e=358.1 (M+H$^+$), was prepared as for example 115, steps A to E. Step D was performed using 3-amino-pyridine and step E was performed using 4-cyclopropyl-thiazol-2-ylamine.

Example 294

5-(3-Methoxymethyl-phenylamino)-2-methyl-thiazole-4-carboxylic acid (1-methyl-1H-pyrazol-3-yl)-amide The title compound, MS (ISP): m/e=358.0 (M+H$^+$), was prepared as for example 159, steps A to C. Step B was performed using 1-methyl-1H-pyrazol-3-ylamine and step C was performed using 3-methoxymethyl-phenylamine.

Example 295

5-(Cyclopropylmethyl-amino)-2-methyl-thiazole-4-carboxylic acid (1-methyl-1H-pyrazol-3-yl)-amide The title compound, MS (ISP): m/e=292.0 (M+H$^+$), was prepared as for example 159, steps A to C. Step B was performed using 1-methyl-1H-pyrazol-3-ylamine and step C was performed using aminomethylcyclopropane.

Example 296

5-(3-Hydroxymethyl-phenylamino)-2-methyl-thiazole-4-carboxylic acid (1-methyl-1H-pyrazol-3-yl)-amide The title compound, MS (ISP): m/e=344.1 (M+H$^+$), was prepared as for example 159, steps A to C. Step B was performed using 1-methyl-1H-pyrazol-3-ylamine and step C was performed using 3-aminobenzylalcohol.

Example 297

5-(3,5-Difluoro-phenylamino)-2-methyl-thiazole-4-carboxylic acid [1,3,4]thiadiazol-2-ylamide The title compound, MS (ISP): m/e=354.0 (M+H$^+$), was prepared as for example 163, steps A to C. Step B was performed using 1-bromo-3,5-difluorobenzene and step C was performed using 2-amino-1,3,4-thiadiazole.

Example 298

2-Methyl-5-(pyridin-3-ylamino)-thiazole-4-carboxylic acid (4-methyl-thiazol-2-yl)-amide The title compound, MS (ISP): m/e=332.0 (M+H$^+$), was prepared as for example 115, steps A to E. Step D was performed using 3-amino-pyridine and step E was performed using 2-amino-4-methylthiazole.

Example 299

2-Methyl-5-(pyridin-3-ylamino)-thiazole-4-carboxylic acid thiazol-2-ylamide

The title compound, MS (ISP): m/e=318.1 (M+H$^+$), was prepared as for example 115, steps A to E. Step D was performed using 3-amino-pyridine and step E was performed using 2-aminothiazole.

Example 300

5-(3,5-Difluoro-phenylamino)-2-methyl-thiazole-4-carboxylic acid (5-methyl-1H-[1,2,4]triazol-3-yl)-amide The title compound, MS (ISP): m/e=351.1 (M+H$^+$), was prepared as for example 163, steps A to C. Step B was performed using 1-bromo-3,5-difluorobenzene and step C was performed using 3-amino-5-methyl-4H-1,2,4-triazole.

Example 301

5-(2,5-Difluoro-phenylamino)-2-methyl-thiazole-4-carboxylic acid (1-methyl-1H-pyrazol-3-yl)-amide The title compound, MS (ISP): m/e=350.3 (M+H$^+$), was prepared as for example 159, steps A to C. Step B was performed using 1-methyl-1H-pyrazol-3-ylamine and step C was performed using 2,5-difluoroaniline.

Example 302

5-(5-Cyclopropyl-2-methyl-2H-pyrazol-3-ylamino)-2-methyl-thiazole-4-carboxylic acid (4-methyl-thiazol-2-yl)-amide The title compound, MS (ISP): m/e=375.4 (M+H$^+$), was prepared as for example 159, steps A to C. Step B was performed using 2-amino-4-methylthiazole and step C was performed using 5-amino-3-cyclopropyl-1-methylpyrazole.

Example 303

5-(2-Chloro-pyridin-4-ylamino)-2-methyl-thiazole-4-carboxylic acid (4-methyl-thiazol-2-yl)-amide The title compound, MS (ISP): m/e=366.1 (M+H$^+$), was prepared as for example 159, steps A to C. Step B was performed using 2-amino-4-methylthiazole and step C was performed using 4-amino-2-chloropyridine.

Example 304

2-Methyl-5-(pyridin-3-ylamino)-thiazole-4-carboxylic acid (5-ethyl-thiazol-2-yl)-amide The title compound, MS (ISP): m/e=346.1 (M+H$^+$), was prepared as for example 115, steps A to E. Step D was performed using 3-amino-pyridine and step E was performed using 4-ethyl-thiazol-2-ylamine [CAS 34631-53-3].

Example 305

2-Methyl-5-(pyrimidin-5-ylamino)-thiazole-4-carboxylic acid (4-methyl-thiazol-2-yl)-amide The tide compound, MS (ISP): m/e=333.3 (M+H$^+$), was prepared as for example 159, steps A to C. Step B was performed using 2-amino-4-methylthiazole and step C was performed using 5-aminopyrimidine.

Example 306

2-Methyl-5-(1-methyl-1H-pyrazol-4-ylamino)-thiazole-4-carboxylic acid (4-methyl-thiazol-2-yl)-amide The tide compound, MS (ISP): m/e=335.3 (M+H$^+$), was prepared as for example 159, steps A to C. Step B was performed using 2-amino-4-methylthiazole and step C was performed using 1-methyl-1H-pyrazol-4-ylamine.

Example 307

5-(Cyclopropylmethyl-amino)-2-methyl-thiazole-4-carboxylic acid (4-methyl-thiazol-2-yl)-amide The tide compound, MS (ISP): m/e=309.1 (M+H$^+$), was prepared as for example 159, steps A to C. Step B was performed using 2-amino-4-methylthiazole and step C was performed using aminomethylcyclopropane.

Example 308

2-Methyl-5-(pyridin-2-ylamino)-thiazole-4-carboxylic acid (4-methyl-thiazol-2-yl)-amide The tide compound, MS (ISP): m/e=332.3 (M+H$^+$), was prepared as for example 159, steps A to C. Step B was performed using 2-amino-4-methylthiazole and step C was performed using 2-aminopyridine.

Example 309

5-(3-Cyano-phenylamino)-2-methyl-thiazole-4-carboxylic acid (1-methyl-1H-pyrazol-3-yl)-amide The title compound, MS (ISP): m/e=339.1 (M+H$^+$), was prepared as for example 159, steps A to C. Step B was performed using 1-methyl-1H-pyrazol-3-ylamine and step C was performed using 3-aminobenzonitrile.

Example 310

5-(2,5-Dimethyl-2H-pyrazol-3-ylamino)-2-methyl-thiazole-4-carboxylic acid (4-methyl-thiazol-2-yl)-amide The title compound, MS (ISP): m/e=349.4 (M+H$^+$), was prepared as for example 159, steps A to C. Step B was performed using 2-amino-4-methylthiazole and step C was performed using 5-amino-1,3-dimethylpyrazole.

Example 311

2-Methyl-5-(1-methyl-1H-pyrazol-3-ylamino)-thiazole-4-carboxylic acid (4-methyl-thiazol-2-yl)-amide The tide compound, MS (ISP): m/e=335.4 (M+H$^+$), was prepared as for example 159, steps A to C. Step B was performed using 2-amino-4-methylthiazole and step C was performed using 3-amino-1-methylpyrazole.

Example 312

2-Methyl-5-(tetrahydro-pyran-4-ylamino)-thiazole-4-carboxylic acid (4-methyl-thiazol-2-yl)-amide The title compound, MS (ISP): m/e=339.1 (M+H$^+$), was prepared as for example 159, steps A to C. Step B was performed using 2-amino-4-methylthiazole and step C was performed using 4-aminotetrahydropyran.

Example 313

2-Methyl-5-methylamino-thiazole-4-carboxylic acid (4-methyl-thiazol-2-yl)-amide

The title compound, MS (ISP): m/e=269.5 (M+H$^+$), was prepared as for example 159, steps A to C. Step B was performed using 2-amino-4-methylthiazole and step C was performed using methylamine (solution in water).

Example 314

5-(3,5-Difluoro-phenylamino)-2-methyl-thiazole-4-carboxylic acid (3-cyano-5-fluoro-phenyl)-amide The title compound, MS (ISP): m/e=389.3 (M+H$^+$), was prepared as for example 163, steps A to C. Step B was performed using 1-bromo-3,5-difluorobenzene and step C was performed using 5-amino-3-fluorobenzonitrile.

Example 315

2-Methyl-5-(pyridin-4-ylamino)-thiazole-4-carboxylic acid (4-methyl-thiazol-2-yl)-amide The title compound, MS (ISP): m/e=332.3 (M+H$^+$), was prepared as for example 159, steps A to C. Step B was performed using 2-amino-4-methylthiazole and step C was performed using 4-aminopyridine.

Example 316

5-(5-Difluoromethyl-pyridin-3-ylamino)-2-methyl-thiazole-4-carboxylic acid (4-methyl-thiazol-2-yl)-amide The title compound, MS (ISP): m/e=382.3 (M+H$^+$), was prepared as for example 159, steps A to C. Step B was performed using 2-amino-4-methylthiazole and step C was performed using 5-difluoromethyl-pyridin-3-ylamine.

Example 317

2-Methyl-5-(pyrimidin-2-ylamino)-thiazole-4-carboxylic acid (4-methyl-thiazol-2-yl)-amide The title compound, MS (ISP): m/e=333.3 (M+H$^+$), was prepared as for example 159, steps A to C. Step B was performed using 2-amino-4-methylthiazole and step C was performed using 2-aminopyrimidine.

Example 318

2-Methyl-5-[(pyridin-3-ylmethyl)-amino]-thiazole-4-carboxylic acid (4-methyl-thiazol-2-yl)-amide The title compound, MS (ISP): m/e=346.0 (M+H$^+$), was prepared as for example 159, steps A to C. Step B was performed using 2-amino-4-methylthiazole and step C was performed using 3-picolylamine.

Example 319

2-Methyl-5-(pyridin-3-ylamino)-thiazole-4-carboxylic acid (5-methyl-4H-[1,2,4]triazol-3-yl)-amide The title compound, MS (ISP): m/e=316.1 (M+H$^+$), was prepared as for example 115, steps A to E. Step D was performed using 3-amino-pyridine and step E was performed using 3-amino-5-methyl-4H-1,2,4-triazole.

Example 320

2-Methyl-5-(pyridin-3-ylamino)-thiazole-4-carboxylic acid (4-methoxymethyl-thiazol-2-yl)-amide The title compound, MS (ISP): m/e=362.4 (M+H$^+$), was prepared as for example 115, steps A to E. Step D was performed using 3-amino-pyridine and step E was performed using 4-methoxymethyl-thiazol-2-ylamine.

Example 321

5-Dimethylamino-2-methyl-thiazole-4-carboxylic acid (4-methyl-thiazol-2-yl)-amide The title compound, MS (ISP): m/e=283.3 (M+H$^+$), was prepared as for example 159, steps A to C. Step B was performed using 2-amino-4-methylthiazole and step C was performed using dimethylamine (40% solution in water).

Example 322

5-(3,5-Difluoro-benzylamino)-2-methyl-thiazole-4-carboxylic acid (4-methyl-thiazol-2-yl)-amide The title compound, MS (ISP): m/e=381.0 (M+H$^+$), was prepared as for example 159, steps A to C. Step B was performed using 2-amino-4-methylthiazole and step C was performed using 3,5-difluorobenzylamine

Example 323

5-(5-Cyano-pyridin-3-ylamino)-2-methyl-thiazole-4-carboxylic acid (4-methyl-thiazol-2-yl)-amide The title compound, MS (ISP): m/e=357.1 (M+H$^+$), was prepared as for example 163, steps A to C. Step B was performed using 5-bromopyridine-3-carbonitrile and step C was performed using 2-amino-4-methylthiazole.

Example 324

5-(2-Methoxy-ethylamino)-2-methyl-thiazole-4-carboxylic acid (2-methyl-pyridin-4-yl)-amide The title compound, MS (ISP): m/e=370.3 (M+H$^+$), was prepared as for example 159, steps A to C. Step B was performed using 2-methyl-4-amino-pyridine and step C was performed using 2-methoxyethylamine.

Example 325

5-Cyclopropylamino-2-methyl-thiazole-4-carboxylic acid (2-methyl-pyridin-4-yl)-amide The title compound, MS (ISP): m/e=289.3 (M+H$^+$), was prepared as for example 159, steps A to C. Step B was performed using 2-methyl-4-amino-pyridine and step C was performed using cyclopropylamine.

Example 326

5-(5-Fluoro-pyridin-3-ylamino)-2-methyl-thiazole-4-carboxylic acid (2-methyl-thiazol-4-yl)-amide The title compound, MS (ISP): m/e=351.1 (M+H$^+$), was prepared as for example 214, steps A to E. Step C was performed using 4-amino-2-methylthiazole [CAS 103392-01-4] and step E was performed using 3,5-difluoropyridine.

Example 327

5-(2-Chloro-pyridin-4-ylamino)-2-methyl-thiazole-4-carboxylic acid (2-methyl-thiazol-4-yl)-amide The title compound, MS (ISP): m/e=366.0 (M+H$^+$), was prepared as for example 214, steps A to E. Step C was performed using 4-amino-2-methylthiazole [CAS 103392-01-4] and step E was performed using 2-chloro-4-iodopyridine.

Example 328

5-(5-Chloro-pyridin-3-ylamino)-2-methyl-thiazole-4-carboxylic acid (4-methyl-thiazol-2-yl)-amide The title compound, MS (ISP): m/e=366.0 (M+H$^+$), was prepared as for example 163, steps A to C. Step B was performed using 3,5-dichloropyridine and step C was performed using 2-amino-4-methylthiazole.

Example 329

2-Methyl-5-(2-methyl-pyridin-4-ylamino)-thiazole-4-carboxylic acid (4-methyl-thiazol-2-yl)-amide The title compound, MS (ISP): m/e=346.3 (M+H$^+$), was prepared as for example 223, steps A to E. Step C was performed using 2-amino-4-methylthiazole and step E was performed using 4-chloro-2-picoline.

Example 330

5-(4-Fluoro-pyridin-2-ylamino)-2-methyl-thiazole-4-carboxylic acid (4-methyl-thiazol-2-yl)-amide The title compound, MS (ISP): m/e=350.3 (M+H$^+$), was prepared as for example 223, steps A to E. Step C was performed using 2-amino-4-methylthiazole and step E was performed using 2-chloro-4-fluoropyridine.

Synthesis of Intermediates

Example A

5-Aminopyrimidine

The compound was synthesized as described in T. J. Kress, EP139477 A2.

Example B

3-Bromo-5-methanesulfonyl-pyridine

The compound was synthesized as described in T. Lu et al, WO2002060438 A1.

Example C

3-Amino-N-ethyl-benzenesulfonamide

The compound was synthesized as described in J. P. English et al, *J. Am. Chem. Soc.* 1946, 68, 1039-49.

Example D

2-Ethyl-4-amino-pyrimidine

The compound was synthesized as described in D. J. Buurmann et al, *J. Het. Chem.* 1987, 24, 1377-80.

Example E

5-Bromo-pyridine-3-sulfonic acid amide

The compound was synthesized as described in Y. Morisawa et al, *J. Med. Chem.* 1980, 23, 1376-80.

Example F

3-(3-Bromo-phenyl)-1-methyl-1H-pyrazole

The compound was synthesized as described in M. Bettati et al, WO 2002038568 A1.

Example G

5-Chloro-3-methyl-pyridazine

Step 1

3-Methyl-pyridazine-2-oxide

3-Methylpyridazine (10 g, 106 mmol) was dissolved in 62 mL acetic acid and hydrogen peroxide (30% in water, 58 mL, 568 mmol) was added. The reaction mixture was heated at reflux for 6 h and the solvents were evaporated. The residue was taken up in 200 mL water, neutralized with sodium carbonate and extracted three times with dichloromethane (150 mL each). The combined organic extracts were dried with magnesium sulfate, filtered and evaporated. The crude product was purified by three consecutive recrystallizations from toluene and the desired product was obtained as a white solid (800 mg, 6%).

Step 2

6-Methyl-4-nitro-pyridazine-1-oxide

3-Methyl-pyridazine-1-oxide (450 mg, 4.09 mmol) was dissolved in 2 mL conc. sulfuric acid. Nitric acid (0.47 mL, 11.4 mmol) was added dropwise and the reaction mixture was heated at reflux for 4 h. The reaction mixture was carefully poured into crushed ice and the mixture was extracted three times with dichloromethane (50 mL each). The combined organic extracts were dried with magnesium sulfate, filtered and evaporated. The crude product (270 mg, 42%) was used without any further purification for the next step.

Step 3

4-Bromo-6-methyl-pyridazine-1-oxide

6-Methyl-4-nitro-pyridazine-1-oxide (270 mg, 1.74 mmol) was dissolved in 2 mL acetic acid, acetyl bromide (650 mL, 8.7 mmol) was added and the reaction mixture was heated at reflux for 1 h. The reaction mixture was poured into crushed ice, the mixture was neutralized by addition of sodium hydroxide and extracted three times with dichloromethane (50 mL each). The combined organic extracts were dried with magnesium sulfate, filtered and evaporated. The crude product was purified by flash-chromatography on silica gel (heptane/ethyl acetate 80:20→30:70 gradient) and the desired product was obtained as a light brown solid (150 mg, 45%).

Step 4

5-Chloro-3-methyl-pyridazine

4-Bromo-6-methyl-pyridazine-1-oxide (150 mg, 0.79 mmol) was dissolved in 5 mL chloroform. Phosphorus trichloride (501 mg, 3.65 mmol, dissolved in 1 mL chloroform) was added at 0° C. The reaction mixture was stirred at room temperature for 36 h and then poured into crushed ice. The mixture was neutralized by addition of sodium carbonate and extracted three times with dichloromethane (50 mL each). The combined organic extracts were dried with magnesium sulfate, filtered and evaporated. The crude product was purified by flash-chromatography on silica gel (heptane/ethyl acetate 80:20→30:70 gradient) and the desired product was obtained as a brown oil (70 mg, 69%).

Example H

1-Methyl-1H-[1,2,4]triazol-3-ylamine

Methyl-3-nitro-1H-1,2,4-triazole (synthesized as described in R. W. Middleton et al, Synthesis 1984, 740-3) (613 mg, 4.8 mmol) was dissolved in 6 ml methanol. Palladium on charcoal (10%, 51 mg) and hydrazine monohydrate (543 mg, 11 mmol) were added. The reaction mixture was refluxed for 1.5 h. Palladium on charcoal was filtered off and washed with methanol. The solvent was evaporated off to yield the title compound (469 mg, 99%) as a white solid, MS (ISP): m/e=98.0 ($M^+$).

Example I

5-Difluoromethyl-pyridin-3-ylamine

Step 1

(5-Difluoromethyl-pyridin-3-yl)-carbamic acid tert-butyl ester (5-Formyl-pyridin-3-yl)-carbamic acid tert-butyl ester [CAS 337904-94-6] (1.75 g mmol) was dissolved in 40 ml dichloromethane. Diethylaminosulfur trifluoride (3.8 g, 24 mmol) was added and the reaction mixture was stirred at room temperature overnight. The reaction mixture was quenched by addition of 50 ml sat. NaHCO3 solution and extracted three time with 100 ml dichloromethane. The organic phases were pooled, dried with sodium sulfate and evaporated. The crude product was purified by flash chromatography (heptane/ethyl acetate 1:1) and the title compound was obtained as a yellow solid (0.39 g, 20%).

Step 2

5-Difluoromethyl-pyridin-3-ylamine (5-Difluoromethyl-pyridin-3-yl)-carbamic acid tert-butyl ester (0.30 g, 1.2 mmol) was dissolved in 10 ml ethyl acetate and 8M HCl in EtOH (3 ml, 25 mmol) were added. The reaction mixture was stirred at room temperature for 2 h. The reaction mixture was quenched by addition of 20 ml sat. NaHCO3 solution and extracted three time with 50 ml ethyl acetate. The organic phases were pooled, dried with sodium sulfate and evaporated. The title compound was obtained as a brown oil (0.158 g, 89%).

Example J

3-[1,2,3]Triazol-1-yl-phenylamine

Step 1

1-(3-Nitro-phenyl)-4-trimethylsilanyl-1H-[1,2,3]triazole

Azido-3-nitro-benzene (CAS:1516-59-2, 11.8 g, 72 mmol) were dissolved in 20 ml THF and 30 ml trimethylsilylacetylene. The reaction mixture was stirred at 60° C. for 3 days. The solvents were evaporated off and the title compound was obtained as a brown solid (16.9 g, 90%), mp 75-78° C.

Step 2

1-(3-Nitro-phenyl)-1H-[1,2,3]triazole 1-(3-Nitro-phenyl)-4-trimethylsilanyl-1H-[1,2,3]triazole (16.7 g, 64 mmol) tetrabutylammonium fluoride in THF (1M, 100 ml, 100 mmol) were stirred at room temperature for 24 h. The reaction mixture was diluted with ethyl acetate and washed with water and brine. The organic layer was dried with magnesium sulfate, filtered and evaporated. The crude product was purified by chromatography on silica gel (hexane/ethyl acetate 1:1) and the desired product was obtained as a brown solid (9.96 g, 82%), mp 80-83° C.

Step 3

3-[1,2,3]Triazol-1-yl-phenylamine 1-(3-Nitro-phenyl)-1H-[1,2,3]triazole (9.66 g, 51 mmol) were dissolved in 300 ml methanol and 70 ml THF. Palladium on charcoal (10%, 500 mg) were added and the reaction mixture was stirred with a hydrogen balloon for 36 h. Palladium on charcoal was filtered off and washed with methanol. The solvent was evaporated off to yield the title compound (8.3 g, 100%) as an off-white solid, mp 71-73° C.

Example K 3-(2-Methyl-imidazol-1-yl)-phenylamine

The compound was synthesized as described in J. C. Zhou et al, WO 2002008199.

Example L

1-Cyclopropylmethyl-1H-pyrazol-3-ylamine

3-Aminopyrazole (2.43 g, 29 mmol) were dissolved in 30 ml DMSO. Potassium hydroxide (4.8 g, 86 mmol) was added and the mixture was stirred at room temperature for 30 min. (Bromomethyl)cyclopropane (4.4 g, 32 mmol) was added and stirring was continued at room temperature overnight. The reaction mixture was poured into 100 ml brine and extracted three time with 100 ml ethyl acetate. The organic phases were pooled, dried with sodium sulfate and evaporated. The two regiosomers were separated by flash chromatography and the title compound was obtained as a brown oil (1.739 g, 31%).

Example M 2-(2,2,2-Trifluoro-ethyl)-2H-pyrazol-3-ylamine

The title compound, MS (ISP): m/e=166.4 (M+H$^+$), was prepared as for example L using 2,2,2-trifluoroethyl bromide. The two regiosomers were separated by flash chromatography and the title compound was obtained as a brown oil (7%).

Example N

4-Cyclopropyl-thiazol-2-ylamine

A solution of 2-Bromo-1-cyclopropyl-ethanone (CAS [69267-75-0], Indian J. Chem. Sect. B, 22(9), 841(1983) (1 g, 6.1 mmol) and thiourea (0.481 g, 6.1 mmol) in 15 ml of methanol was refluxed overnight. The solvent was evaporated off and the title compound was obtained as an off-white solid (1.38 g, 100%).

Example O 1-(2-Methoxy-ethyl)-1H-pyrazol-3-ylamine

3-Aminopyrazole (2 g, 23 mmol) were dissolved in 15 ml DMSO. Potassium hydroxide (3.8 g, 69 mmol) was added and the mixture was stirred at room temperature for 30 min. 2-Bromoethyl methyl ether (3.2 g, 23 mmol) was added and stirring was continued at room temperature overnight. The reaction mixture was poured into 100 ml brine and extracted three time with 100 ml ethyl acetate. The organic phases were pooled, dried with sodium sulfate and evaporated. The two regiosomers were separated by flash chromatography and the title compound was obtained as a brown oil (0.824 g, 25%), MS (ISP): m/e=142.1 (M+H$^+$).

Example P

3-Bromo-5-fluoropyridine

Step 1: 3-Amino-5-bromopyridine

To a ice-cold solution of 31.8 g (0.79 mol) of Sodium hydroxide and 40.7 g (0.255 mol) of Bromine in 340 ml of water were added 42.0 g (0.209 mol) of commercially available 5-Bromonicotinamide. The mixture was allowed to warm up to room temperature and then heated for 1 h at 70° C. The resulting brown suspension was allowed to cool to room temperature. The aqueous phase was saturated with brine and extracted three times with a 1:1 mixture of THF and t-Butylmethyl ether. The combined organic phases were dried over magnesium sulfate, filtered and concentrated in vaccuo. Concentration in vaccuo yielded 39.1 g of a dark brown residue which was purified by flash chromatography (heptane/ethyl acetate 1:1) to yield the title compound as a brown solid (total 70.2 g, 70%), MS (ISP): m/e=173.1, 175.1 (M+H+).

Step 2: 3-Bromo-5-fluoropyridine

A at −10° C. cooled solution of 10.0 g (0.058 mol) of 3-Amino-5-bromopyridine in 59 ml of 50% Tetrafluoroboric acid was treated by dropwise addition of a solution of 4.19 g (0.06 mol) of sodium nitrite in 13 ml of water. After stirring for 1 h at −8° C., 150 ml of ether was added to the brown suspension. The crude diazonium salt was filtered off, and washed with ether. This crude salt was then added in portions to 200 ml of toluene heated at 80° C. After stirring for 1 h at 90° C., the organic phase was concentrated. The light yellow residue was suspended in 150 ml of water and the pH was adjusted to 11 with 32% sodium hydroxide solution. The resulting solution was extracted three times with 200 ml of methylene chloride. The combined organic phases were washed with water, dried over magnesium sulfate and concentrated. The crude material 15.4 g (brown oil) was purified by vacuum distillation (10 mBar, 35° C.) and yielded 5.6 g (0.032 mol, 55%) of the title compound as a colorless oil (ISP): m/e=176.1, 178.1 (M+H$^+$).

The invention claimed is:

1. A compound of formula (I):

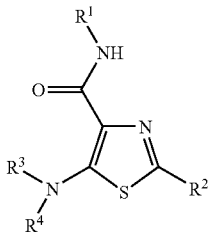

(I)

wherein $R^1$ is aryl or heteroaryl, each of which is optionally substituted by one or more substituents selected from the group consisting of —OH, chloro, fluoro, bromo, cyano, $C_1$-$C_7$-alkyl, $C_1$-$C_7$-alkoxy, —O—(CO)—$C_1$-$C_7$-alkyl, $C_3$-$C_6$-cycloalkyl, and —(CH$_2$)$_m$—$R^a$,
  wherein $R^a$ is —OH, —CH$_2$F, —CHF$_2$, —CF$_3$, $C_1$-$C_7$-alkoxy, $C_3$-$C_6$-cycloalkyl, —NH(CO)—$C_1$-$C_7$-alkyl, or —O—(CO)—$C_1$-$C_7$-alkyl;
$R^2$ is H, $C_1$-$C_7$-alkyl, —(CH$_2$)$_m$—O—$C_1$-$C_7$-alkyl or $C_3$-$C_6$-cycloalkyl;
$R^3$ is $C_1$-$C_7$-alkyl;
  —(CH$_2$)$_m$—$R^b$,
    wherein $R^b$ is —O—$C_1$-$C_7$-alkyl, $C_3$-$C_6$-cycloalkyl, 5 or 6 membered heterocycloalkyl, aryl optionally substituted by fluoro, or heteroaryl optionally substituted by $C_1$-$C_7$-alkyl;
  —(CO)—$R^c$,
    wherein $R^c$ is —O—(CH$_2$)$_m$—$C_3$-$C_6$-cycloalkyl, or aryl;
  $C_3$-$C_6$-cycloalkyl;
  5 or 6 membered heterocycloalkyl;
  aryl or heteroaryl, each of which is optionally substituted by
    cyano,
    chloro,
    fluoro,
    bromo,
    CF$_3$,
    CHF$_2$,
    $C_3$-$C_6$-cycloalkyl, or
    —O—$C_1$-$C_7$-alkyl;
  —(CO)—$R^d$,
    wherein $R^d$ is $C_1$-$C_7$-alkyl, NH$_2$, or —O—$C_1$-$C_7$-alkyl;
  —(CH$_2$)$_m$—$R^e$, wherein $R^e$ is OH, $C_1$-$C_7$-alkoxy, CHF$_2$, CF$_3$, NH$_2$, —NH—(CO)—$C_1$-$C_7$-alkyl, or —NH—(CO)—O—$C_1$-$C_7$-alkyl;
  —NH—(CO)—$C_1$-$C_7$-alkyl;
  —O—CH$_2$F;
  —O—CHF$_2$;
  —O—CF$_3$;
  —S(O)$_2$—$R^f$,
    wherein $R^f$ is $C_1$-$C_7$-alkyl, —NH$_2$, —NH—$C_1$-$C_7$-alkyl or —N-di($C_1$-$C_7$-alkyl); or heteroaryl optionally substituted by $C_1$-$C_7$-alkyl;
$R^4$ is H, $C_1$-$C_7$-alkyl or $C_1$-$C_7$-alkyl-$C_3$-$C_6$-cycloalkyl;
m is 1 to 4;
or a pharmaceutically acceptable salt thereof.

2. A compound of claim 1:

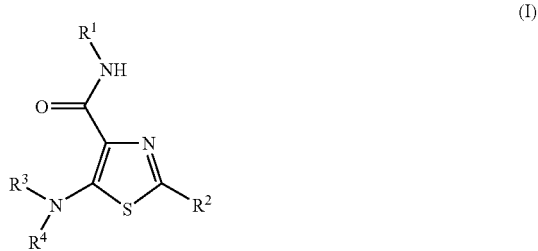

(I)

wherein $R^1$ is aryl or heteroaryl, each of which is optionally substituted by one or more substituents selected from the group consisting of —OH, chloro, fluoro, bromo, cyano, $C_1$-$C_7$-alkyl, —O—(CO)—$C_1$-$C_7$-alkyl, and —(CH$_2$)$_m$—$R^a$,
  wherein $R^a$ is —OH, —CH$_2$F, —CHF$_2$, —CF$_3$, or —O—(CO)—$C_1$-$C_7$-alkyl;
$R^2$ is H, $C_1$-$C_7$-alkyl, —(CH$_2$)$_m$—O—$C_1$-$C_7$-alkyl or $C_3$-$C_6$-cycloalkyl;
$R^3$ is $C_1$-$C_7$-alkyl;
  —(CH$_2$)$_m$—$R^b$,
    wherein $R^b$ is —O—$C_1$-$C_7$-alkyl, $C_3$-$C_6$-cycloalkyl, or aryl;
  —(CO)—$R^c$,
    wherein $R^c$ is —O—(CH$_2$)$_m$—$C_3$-$C_6$-cycloalkyl, or aryl;
  $C_3$-$C_6$-cycloalkyl;
  aryl or heteroaryl, each of which is optionally substituted by:
    cyano,
    chloro,
    fluoro,
    bromo,
    CF$_3$,
    CHF$_2$, or
    —O—$C_1$-$C_7$-alkyl;
  —(CO)—$R^d$,
    wherein $R^d$ is $C_1$-$C_7$-alkyl, NH$_2$, or —O—$C_1$-$C_7$-alkyl;
  —(CH$_2$)$_m$—$R^e$,
    wherein $R^e$ is OH, NH$_2$, or —NH—(CO)—O—$C_1$-$C_7$-alkyl;
  —NH—(CO)—$C_1$-$C_7$-alkyl;
  —O—CH$_2$F;
  —O—CHF$_2$;
  —O—CF$_3$;
  —S(O)$_2$—$R^f$, wherein $R^f$ is $C_1$-$C_7$-alkyl, —$NH_2$, —NH—$C_1$-$C_7$-alkyl or —N-di($C_1$-$C_7$-alkyl); or heteroaryl optionally substituted by $C_1$-$C_7$-alkyl;

$R^4$ is H, $C_1$-$C_7$-alkyl or $C_1$-$C_7$-alkyl-$C_3$-$C_6$-cycloalkyl;

m is 1 to 4;

or a pharmaceutically acceptable salt thereof.

3. A compound of claim 1, wherein $R^1$ is aryl or heteroaryl, each of which is optionally substituted by one or more substituent selected from the group consisting of —OH, chloro, fluoro, bromo, cyano, $C_1$-$C_7$-alkyl, $C_1$-$C_7$-alkoxy, —O—(CO)—$C_1$-$C_7$-alkyl, $C_3$-$C_6$-cycloalkyl, and —$(CH_2)_m$—$R^a$, wherein $R^a$ is —OH, —$CH_2F$, —$CF_3$, $C_1$-$C_7$-alkoxy, $C_3$-$C_6$-cycloalkyl, —NH(CO)—$C_1$-$C_7$-alkyl, or —O—(CO)—$C_1$-$C_7$-alkyl;

$R^2$ is H, $C_1$-$C_7$-alkyl, —$(CH_2)_m$—O—$C_1$-$C_7$-alkyl or $C_3$-$C_6$-cycloalkyl;

$R^3$ is $C_1$-$C_7$-alkyl;

—$(CH_2)_m$—$R^b$, wherein $R^b$ is —O—$C_1$-$C_7$-alkyl, $C_3$-$C_6$-cycloalkyl, 5 or 6 membered heterocycloalkyl, aryl optionally substituted by fluoro, or heteroaryl optionally substituted by $C_1$-$C_7$-alkyl;

—(CO)—$R^c$, wherein $R^c$ is —O—$(CH_2)_m$—$C_3$-$C_6$-cycloalkyl, or aryl;

$C_3$-$C_6$-cycloalkyl;

5 or 6 membered heterocycloalkyl;

aryl or heteroaryl, each of which is optionally substituted by:
cyano,
chloro,
fluoro,
bromo,
$CF_3$ or
—O—$C_1$-$C_7$-alkyl;

—(CO)—$R^d$, wherein $R^d$ is $C_1$-$C_7$-alkyl, $NH_2$, or —O—$C_1$-$C_7$-alkyl;

—$(CH_2)_m$—$R^e$, wherein $R^e$ is OH, $C_1$-$C_7$-alkoxy, $CHF_2$, $CF_3$, $NH_2$, —NH—(CO)—$C_1$-$C_7$-alkyl, or —NH—(CO)—O—$C_1$-$C_7$-alkyl;

—NH—(CO)—$C_1$-$C_7$-alkyl;

—O—$CHF_2$;

—$S(O)_2$—$R^f$, wherein $R^f$ is $C_1$-$C_7$-alkyl, —$NH_2$, —NH—$C_1$-$C_7$-alkyl or —N-di($C_1$-$C_7$-alkyl); or heteroaryl optionally substituted by $C_1$-$C_7$-alkyl;

$R^4$ is H, $C_1$-$C_7$-alkyl or $C_1$-$C_7$-alkyl-$C_3$-$C_6$-cycloalkyl;

m is 1 to 4;

or a pharmaceutically acceptable salt thereof.

4. A compound of claim 1, wherein $R^3$ is heteroaryl optionally substituted by
cyano,
chloro,
fluoro,
bromo,
$CF_3$,
$CHF_2$, or
—O—$C_1$-$C_7$-alkyl;
—(CO)—$R^d$, wherein $R^d$ is $C_1$-$C_7$-alkyl, $NH_2$, or —O—$C_1$-$C_7$-alkyl;

—$(CH_2)_m$—$R^e$, wherein $R^e$ is OH, $C_1$-$C_7$-alkoxy, $CHF_2$, $CF_3$, $NH_2$, —NH—(CO)—$C_1$-$C_7$-alkyl, or —NH—(CO)—O—$C_1$-$C_7$-alkyl;

—NH—(CO)—$C_1$-$C_7$-alkyl;

—O—$CH_2F$;

—O—$CHF_2$;

—O—$CF_3$;

—$S(O)_2$—$R^f$, wherein $R^f$ is $C_1$-$C_7$-alkyl, —$NH_2$, —NH—$C_1$-$C_7$-alkyl or —N-di($C_1$-$C_7$-alkyl); or heteroaryl optionally substituted by $C_1$-$C_7$-alkyl.

5. A compound of claim 4, wherein $R^3$ is heteroaryl optionally substituted by
cyano,
chloro,
fluoro,
bromo,
$CF_3$,
$CHF_2$, or
—O—$C_1$-$C_7$-alkyl; or
heteroaryl optionally substituted by $C_1$-$C_7$-alkyl.

6. A compound of claim 5, wherein $R^3$ is pyridine, pyridazine, pyrimidine, or pyrazine.

7. A compound of 4, selected from the group consisting of:

5-(Pyridin-3-ylamino)-thiazole-4-carboxylic acid (6-methyl-pyridin-2-yl)-amide;

5-(Pyridin-3-ylamino)-thiazole-4-carboxylic acid (3-chloro-phenyl)-amide;

5-(Pyridin-3-ylamino)-thiazole-4-carboxylic acid (6-chloro-pyridin-2-yl)-amide;

5-(Pyridin-3-ylamino)-thiazole-4-carboxylic acid (6-bromo-pyridin-2-yl)-amide;

5-(Pyridin-3-ylamino)-thiazole-4-carboxylic acid (4-methyl-thiazol-2-yl)-amide;

5-(Pyridin-3-ylamino)-thiazole-4-carboxylic acid (2-methyl-thiazol-4-yl)-amide;

5-(Pyridin-3-ylamino)-thiazole-4-carboxylic acid m-tolylamide;

5-(Pyridin-3-ylamino)-thiazole-4-carboxylic acid (6-ethyl-pyridin-2-yl)-amide;

5-(Pyridin-3-ylamino)-thiazole-4-carboxylic acid (6-trifluoromethyl-pyridin-2-yl)-amide;

5-(3,5-Dimethyl-isoxazol-4-ylamino)-thiazole-4-carboxylic acid (3-chloro-phenyl)-amide;

5-(3,5-Dimethyl-isoxazol-4-ylamino)-thiazole-4-carboxylic acid m-tolylamide;

5-(3,5-Dimethyl-isoxazol-4-ylamino)-thiazole-4-carboxylic acid (6-methyl-pyridin-2-yl)-amide;

5-(3,5-Dimethyl-isoxazol-4-ylamino)-thiazole-4-carboxylic acid (6-bromo-pyridin-2-yl)-amide;

5-(3,5-Dimethyl-isoxazol-4-ylamino)-thiazole-4-carboxylic acid (4-methyl-thiazol-2-yl)-amide;

5-(2-Methoxy-pyridin-3-ylamino)-thiazole-4-carboxylic acid (6-methyl-pyridin-2-yl)-amide;

2-Methyl-5-(pyridin-3-ylamino)-thiazole-4-carboxylic acid (3-chloro-phenyl)-amide;

2-Methyl-5-(pyridin-3-ylamino)-thiazole-4-carboxylic acid (6-methyl-pyridin-2-yl)-amide;

2-Methyl-5-(pyridin-3-ylamino)-thiazole-4-carboxylic acid (2-methyl-thiazol-4-yl)-amide;

2-Methyl-5-(pyridin-3-ylamino)-thiazole-4-carboxylic acid (6-chloro-pyridin-2-yl)-amide;

2-Methyl-5-(pyridin-3-ylamino)-thiazole-4-carboxylic acid (6-bromo-pyridin-2-yl)-amide;

2-Methyl-5-(pyridin-3-ylamino)-thiazole-4-carboxylic acid (3-cyano-phenyl)-amide;

2-Methyl-5-(pyridin-3-ylamino)-thiazole-4-carboxylic acid (2-fluoro-5-methyl-phenyl)-amide;

2-Methyl-5-(pyridin-3-ylamino)-thiazole-4-carboxylic acid (5-chloro-2-fluoro-phenyl)-amide;

2-Methyl-5-(pyridin-3-ylamino)-thiazole-4-carboxylic acid (3-chloro-2-fluoro-phenyl)-amide;
2-Methyl-5-(pyridin-3-ylamino)-thiazole-4-carboxylic acid m-tolylamide;
2-Methyl-5-(pyridin-3-ylamino)-thiazole-4-carboxylic acid (6-fluoromethyl-pyridin-2-yl)-amide;
2-Methyl-5-(pyridin-3-ylamino)-thiazole-4-carboxylic acid (2-chloro-pyridin-4-yl)-amide;
2-Methyl-5-(pyridin-3-ylamino)-thiazole-4-carboxylic acid (2-methyl-pyridin-4-yl)-amide;
2-Methyl-5-(pyridin-3-ylamino)-thiazole-4-carboxylic acid (5-fluoro-pyridin-2-yl)-amide;
2-Methyl-5-(pyridin-3-ylamino)-thiazole-4-carboxylic acid (2-methyl-pyrimidin-4-yl)-amide;
2-Methyl-5-(pyrimidin-5-ylamino)-thiazole-4-carboxylic acid (6-chloro-pyridin-2-yl)-amide;
2-Methyl-5-(pyridin-4-ylamino)-thiazole-4-carboxylic acid (4-methyl-thiazol-2-yl)-amide;
5-(3,5-Difluoromethyl-pyridin-3-ylamino)-2-methyl-thiazole-4-carboxylic acid (4-methyl-thiazol-2-yl)-amide.

8. A compound of 4, selected from the group consisting of:
2-Methyl-5-(pyrimidin-5-ylamino)-thiazole-4-carboxylic acid (6-methyl-pyridin-2-yl)-amide;
2-Methyl-5-(pyrimidin-5-ylamino)-thiazole-4-carboxylic acid (2-methyl-thiazol-4-yl)-amide;
2-Methyl-5-(pyrimidin-5-ylamino)-thiazole-4-carboxylic acid (2-methyl-pyridin-4-yl)-amide;
2-Methyl-5-(pyrimidin-5-ylamino)-thiazole-4-carboxylic acid (5-fluoro-pyridin-2-yl)-amide;
2-Methyl-5-(pyrimidin-5-ylamino)-thiazole-4-carboxylic acid (3-chloro-phenyl)-amide;
2-Methyl-5-(4-methyl-pyridin-3-ylamino)-thiazole-4-carboxylic acid (3-chloro-phenyl)-amide;
2-Methyl-5-(4-methyl-pyridin-3-ylamino)-thiazole-4-carboxylic acid (6-methyl-pyridin-2-yl)-amide;
2-Methyl-5-(4-methyl-pyridin-3-ylamino)-thiazole-4-carboxylic acid (2-methyl-pyridin-4-yl)-amide;
5-(5-Cyano-pyridin-3-ylamino)-2-methyl-thiazole-4-carboxylic acid (3-chloro-phenyl)-amide;
5-(5-Cyano-pyridin-3-ylamino)-2-methyl-thiazole-4-carboxylic acid (6-methyl-pyridin-2-yl)-amide;
5-Amino-2-methyl-thiazole-4-carboxylic acid (3-chloro-phenyl)-amide;
2-Methyl-5-(pyridin-4-ylamino)-thiazole-4-carboxylic acid (3-chloro-phenyl)-amide;
2-Methyl-5-(2-methyl-pyridin-3-ylamino)-thiazole-4-carboxylic acid (6-methyl-pyridin-2-yl)-amide;
2-Methyl-5-(pyrazin-2-ylamino)-thiazole-4-carboxylic acid (6-methyl-pyridin-2-yl)-amide;
2-Methyl-5-(pyrimidin-2-ylamino)-thiazole-4-carboxylic acid (6-methyl-pyridin-2-yl)-amide;
2-Methyl-5-(pyridin-2-ylamino)-thiazole-4-carboxylic acid (6-methyl-pyridin-2-yl)-amide;
2-Methyl-5-(pyridazin-3-ylamino)-thiazole-4-carboxylic acid (6-methyl-pyridin-2-yl)-amide;
Acetic acid 6-{[2-methyl-5-(pyridin-3-ylamino)-thiazole-4-carbonyl]-amino}-pyridin-2-ylmethyl ester;
2-Methyl-5-(pyridin-3-ylamino)-thiazole-4-carboxylic acid (6-hydroxymethyl-pyridin-2-yl)-amide;
2-Methyl-5-(pyrimidin-5-ylamino)-thiazole-4-carboxylic acid (6-hydroxymethyl-pyridin-2-yl)-amide;
Acetic acid 2-methyl-6-{[2-methyl-5-(pyridin-3-ylamino)-thiazole-4-carbonyl]-amino}-pyridin-3-yl ester;
2-Methyl-5-(pyridin-3-ylamino)-thiazole-4-carboxylic acid (5-hydroxy-6-methyl-pyridin-2-yl)-amide;
2-Methyl-5-(pyrimidin-5-ylamino)-thiazole-4-carboxylic acid (5-hydroxy-6-methyl-pyridin-2-yl)-amide;
2-(2-Methoxy-ethyl)-5-(pyridin-3-ylamino)-thiazole-4-carboxylic acid (6-methyl-pyridin-2-yl)-amide;
2-Methoxymethyl-5-(pyridin-3-ylamino)-thiazole-4-carboxylic acid (6-methyl-pyridin-2-yl)-amide;
2-Cyclopropyl-5-(pyridin-3-ylamino)-thiazole-4-carboxylic acid (6-methyl-pyridin-2-yl)-amide;
2-Cyclobutyl-5-(pyridin-3-ylamino)-thiazole-4-carboxylic acid (6-methyl-pyridin-2-yl)-amide;
2-Ethyl-5-(pyridin-3-ylamino)-thiazole-4-carboxylic acid (6-methyl-pyridin-2-yl)-amide;
2-Propyl-5-(pyridin-3-ylamino)-thiazole-4-carboxylic acid (6-methyl-pyridin-2-yl)-amide;
2-Isopropyl-5-(pyridin-3-ylamino)-thiazole-4-carboxylic acid (6-methyl-pyridin-2-yl)-amide;
2-Methyl-5-(2-methyl-pyridin-3-ylamino)-thiazole-4-carboxylic acid (5-fluoro-pyridin-2-yl)-amide;
2-Methyl-5-(pyrimidin-2-ylamino)-thiazole-4-carboxylic acid (4-methyl-thiazol-2-yl)-amide; and
2-Methyl-5-[(pyridin-3-ylmethyl)-amino]-thiazole-4-carboxylic acid (4-methyl-thiazol-2-yl)-amide.

9. A compound of 4, selected from the group consisting of:
2-Methyl-5-((6-trifluoromethyl-pyridin-3-yl)amino)-thiazole-4-carboxylic acid (2-methyl-pyridin-4-yl)-amide;
2-Methyl-5-(2-methyl-pyridin-3-ylamino)-thiazole-4-carboxylic acid (2-methyl-pyridin-4-yl)-amide;
2-Methyl-5-(pyrazin-2-ylamino)-thiazole-4-carboxylic acid (5-fluoro-pyridin-2-yl)-amide;
5-(5-Chloro-pyridin-3-ylamino)-2-methyl-thiazole-4-carboxylic acid (5-fluoro-pyridin-2-yl)-amide;
2-Methyl-5-(4-methyl-pyridin-2-ylamino)-thiazole-4-carboxylic acid (5-fluoro-pyridin-2-yl)-amide;
2-Methyl-5-(pyrimidin-5-ylamino)-thiazole-4-carboxylic acid (2-chloro-pyridin-4-yl)-amide;
2-Methyl-5-(2-methyl-pyridin-4-ylamino)-thiazole-4-carboxylic acid (5-fluoro-pyridin-2-yl)-amide;
2-Methyl-5-(2-methyl-pyridin-3-ylamino)-thiazole-4-carboxylic acid (2-chloro-pyridin-4-yl)-amide;
2-Methyl-5-(pyrazin-2-ylamino)-thiazole-4-carboxylic acid (2-chloro-pyridin-4-yl)-amide;
5-(5-Chloro-pyridin-3-ylamino)-2-methyl-thiazole-4-carboxylic acid (2-methyl-pyridin-4-yl)-amide;
5-(5-Chloro-pyridin-3-ylamino)-2-methyl-thiazole-4-carboxylic acid (2-chloro-pyridin-4-yl)-amide;
5-(5-Cyano-pyridin-3-ylamino)-2-methyl-thiazole-4-carboxylic acid (5-fluoro-pyridin-2-yl)-amide;
5-(5-Cyano-pyridin-3-ylamino)-2-methyl-thiazole-4-carboxylic acid (2-methyl-pyrimidin-4-yl)-amide;
2-Methyl-5-(4-methyl-pyridin-3-ylamino)-thiazole-4-carboxylic acid (5-fluoro-pyridin-2-yl)-amide;
2-Methyl-5-(pyrimidin-5-ylamino)-thiazole-4-carboxylic acid (2-methyl-pyrimidin-4-yl)-amide;
5-(5-Cyano-pyridin-3-ylamino)-2-methyl-thiazole-4-carboxylic acid (2-methyl-pyridin-4-yl)-amide;
5-(5-Cyano-pyridin-3-ylamino)-2-methyl-thiazole-4-carboxylic acid (4-methyl-pyrimidin-2-yl)-amide;
2-Methyl-5-(4-methyl-pyridin-3-ylamino)-thiazole-4-carboxylic acid (2-chloro-pyridin-4-yl)-amide;
5-(5-Methanesulfonyl-pyridin-3-ylamino)-2-methyl-thiazole-4-carboxylic acid (2-methyl-pyridin-4-yl)-amide;
2-Methyl-5-(6-methyl-pyridazin-4-ylamino)-thiazole-4-carboxylic acid (2-methyl-pyridin-4-yl)-amide;
2-Methyl-5-(6-methyl-pyridazin-4-ylamino)-thiazole-4-carboxylic acid (2-chloro-pyridin-4-yl)-amide;
5-(Isoxazol-3-ylamino)-2-methyl-thiazole-4-carboxylic acid (2-methyl-pyrimidin-4-yl)-amide;

5-(4-Cyano-pyridin-2-ylamino)-2-methyl-thiazole-4-carboxylic acid (2-methyl-pyridin-4-yl)-amide;
5-(2-Chloro-pyridin-4-ylamino)-2-methyl-thiazole-4-carboxylic acid (2-methyl-pyridin-4-yl)-amide;
5-(4-Chloro-pyridin-2-ylamino)-2-methyl-thiazole-4-carboxylic acid (2-methyl-pyrimidin-4-yl)-amide;
2-Methyl-5-(pyrimidin-5-ylamino)-thiazole-4-carboxylic acid (3-chloro-4-fluoro-phenyl)-amide;
5-(5-Methanesulfonyl-pyridin-3-ylamino)-2-methyl-thiazole-4-carboxylic acid (6-fluoro-pyridin-3-yl)-amide;
5-(5-Methanesulfonyl-pyridin-3-ylamino)-2-methyl-thiazole-4-carboxylic acid (2-methyl-pyrimidin-4-yl)-amide;
2-Methyl-5-(pyrimidin-5-ylamino)-thiazole-4-carboxylic acid (4-fluoro-3-methyl-phenyl)-amide;
2-Methyl-5-(pyridin-3-ylamino)-thiazole-4-carboxylic acid (2-ethyl-pyrimidin-4-yl)-amide;
2-Methyl-5-(pyridin-3-ylamino)-thiazole-4-carboxylic acid (5-methyl-4H-[1,2,4]triazol-3-yl)-amide; and
2-Methyl-5-(pyridin-3-ylamino)-thiazole-4-carboxylic acid (4-methoxymethyl-thiazol-2-yl)-amide.

10. A compound of 4, selected from the group consisting of:
2-Methyl-5-(5-methyl-pyridin-3-ylamino)-thiazole-4-carboxylic acid (5-fluoro-pyridin-2-yl)-amide;
5-(2-Chloro-pyridin-4-ylamino)-2-methyl-thiazole-4-carboxylic acid (2-methyl-pyrimidin-4-yl)-amide;
5-(5-Methoxy-pyridin-3-ylamino)-2-methyl-thiazole-4-carboxylic acid (2-methyl-pyridin-4-yl)-amide;
2-Methyl-5-(5-methyl-pyridin-3-ylamino)-thiazole-4-carboxylic acid (2-methyl-pyridin-4-yl)-amide;
5-(5-Fluoro-pyridin-3-ylamino)-2-methyl-thiazole-4-carboxylic acid (2-methyl-pyridin-4-yl)-amide;
2-Methyl-5-(2-methyl-2H-pyrazol-3-ylamino)-thiazole-4-carboxylic acid (2-methyl-pyridin-4-yl)-amide;
2-Methyl-5-(pyridin-3-ylamino)-thiazole-4-carboxylic acid (4-methyl-pyrimidin-2-yl)-amide;
2-Methyl-5-(pyridin-2-ylamino)-thiazole-4-carboxylic acid (2-chloro-pyridin-4-yl)-amide;
2-Methyl-5-((5-trifluoromethyl-pyridin-3-yl)amino)-thiazole-4-carboxylic acid (2-methyl-pyridin-4-yl)-amide;
5-(4-Fluoro-pyridin-2-ylamino)-2-methyl-thiazole-4-carboxylic acid (2-methyl-pyridin-4-yl)-amide;
5-(2-Chloro-pyridin-4-ylamino)-2-methyl-thiazole-4-carboxylic acid (2-chloro-pyridin-4-yl)-amide;
5-(5-Hydroxymethyl-pyridin-3-ylamino)-2-methyl-thiazole-4-carboxylic acid (2-methyl-pyridin-4-yl)-amide;
5-(2-Cyano-pyridin-4-ylamino)-2-methyl-thiazole-4-carboxylic acid (2-methyl-pyridin-4-yl)-amide;
2-Methyl-5-(2-methyl-2H-pyrazol-3-ylamino)-thiazole-4-carboxylic acid (2-chloro-pyridin-4-yl)-amide;
5-[2-Methyl-4-(2-methyl-pyridin-4-ylcarbamoyl-thiazol-5-ylamino]-nicotinamide;
2-Methyl-5-(5-sulfamoyl-pyridin-3-ylamino)-thiazole-4-carboxylic acid (2-methyl-pyridin-4-yl)-amide;
5-(5-Fluoro-pyridin-3-ylamino)-2-methyl-thiazole-4-carboxylic acid (2-chloro-pyridin-4-yl)-amide;
5-(5-Fluoro-pyridin-3-ylamino)-2-methyl-thiazole-4-carboxylic acid (4-methyl-thiazol-2-yl)-amide;
5-(5-Fluoro-pyridin-3-ylamino)-2-methyl-thiazole-4-carboxylic acid (2-methyl-pyrimidin-4-yl)-amide;
5-(4-Fluoro-pyridin-2-ylamino)-2-methyl-thiazole-4-carboxylic acid (2-methyl-pyrimidin-4-yl)-amide;
5-(5-Fluoro-pyridin-3-ylamino)-2-methyl-thiazole-4-carboxylic acid (5-fluoro-pyridin-2-yl)-amide;
5-(5-Fluoro-pyridin-3-ylamino)-2-methyl-thiazole-4-carboxylic acid (1-methyl-1H-pyrazol-3-yl)-amide;
2-Methyl-5-[pyridin-3-ylmethyl)-amino]-thiazole-4-carboxylic acid (2-methyl-pyridin-4-yl)-amide;
2-Methyl-5-(2-methyl-2H-pyrazol-3-ylamino)-thiazole-4-carboxylic acid (2-methyl-pyrimidin-4-yl)-amide;
5-(2-Ethyl-2H-pyrazol-3-ylamino)-2-methyl-thiazole-4-carboxylic acid (2-methyl-pyrimidin-4-yl)-amide;
5-(2,5-Dimethyl-2H-pyrazol-3-ylamino)-2-methyl-thiazole-4-carboxylic acid (2-methyl-pyrimidin-4-yl)-amide;
2-Methyl-5-(1-methyl-1H-pyrazol-4-ylamino)-thiazole-4-carboxylic acid (2-methyl-pyrimidin-4-yl)-amide;
2-Methyl-5-(3-methyl-isoxazol-5-ylamino)-thiazole-4-carboxylic acid (2-methyl-pyrimidin-4-yl)-amide;
2-Methyl-5-(1-methyl-1H-pyrazol-3-ylamino)-thiazole-4-carboxylic acid (2-methyl-pyrimidin-4-yl)-amide;
2-Methyl-5-(1-methyl-1H-pyrazol-4-ylamino)-thiazole-4-carboxylic acid (2-methyl-pyridin-4-yl)-amide;
5-(5-Cyano-pyridin-3-ylamino)-2-methyl-thiazole-4-carboxylic acid (4-methyl-thiazol-2-yl)-amide;
5-(5-Fluoro-pyridin-3-ylamino)-2-methyl-thiazole-4-carboxylic acid (2-methyl-thiazol-4-yl)-amide; and
5-(2-Chloro-pyridin-4-ylamino)-2-methyl-thiazole-4-carboxylic acid (2-methyl-thiazol-4-yl)-amide.

11. A compound of 4, selected from the group consisting of:
5-(5-Difluoromethyl-pyridin-3-ylamino)-2-methyl-thiazole-4-carboxylic acid (2-methyl-pyridin-4-yl)-amide;
5-(5-Fluoro-pyridin-3-ylamino)-2-methyl-thiazole-4-carboxylic acid (4-trifluoromethyl-thiazol-2-yl)-amide;
2-Methyl-5-(thiazol-2-ylamino)-thiazole-4-carboxylic acid (2-methyl-pyridin-4-yl)-amide;
5-(5-Chloro-pyridin-3-ylamino)-2-methyl-thiazole-4-carboxylic acid (1-methyl-1H-pyrazol-3-yl)-amide;
2-Methyl-5-(pyrimidin-5-ylamino)-thiazole-4-carboxylic acid (1-methyl-1H-pyrazol-3-yl)-amide;
5-(4-Cyano-2-methyl-2H-pyrazol-3-ylamino)-2-methyl-thiazole-4-carboxylic acid (2-methyl-pyridin-4-yl)-amide;
5-(5-Cyclopropyl-2-methyl-2H-pyrazol-3-ylamino)-2-methyl-thiazole-4-carboxylic acid (2-methyl-pyridin-4-yl)-amide;
2-Methyl-5-(2-methyl-2H-pyrazol-3-ylamino)-thiazole-4-carboxylic acid (1-methyl-1H-pyrazol-3-yl)-amide;
5-(2-Chloro-pyridin-4-ylamino)-2-methyl-thiazole-4-carboxylic acid (1-methyl-1H-pyrazol-3-yl)-amide;
2-Methyl-5-[2-(2,2,2-trifluoro-ethyl)-2H-pyrazol-3-ylamino]-thiazole-4-carboxylic acid (2-methyl-pyridin-4-yl)-amide;
5-(5-Cyclopropyl-2-methyl-2H-pyrazol-3-ylamino)-2-methyl-thiazole-4-carboxylic acid (1-methyl-1H-pyrazol-3-yl)-amide;
5-(5-Cyclopropyl-2-methyl-2H-pyrazol-3-ylamino)-2-methyl-thiazole-4-carboxylic acid (4-trifluoromethyl-thiazol-2-yl)-amide;
2-Methyl-5-(2-methyl-5-trifluoromethyl-2H-pyrazol-3-ylamino)-thiazole-4-carboxylic acid (2-methyl-pyridin-4-yl)-amide;
5-(5-Fluoro-pyridin-3-ylamino)-2-methyl-thiazole-4-carboxylic acid (4-cyclopropyl-thiazol-2-yl)-amide;
5-(5-Fluoro-pyridin-3-ylamino)-2-methyl-thiazole-4-carboxylic acid (3-methoxymethyl-phenyl)-amide;
5-(5-Fluoro-pyridin-3-ylamino)-2-methyl-thiazole-4-carboxylic acid [1-(2-methoxy-ethyl)-1H-pyrazol-3-yl]-amide;
2-Methyl-5-(pyridin-3-ylamino)-thiazole-4-carboxylic acid (4-trifluoromethyl-thiazol-2-yl)-amide;

2-Methyl-5-(pyridin-3-ylamino)-thiazole-4-carboxylic acid (1-methyl-1H-pyrazol-3-yl)-amide;
2-Methyl-5-(pyridin-3-ylamino)-thiazole-4-carboxylic acid [1-(2-methoxy-ethyl)-1H-pyrazol-3-yl]-amide;
2-Methyl-5-(pyridin-3-ylamino)-thiazole-4-carboxylic acid (4-cyclopropyl-thiazol-2-yl)-amide;
2-Methyl-5-(pyridin-3-ylamino)-thiazole-4-carboxylic acid (4-methyl-thiazol-2-yl)-amide;
2-Methyl-5-(pyridin-3-ylamino)-thiazole-4-carboxylic acid thiazol-2-ylamide;
5-(5-Cyclopropyl-2-methyl-2H-pyrazol-3-ylamino)-2-methyl-thiazole-4-carboxylic acid (4-methyl-thiazol-2-yl)-amide;
5-(2-Chloro-pyridin-4-ylamino)-2-methyl-thiazole-4-carboxylic acid (4-methyl-thiazol-2-yl)-amide;
2-Methyl-5-(pyridin-3-ylamino)-thiazole-4-carboxylic acid (5-ethyl-thiazol-2-yl)-amide;
2-Methyl-5-(pyrimidin-5-ylamino)-thiazole-4-carboxylic acid (4-methyl-thiazol-2-yl)-amide;
2-Methyl-5-(1-methyl-1H-pyrazol-4-ylamino)-thiazole-4-carboxylic acid (4-methyl-thiazol-2-yl)-amide;
2-Methyl-5-(pyridin-2-ylamino)-thiazole-4-carboxylic acid (4-methyl-thiazol-2-yl)-amide;
5-(2,5-Dimethyl-2H-pyrazol-3-ylamino)-2-methyl-thiazole-4-carboxylic acid (4-methyl-thiazol-2-yl)-amide;
2-Methyl-5-(1-methyl-1H-pyrazol-3-ylamino)-thiazole-4-carboxylic acid (4-methyl-thiazol-2-yl)-amide;
5-(5-Chloro-pyridin-3-ylamino)-2-methyl-thiazole-4-carboxylic acid (4-methyl-thiazol-2-yl)-amide;
2-Methyl-5-(2-methyl-pyridin-4-ylamino)-thiazole-4-carboxylic acid (4-methyl-thiazol-2-yl)-amide; and
5-(4-Fluoro-pyridin-2-ylamino)-2-methyl-thiazole-4-carboxylic acid (4-methyl-thiazol-2-yl)-amide.

12. A compound of claim 1, wherein R³ is aryl optionally substituted by
cyano,
chloro,
fluoro,
bromo,
CF₃,
CHF₂, or
—O—C₁-C₇-alkyl; or
—(CO)—R$^d$,
wherein R$^d$ is C₁-C₇-alkyl, NH₂, or —O—C₁-C₇-alkyl;
—(CH₂)$_m$—R$^e$,
wherein R$^e$ is OH, NH₂, or —NH—(CO)—O—C₁-C₇-alkyl;
—NH—(CO)—C₁-C₇-alkyl;
—O—CH₂F;
—O—CHF₂;
—O—CF₃;
—S(O)₂—R$^f$,
wherein R$^f$ is C₁-C₇-alkyl, —NH₂, —NH—C₁-C₇-alkyl or —N-di(C₁-C₇-alkyl); or heteroaryl optionally substituted by C₁-C₇-alkyl.

13. A compound of claim 12, selected from the group consisting of
5-Phenylamino-thiazole-4-carboxylic acid phenylamide;
5-Phenylamino-thiazole-4-carboxylic acid (3-chloro-phenyl)-amide;
5-Phenylamino-thiazole-4-carboxylic acid (3-fluoro-phenyl)-amide;
5-Phenylamino-thiazole-4-carboxylic acid (6-methyl-pyridin-2-yl)-amide;
5-Phenylamino-thiazole-4-carboxylic acid (6-chloro-pyridin-2-yl)-amide;
5-Phenylamino-thiazole-4-carboxylic acid thiazol-2-ylamide;
5-Phenylamino-thiazole-4-carboxylic acid (4-methyl-thiazol-2-yl)-amide;
5-(3-Chloro-phenylamino)-thiazole-4-carboxylic acid (3-chloro-phenyl)-amide;
5-(2,6-Dichloro-phenylamino)-thiazole-4-carboxylic acid (3-chloro-phenyl)-amide;
5-(2,6-Dichloro-phenylamino)-thiazole-4-carboxylic acid m-tolylamide;
5-(2,6-Dichloro-phenylamino)-thiazole-4-carboxylic acid (6-methyl-pyridin-2-yl)-amide;
5-(2,6-Dichloro-phenylamino)-thiazole-4-carboxylic acid (6-bromo-pyridin-2-yl)-amide;
5-(2,6-Dichloro-phenylamino)-thiazole-4-carboxylic acid (4-methyl-thiazol-2-yl)-amide;
5-(3-Cyano-phenylamino)-thiazole-4-carboxylic acid (3-chloro-phenyl)-amide;
5-(3-Cyano-phenylamino)-thiazole-4-carboxylic acid m-tolylamide;
5-(3-Cyano-phenylamino)-thiazole-4-carboxylic acid (6-methyl-pyridin-2-yl)-amide;
5-(3-Cyano-phenylamino)-thiazole-4-carboxylic acid (6-bromo-pyridin-2-yl)-amide;
5-(3-Cyano-phenylamino)-thiazole-4-carboxylic acid (4-methyl-thiazol-2-yl)-amide;
5-(3-Cyano-phenylamino)-thiazole-4-carboxylic acid (2-methyl-thiazol-4-yl)-amide;
5-o-Tolylamino-thiazole-4-carboxylic acid (3-chloro-phenyl)-amide;
5-o-Tolylamino-thiazole-4-carboxylic acid m-tolylamide;
5-o-Tolylamino-thiazole-4-carboxylic acid (6-methyl-pyridin-2-yl)-amide;
5-o-Tolylamino-thiazole-4-carboxylic acid (4-methyl-thiazol-2-yl)-amide;
5-(2-Bromo-phenylamino)-thiazole-4-carboxylic acid (6-methyl-pyridin-2-yl)-amide;
5-(3-Acetyl-phenylamino)-thiazole-4-carboxylic acid (6-methyl-pyridin-2-yl)-amide;
5-(3,5-Dimethoxy-phenylamino)-thiazole-4-carboxylic acid (6-methyl-pyridin-2-yl)-amide;
5-(3,5-Dimethoxy-phenylamino)-thiazole-4-carboxylic acid m-tolylamide;
5-(3-Methoxy-phenylamino)-thiazole-4-carboxylic acid (6-methyl-pyridin-2-yl)-amide;
5-(3-Fluoro-phenylamino)-thiazole-4-carboxylic acid (6-methyl-pyridin-2-yl)-amide;
5-(2-Fluoro-phenylamino)-thiazole-4-carboxylic acid (6-methyl-pyridin-2-yl)-amide;
5-(4-Fluoro-phenylamino)-thiazole-4-carboxylic acid (6-methyl-pyridin-2-yl)-amide; and
5-(2,5-Difluoro-phenylamino)-thiazole-4-carboxylic acid (6-methyl-pyridin-2-yl)-amide.

14. A compound of claim 12, selected from the group consisting of
5-(2,6-Difluoro-phenylamino)-thiazole-4-carboxylic acid (6-methyl-pyridin-2-yl)-amide;
5-(3,5-Difluoro-phenylamino)-thiazole-4-carboxylic acid (6-methyl-pyridin-2-yl)-amide;
5-(2,3-Difluoro-phenylamino)-thiazole-4-carboxylic acid (6-methyl-pyridin-2-yl)-amide;
5-(2,5-Difluoro-phenylamino)-thiazole-4-carboxylic acid (2-methyl-pyrimidin-4-yl)-amide;
3-[4-(3-Chloro-phenylcarbamoyl)-2-methyl-thiazol-5-ylamino]-benzoic acid methyl ester;
5-(3-Hydroxymethyl-phenylamino)-2-methyl-thiazole-4-carboxylic acid (3-chloro-phenyl)-amide;

5-(3-Acetylamino-phenylamino)-2-methyl-thiazole-4-carboxylic acid (3-chloro-phenyl)-amide;
2-Methyl-5-(3-sulfamoyl-phenylamino)-thiazole-4-carboxylic acid (3-chloro-phenyl)-amide;
{3-[4-(3-Chloro-phenylcarbamoyl)-2-methyl-thiazol-5-ylamino]-benzyl}-carbamic acid tert-butyl ester;
5-(3-Aminomethyl-phenylamino)-2-methyl-thiazole-4-carboxylic acid (3-chloro-phenyl)-amide;
3-[2-Methyl-4-(6-methyl-pyridin-2-ylcarbamoyl)-thiazol-5-ylamino]-benzoic acid methyl ester;
5-(3-Hydroxymethyl-phenylamino)-2-methyl-thiazole-4-carboxylic acid (6-methyl-pyridin-2-yl)-amide;
5-(3-Methanesulfonyl-phenylamino)-2-methyl-thiazole-4-carboxylic acid (6-methyl-pyridin-2-yl)-amide;
2-Methyl-5-(3-sulfamoyl-phenylamino)-thiazole-4-carboxylic acid (6-methyl-pyridin-2-yl)-amide;
5-(2-Fluoro-5-methanesulfonyl-phenylamino)-2-methyl-thiazole-4-carboxylic acid (2-methyl-pyridin-4-yl)-amide;
2-Methyl-5-(3-sulfamoyl-phenylamino)-thiazole-4-carboxylic acid (2-methyl-pyridin-4-yl)-amide;
2-Methyl-5-(3-sulfamoyl-phenylamino)-thiazole-4-carboxylic acid (5-fluoro-pyridin-2-yl)-amide;
5-(3-Methanesulfonyl-phenylamino)-2-methyl-thiazole-4-carboxylic acid (5-fluoro-pyridin-2-yl)-amide;
5-(4-Fluoro-phenylamino)-2-methyl-thiazole-4-carboxylic acid (2-chloro-pyridin-4-yl)-amide;
5-((3-Difluoromethoxy-phenyl)amino)-2-methyl-thiazole-4-carboxylic acid (5-fluoro-pyridin-2-yl)-amide;
5-(3-Diethylsulfamoyl-phenylamino)-2-methyl-thiazole-4-carboxylic acid (5-fluoro-pyridin-2-yl)-amide;
2-Methyl-5-(3-oxazol-5-yl-phenylamino)-thiazole-4-carboxylic acid (2-methyl-pyrimidin-4-yl)-amide;
5-(3-Fluoro-phenylamino)-2-methyl-thiazole-4-carboxylic acid (2-methyl-pyrimidin-4-yl)-amide;
5-(3-Cyano-phenylamino)-2-methyl-thiazole-4-carboxylic acid (2-methyl-pyrimidin-4-yl)-amide;
5-(3-Ethylsulfamoyl-phenylamino)-2-methyl-thiazole-4-carboxylic acid (5-fluoro-pyridin-2-yl)-amide;
5-(3,5-Difluoro-phenylamino)-2-methyl-thiazole-4-carboxylic acid (2-methyl-pyrimidin-4-yl)-amide;
5-(3-Methanesulfonyl-phenylamino)-2-methyl-thiazole-4-carboxylic acid (2-methyl-pyrimidin-4-yl)-amide;
5-(3-Fluoro-phenylamino)-2-methyl-thiazole-4-carboxylic acid (2-methyl-pyridin-4-yl)-amide;
5-(3,5-Difluoro-phenylamino)-2-methyl-thiazole-4-carboxylic acid (2-methyl-pyridin-4-yl)-amide;
5-(3-Carbamoyl-phenylamino)-2-methyl-thiazole-4-carboxylic acid (2-methyl-pyrimidin-4-yl)-amide;
2-Methyl-5-((3-trifluoromethyl-phenyl)amino)-thiazole-4-carboxylic acid (2-methyl-pyridin-4-yl)-amide;
5-(3-Carbamoyl-phenylamino)-2-methyl-thiazole-4-carboxylic acid (2-methyl-pyridin-4-yl)-amide;
5-(3-Cyano-phenylamino)-2-methyl-thiazole-4-carboxylic acid (2-methyl-pyridin-4-yl)-amide;
3-[2-Methyl-4-(2-methyl-pyridin-4-ylcarbamoyl)-thiazol-5-ylamino]-benzoic acid methyl ester;
5-(2,5-Difluoro-phenylamino)-2-methyl-thiazole-4-carboxylic acid (2-methyl-pyridin-4-yl)-amide; and
5-(3,5-Difluoro-phenylamino)-2-methyl-thiazole-4-carboxylic acid (2-chloro-pyridin-4-yl)-amide.

15. A compound of claim 12, selected from the group consisting of
5-(3-Hydroxymethyl-phenylamino)-2-methyl-thiazole-4-carboxylic acid (2-methyl-pyridin-4-yl)-amide;
5-(3-Chloro-5-fluoro-phenylamino)-2-methyl-thiazole-4-carboxylic acid (2-methyl-pyridin-4-yl)-amide;
5-(3-Hydroxymethyl-phenylamino)-2-methyl-thiazole-4-carboxylic acid (2-chloro-pyridin-4-yl)-amide;
5-(3-Cyano-5-fluoro-phenylamino)-2-methyl-thiazole-4-carboxylic acid (2-methyl-pyridin-4-yl)-amide;
5-(3,5-Difluoro-phenylamino)-2-methyl-thiazole-4-carboxylic acid (2-hydroxymethyl-pyridin-4-yl)-amide;
5-(3-Imidazol-1-yl-phenylamino)-2-methyl-thiazole-4-carboxylic acid (2-methyl-pyridin-4-yl)-amide;
2-Methyl-5-[3-(1-methyl-1H-pyrazol-3-yl)-phenylamino]-thiazole-4-carboxylic acid (2-methyl-pyridin-4-yl)-amide;
5-(3,5-Difluoro-phenylamino)-2-methyl-thiazole-4-carboxylic acid (4-methyl-thiazol-2-yl)-amide;
5-(3,5-Difluoro-phenylamino)-2-methyl-thiazole-4-carboxylic acid (1-methyl-1H-[1,2,4]triazol-3-yl)-amide;
5-(3,5-Difluoro-phenylamino)-2-methyl-thiazole-4-carboxylic acid (3-methyl-[1,2,4]thiadiazol-5-yl)-amide;
5-(3,5-Difluoro-phenylamino)-2-methyl-thiazole-4-carboxylic acid (1-methyl-1H-pyrazol-3-yl)-amide;
2-Methyl-5-(3-[1,2,3]triazol-1-yl-phenylamino)-thiazole-4-carboxylic acid (2-methyl-pyridin-4-yl)-amide;
2-Methyl-5-[3-(2-methyl-imidazol-1-yl)-phenylamino]-thiazole-4-carboxylic acid (2-methyl-pyridin-4-yl)-amide;
{3-[2-Methyl-4-(2-methyl-pyridin-4-ylcarbamoyl)-thiazol-5-ylamino]-benzyl}-carbamic acid tert-butyl ester;
5-(3,5-Difluoro-phenylamino)-2-methyl-thiazole-4-carboxylic acid (1-cyclopropylmethyl-1H-pyrazol-3-yl)-amide;
5-(3-Methoxymethyl-phenylamino)-2-methyl-thiazole-4-carboxylic acid (2-methyl-pyridin-4-yl)-amide;
5-(3,5-Difluoro-phenylamino)-2-methyl-thiazole-4-carboxylic acid [3-(acetylamino-methyl)phenyl]-amide;
5-(3-Cyano-5-fluoro-phenylamino)-2-methyl-thiazole-4-carboxylic acid (1-methyl-1H-pyrazol-3-yl)-amide;
5-(3,5-Difluoro-phenylamino)-2-methyl-thiazole-4-carboxylic acid (4-cyclopropyl-thiazol-2-yl)-amide;
5-(3,5-Difluoro-phenylamino)-2-methyl-thiazole-4-carboxylic acid (3-methoxymethyl-phenyl)-amide;
5-(3,5-Difluoro-phenylamino)-2-methyl-thiazole-4-carboxylic acid [1-(2-methoxy-ethyl)-1H-pyrazol-3-yl]-amide;
5-[3-(Acetylamino-methyl)-phenylamino]-2-methyl-thiazole-4-carboxylic acid (2-methyl-pyridin-4-yl)-amide;
5-(3,5-Difluoro-phenylamino)-2-methyl-thiazole-4-carboxylic acid (5-fluoro-6-methyl-pyridin-2-yl)-amide;
5-(3,5-Difluoro-phenylamino)-2-methyl-thiazole-4-carboxylic acid (4-methoxymethyl-thiazol-2-yl)-amide;
5-(3-Methoxymethyl-phenylamino)-2-methyl-thiazole-4-carboxylic acid (1-methyl-1H-pyrazol-3-yl)-amide;
5-(3-Hydroxymethyl-phenylamino)-2-methyl-thiazole-4-carboxylic acid (1-methyl-1H-pyrazol-3-yl)-amide;
5-(3,5-Difluoro-phenylamino)-2-methyl-thiazole-4-carboxylic acid [1,3,4]thiadiazol-2-ylamide-5-(3,5-Difluoro-phenylamino)-2-methyl-thiazole-4-carboxylic acid (5-methyl-1H-[1,2,4]triazol-3-yl)-amide;
5-(2,5-Difluoro-phenylamino)-2-methyl-thiazole-4-carboxylic acid (1-methyl-1H-pyrazol-3-yl)-amide;
5-(3-Cyano-phenylamino)-2-methyl-thiazole-4-carboxylic acid (1-methyl-1H-pyrazol-3-yl)-amide; and
5-(3,5-Difluoro-phenylamino)-2-methyl-thiazole-4-carboxylic acid (3-cyano-5-fluoro-phenyl)-amide.

16. A compound of claim 1, wherein $R^3$ is $C_1$-$C_7$-alkyl or —$(CH_2)_m$—$R^b$, wherein $R^b$ is —O—$C_1$-$C_7$-alkyl, $C_3$-$C_6$-cycloalkyl, 5 or 6 membered heterocycloalkyl, aryl optionally substituted by fluoro, or heteroaryl optionally substituted by $C_1$-$C_7$-alkyl.

17. A compound of claim 16, selected from the group consisting of
- 5-Methylamino-thiazole-4-carboxylic acid (3-chloro-phenyl)-amide;
- 5-Methylamino-thiazole-4-carboxylic acid (3-fluoro-phenyl)-amide;
- 5-Methylamino-thiazole-4-carboxylic acid phenylamide;
- 5-Methylamino-thiazole-4-carboxylic acid m-tolylamide;
- 5-Methylamino-thiazole-4-carboxylic acid (3-bromo-phenyl)-amide;
- 5-Methylamino-thiazole-4-carboxylic acid (6-chloro-pyridin-2-yl)-amide;
- 5-Methylamino-thiazole-4-carboxylic acid (6-bromo-pyridin-2-yl)-amide;
- 5-Methylamino-thiazole-4-carboxylic acid (6-methyl-pyridin-2-yl)-amide;
- 5-Isobutylamino-thiazole-4-carboxylic acid (3-chloro-phenyl)-amide;
- 5-Isobutylamino-thiazole-4-carboxylic acid (3-fluoro-phenyl)-amide;
- 5-Isobutylamino-thiazole-4-carboxylic acid phenylamide;
- 5-Isobutylamino-thiazole-4-carboxylic acid m-tolylamide;
- 5-Isobutylamino-thiazole-4-carboxylic acid (3-bromo-phenyl)-amide;
- 5-Isobutylamino-thiazole-4-carboxylic acid (6-methyl-pyridin-2-yl)-amide;
- 5-Isobutylamino-thiazole-4-carboxylic acid (6-chloro-pyridin-2-yl)-amide;
- 5-Isobutylamino-thiazole-4-carboxylic acid (6-bromo-pyridin-2-yl)-amide;
- 5-tert-Butylamino-thiazole-4-carboxylic acid (3-chloro-phenyl)-amide;
- 5-tert-Butylamino-thiazole-4-carboxylic acid (3-fluoro-phenyl)-amide;
- 5-tert-Butylamino-thiazole-4-carboxylic acid m-tolylamide;
- 5-tert-Butylamino-thiazole-4-carboxylic acid (3-bromo-phenyl)-amide;
- 5-Isopropylamino-thiazole-4-carboxylic acid m-tolylamide;
- 5-Isopropylamino-thiazole-4-carboxylic acid (6-bromo-pyridin-2-yl)-amide;
- 5-Isopropylamino-thiazole-4-carboxylic acid (4-methyl-thiazol-2-yl)-amide;
- 5-(1,1-Dimethyl-propylamino)-thiazole-4-carboxylic acid (3-chloro-phenyl)-amide;
- 5-(1,1-Dimethyl-propylamino)-thiazole-4-carboxylic acid m-tolylamide;
- 5-(1,1-Dimethyl-propylamino)-thiazole-4-carboxylic acid (6-methyl-pyridin-2-yl)-amide;
- 5-(1,1-Dimethyl-propylamino)-thiazole-4-carboxylic acid (4-methyl-thiazol-2-yl)-amide;
- 5-Ethylamino-thiazole-4-carboxylic acid m-tolylamide;
- 5-Ethylamino-thiazole-4-carboxylic acid (6-bromo-pyridin-2-yl)-amide;
- 5-Ethylamino-thiazole-4-carboxylic acid (4-methyl-thiazol-2-yl)-amide;
- 5-Dimethylamino-2-methyl-thiazole-4-carboxylic acid (6-methyl-pyridin-2-yl)-amide;
- 2-Methyl-5-methylamino-thiazole-4-carboxylic acid (4-methyl-thiazol-2-yl)-amide; and
- 5-Dimethylamino-2-methyl-thiazole-4-carboxylic acid (4-methyl-thiazol-2-yl)-amide.

18. A compound of claim 1, selected from the group consisting of
- 5-(3-Methoxy-propylamino)-thiazole-4-carboxylic acid (3-chloro-phenyl)-amide;
- 5-(3-Methoxy-propylamino)-thiazole-4-carboxylic acid m-tolylamide;
- 5-(3-Methoxy-propylamino)-thiazole-4-carboxylic acid (3-bromo-phenyl)-amide;
- 5-Benzylamino-thiazole-4-carboxylic acid (6-methyl-pyridin-2-yl)-amide;
- 5-Benzylamino-thiazole-4-carboxylic acid (3-chloro-phenyl)-amide;
- 5-((Cyclopropylmethyl)-amino)-2-methyl-thiazole-4-carboxylic acid (2-methyl-pyrimidin-4-yl)-amide;
- 5-((Cyclopropylmethyl)-amino)-2-methyl-thiazole-4-carboxylic acid (2-chloro-pyridin-4-yl)-amide;
- 2-Methyl-5-[(tetrahydro-pyran-4-ylmethyl)-amino]-thiazole-4-carboxylic acid (2-methyl-pyridin-4-yl)-amide;
- 5-(3,5-Difluoro-benzylamino)-2-methyl-thiazole-4-carboxylic acid (2-methyl-pyridin-4-yl)-amide;
- 2-Methyl-5-[(pyridin-2-ylmethyl)-amino]-thiazole-4-carboxylic acid (2-methyl-pyridin-4-yl)-amide;
- 2-Methyl-5-[(3-methyl-3H-imidazol-4-ylmethyl)-amino]-thiazole-4-carboxylic acid (2-methyl-pyridin-4-yl)-amide;
- 5-(Cyclopropylmethyl-amino)-2-methyl-thiazole-4-carboxylic acid (1-methyl-1H-pyrazol-3-yl)-amide;
- 5-(Cyclopropylmethyl-amino)-2-methyl-thiazole-4-carboxylic acid (4-methyl-thiazol-2-yl)-amide;
- 2-Methyl-5-[(pyridin-3-ylmethyl)-amino]-thiazole-4-carboxylic acid (4-methyl-thiazol-2-yl)-amide;
- 5-(3,5-Difluoro-benzylamino)-2-methyl-thiazole-4-carboxylic acid (4-methyl-thiazol-2-yl)-amide; and
- 5-(2-Methoxy-ethylamino)-2-methyl-thiazole-4-carboxylic acid (2-methyl-pyridin-4-yl)-amide.

19. A compound of claim 1, wherein $R^3$ is —(CO)—$R^c$, wherein $R^c$ is —O—$(CH_2)_m$—$C_3$-$C_6$cycloalkyl or aryl or is $C_3$-$C_6$-cycloalkyl.

20. A compound of claim 19, selected from the group consisting of
- 5-Benzoylamino-2-methyl-thiazole-4-carboxylic acid (3-chloro-phenyl)-amide;
- Cyclopropylmethyl-[2-methyl-4-(2-methyl-pyrimidin-4-ylcarbamoyl)-thiazol-5-yl]-carbamic acid cyclopropylmethyl ester;
- 5-Cyclopropylamino-thiazole-4-carboxylic acid (3-chloro-phenyl)-amide;
- 5-Cyclopropylamino-thiazole-4-carboxylic acid (3-fluoro-phenyl)-amide;
- 5-Cyclopropylamino-thiazole-4-carboxylic acid phenylamide;
- 5-Cyclopropylamino-thiazole-4-carboxylic acid m-tolylamide;
- 5-Cyclopropylamino-thiazole-4-carboxylic acid (3-bromo-phenyl)-amide;
- 5-Cyclohexylamino-thiazole-4-carboxylic acid (3-chloro-phenyl)-amide;
- 5-Cyclopentylamino-thiazole-4-carboxylic acid (3-chloro-phenyl)-amide;
- 5-Cyclopentylamino-thiazole-4-carboxylic acid (3-fluoro-phenyl)-amide;
- 5-Cyclopentylamino-thiazole-4-carboxylic acid phenylamide;
- 5-Cyclopentylamino-thiazole-4-carboxylic acid m-tolylamide;
- 5-Cyclopentylamino-thiazole-4-carboxylic acid (3-bromo-phenyl)-amide;
- 5-Cyclopentylamino-thiazole-4-carboxylic acid (6-methyl-pyridin-2-yl)-amide;

5-Cyclopentylamino-thiazole-4-carboxylic acid (6-chloro-pyridin-2-yl)-amide;

5-Cyclopentylamino-thiazole-4-carboxylic acid (6-bromo-pyridin-2-yl)-amide; and

5-Cyclopropylamino-2-methyl-thiazole-4-carboxylic acid (2-methyl-pyridin-4-yl)-amide.

21. A compound of claim 1, wherein $R^4$ is hydrogen.

22. A compound of claim 1, wherein $R^1$ is aryl, optionally substituted by one or more substituents selected from the group consisting of —OH, chloro, fluoro, bromo, cyano, $C_1$-$C_7$-alkyl, $C_1$-$C_7$-alkoxy, —O—(CO)—$C_1$-$C_7$-alkyl, $C_3$-$C_6$-cycloalkyl, and —$(CH_2)_m$—$R^a$,
    wherein $R^a$ is —OH, —$CH_2F$, —$CHF_2$, —$CF_3$, $C_1$-$C_7$-alkoxy, $C_3$-$C_6$-cycloalkyl, —NH(CO)—$C_1$-$C_7$-alkyl, or —O—(CO)—$C_1$-$C_7$-alkyl.

23. A compound of claim 1, wherein $R^1$ is heteroaryl, optionally substituted by one or more substituents selected from the group consisting of —OH, chloro, fluoro, bromo, cyano, $C_1$-$C_7$-alkyl, $C_1$-$C_7$-alkoxy, —O—(CO)—$C_1$-$C_7$-alkyl, $C_3$-$C_6$-cycloalkyl, and —$(CH_2)_m$—$R^a$,
    wherein $R^a$ is —OH, —$CH_2F$, —$CHF_2$, —$CF_3$, $C_1$-$C_7$-alkoxy, $C_3$-$C_6$-cycloalkyl, —NH(CO)—$C_1$-$C_7$-alkyl, or —O—(CO)—$C_1$-$C_7$-alkyl.

24. A compound of claim 1, wherein $R^2$ is hydrogen or $C_1$-$C_7$-alkyl.

25. A pharmaceutical composition comprising a compound of formula I

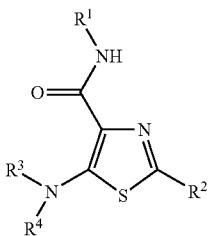

(I)

wherein $R^1$ is aryl or heteroaryl, each of which is optionally substituted by one or more substituents selected from the group consisting of —OH, chloro, fluoro, bromo, cyano, $C_1$-$C_7$-alkyl, $C_1$-$C_7$-alkoxy, —O—(CO)—$C_1$-$C_7$-alkyl, $C_3$-$C_6$-cycloalkyl, and —$(CH_2)_m$—$R^a$, wherein $R^a$ is —OH, —$CH_2F$, —$CHF_2$, —$CF_3$, $C_1$-$C_7$-alkoxy, $C_3$-$C_6$-cycloalkyl, —NH(CO)—$C_1$-$C_7$-alkyl, or —O—(CO)—$C_1$-$C_7$-alkyl;

$R^2$ is H, $C_1$-$C_7$-alkyl, —$(CH_2)_m$—O—$C_1$-$C_7$-alkyl or $C_3$-$C_6$-cycloalkyl;

$R^3$ is $C_1$-$C_7$-alkyl;
  —$(CH_2)_m$—$R^b$,
    wherein $R^b$ is —O—$C_1$-$C_7$-alkyl, $C_3$-$C_6$-cycloalkyl, 5 or 6 membered heterocycloalkyl, aryl optionally substituted by fluoro, or heteroaryl optionally substituted by $C_1$-$C_7$-alkyl;
  —(CO)—$R^c$,
    wherein $R^c$ is —O—$(CH_2)_m$—$C_3$-$C_6$-cycloalkyl, or aryl;
  $C_3$-$C_6$-cycloalkyl;
  5 or 6 membered heterocycloalkyl;
  aryl or heteroaryl, each of which is optionally substituted by
    cyano,
    chloro,
    fluoro,
    bromo,
    $CF_3$,
    $CHF_2$,
    $C_3$-$C_6$-cycloalkyl, or
    —O—$C_1$-$C_7$-alkyl;
  —(CO)—$R^d$,
    wherein $R^d$ is $C_1$-$C_7$-alkyl, $NH_2$, or —O—$C_1$-$C_7$-alkyl;
  —$(CH_2)_m$—$R^e$,
    wherein $R^e$ is OH, $C_1$-$C_7$-alkoxy, $CHF_2$, $CF_3$, $NH_2$, —NH—(CO)—$C_1$-$C_7$-alkyl, or —NH—(CO)—O—$C_1$-$C_7$-alkyl;
  —NH—(CO)—$C_1$-$C_7$-alkyl;
  —O—$CH_2F$;
  —O—$CHF_2$;
  —O—$CF_3$;
  —$S(O)_2$—$R^f$,
    wherein $R^f$ is $C_1$-$C_7$-alkyl, —$NH_2$, —NH—$C_1$-$C_7$-alkyl or —N-di($C_1$-$C_7$-alkyl); or heteroaryl optionally substituted by $C_1$-$C_7$-alkyl;

$R^4$ is H, $C_1$-$C_7$-alkyl or $C_1$-$C_7$-alkyl-$C_3$-$C_6$-cycloalkyl;

m is 1 to 4;

or a pharmaceutically acceptable salt thereof.

* * * * *